United States Patent
Jang et al.

(10) Patent No.: US 11,678,572 B2
(45) Date of Patent: *Jun. 13, 2023

(54) COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY APPARATUS

(71) Applicant: SAMSUNG SDI CO., LTD., Yongin-si (KR)

(72) Inventors: Kipo Jang, Suwon-si (KR); Jun Seok Kim, Suwon-si (KR); Jinhyun Lui, Suwon-si (KR); Chang Ju Shin, Suwon-si (KR); Sujin Han, Suwon-si (KR); Youngkwon Kim, Suwon-si (KR); Eun Sun Yu, Suwon-si (KR); Sung-Hyun Jung, Suwon-si (KR); Ho Kuk Jung, Suwon-si (KR)

(73) Assignee: SAMSUNG SDI CO., LTD., Yongin-si (KR)

(*) Notice: Subject to any disclaimer, the term of this patent is extended or adjusted under 35 U.S.C. 154(b) by 574 days.

This patent is subject to a terminal disclaimer.

(21) Appl. No.: 16/099,523

(22) PCT Filed: Jan. 18, 2017

(86) PCT No.: PCT/KR2017/000618
§ 371 (c)(1),
(2) Date: Nov. 7, 2018

(87) PCT Pub. No.: WO2018/004095
PCT Pub. Date: Jan. 4, 2018

(65) Prior Publication Data
US 2019/0165281 A1    May 30, 2019

(30) Foreign Application Priority Data
Jun. 29, 2016 (KR) .......... 10-2016-0081769

(51) Int. Cl.
*H10K 85/60* (2023.01)
*C07D 405/14* (2006.01)
(Continued)

(52) U.S. Cl.
CPC ........ *H01L 51/0067* (2013.01); *C07D 209/86* (2013.01); *C07D 251/24* (2013.01);
(Continued)

(58) Field of Classification Search
CPC ... H01L 51/0067; H01L 51/508; H01L 51/00; H01L 51/50; H01L 51/0072;
(Continued)

(56) References Cited

U.S. PATENT DOCUMENTS 6,229,012 B1    5/2001  Hu et al.
9,209,406 B2   12/2015  Mizutani et al.
(Continued)

FOREIGN PATENT DOCUMENTS

CN    102850329 A    1/2013
CN    103380508 A    10/2013
(Continued)

OTHER PUBLICATIONS

Organic Electronics, vol. 38, (2016), pp. 301-306. (Year: 2016).*
(Continued)

*Primary Examiner* — Dawn L Garrett
(74) *Attorney, Agent, or Firm* — Lee IP Law, P.C.

(57) ABSTRACT

Disclosed are a compound for an organic optoelectronic device represented by Chemical Formula 1, a composition for an organic optoelectronic device, an organic optoelectronic device including the same, and a display device. Details of Chemical Formula 1 are the same as defined in the specification.

16 Claims, 1 Drawing Sheet

(51) Int. Cl.

| | | |
|---|---|---|
| *C09K 11/06* | (2006.01) | |
| *C07D 333/76* | (2006.01) | |
| *C07D 307/91* | (2006.01) | |
| *C07D 409/14* | (2006.01) | |
| *H10K 99/00* | (2023.01) | |
| *H10K 50/00* | (2023.01) | |
| *C07D 251/24* | (2006.01) | |
| *H10K 50/16* | (2023.01) | |
| *C07D 209/86* | (2006.01) | |
| *C07D 405/04* | (2006.01) | |
| *C07D 409/04* | (2006.01) | |
| *H10K 50/11* | (2023.01) | |
| *H10K 50/15* | (2023.01) | |
| *H10K 50/17* | (2023.01) | |
| *H10K 50/18* | (2023.01) | |
| *H10K 101/00* | (2023.01) | |
| *H01L 51/00* | (2006.01) | |
| *H01L 51/50* | (2006.01) | |

(52) U.S. Cl.
CPC ......... *C07D 307/91* (2013.01); *C07D 333/76* (2013.01); *C07D 405/04* (2013.01); *C07D 405/14* (2013.01); *C07D 409/04* (2013.01); *C07D 409/14* (2013.01); *C09K 11/06* (2013.01); *H01L 51/00* (2013.01); *H01L 51/0072* (2013.01); *H01L 51/0073* (2013.01); *H01L 51/0074* (2013.01); *H01L 51/50* (2013.01); *H01L 51/508* (2013.01); *C09K 2211/1018* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 2251/5384* (2013.01)

(58) Field of Classification Search
CPC ............. H01L 51/0073; H01L 51/0074; H01L 51/5016; H01L 51/5056; H01L 51/5072; H01L 51/5088; H01L 51/5092; H01L 51/5096; H01L 2251/5384; C07D 333/76; C07D 307/91; C07D 409/14; C07D 251/24; C07D 209/86; C07D 405/04; C07D 409/04; C07D 405/14; C09K 11/06; C09K 2211/1018
See application file for complete search history.

(56) References Cited

U.S. PATENT DOCUMENTS

| | | | |
|---|---|---|---|
| 9,893,290 B2 * | 2/2018 | Min | H01L 51/0072 |
| 11,158,817 B2 * | 10/2021 | Lui | H01L 51/0067 |
| 11,264,574 B2 * | 3/2022 | Jang | H01L 51/0072 |
| 2004/0164292 A1 | 8/2004 | Tung | |
| 2006/0046342 A1 | 3/2006 | Karg et al. | |
| 2007/0141387 A1 | 6/2007 | Nakano et al. | |
| 2013/0264560 A1 | 10/2013 | Dobbs et al. | |
| 2014/0001456 A1 | 1/2014 | Mizutani et al. | |
| 2014/0361258 A1 | 12/2014 | Hwang et al. | |
| 2015/0028320 A1 | 1/2015 | Kinoshita et al. | |
| 2015/0171336 A1 | 6/2015 | Park et al. | |
| 2015/0171340 A1 | 6/2015 | Lee et al. | |
| 2015/0207082 A1 | 7/2015 | Dyatkin | |
| 2015/0349268 A1 | 12/2015 | Zeng et al. | |
| 2016/0028021 A1 | 1/2016 | Zeng | |
| 2016/0329502 A1 | 11/2016 | Dyatkin et al. | |
| 2017/0025618 A1 | 1/2017 | Zheng et al. | |
| 2017/0117488 A1 | 4/2017 | Ahn | |
| 2018/0033975 A1 | 2/2018 | Kim | |
| 2018/0337341 A1 * | 11/2018 | Heo | C07D 405/10 |

FOREIGN PATENT DOCUMENTS

| | | |
|---|---|---|
| CN | 104271703 A | 1/2015 |
| CN | 103232843 B | 2/2015 |
| CN | 104812750 A | 7/2015 |
| CN | 104885247 A | 9/2015 |
| CN | 104995187 A | 10/2015 |
| CN | 105153130 A | 12/2015 |
| CN | 105315219 A | 2/2016 |
| CN | 105315265 A | 2/2016 |
| CN | 105359290 A | 2/2016 |
| CN | 105473684 A | 4/2016 |
| CN | 105601612 A | 5/2016 |
| CN | 107093677 A | 8/2017 |
| CN | 107325090 A | 11/2017 |
| CN | 108290854 A | 7/2018 |
| EP | 2 966 706 A2 | 1/2016 |
| EP | 3 268 449 A1 | 2/2016 |
| JP | 2014/040423 A | 3/2014 |
| JP | 2014-123687 A | 7/2014 |
| JP | 5541167 B2 | 7/2014 |
| JP | 2014-157947 A | 8/2014 |
| JP | 5847420 B2 | 1/2016 |
| JP | 2016/019002 A | 2/2016 |
| JP | 2016-506414 A | 3/2016 |
| JP | 2016-525081 A | 8/2016 |
| JP | 2018-514081 A | 5/2018 |
| KR | 10-2011-0096453 | 8/2011 |
| KR | 10-2010-0118690 | 11/2011 |
| KR | 10-2012-0129733 A | 11/2012 |
| KR | 10-2013-0036048 A | 4/2013 |
| KR | 10-2013-0061371 | 6/2013 |
| KR | 10-2014-0005804 A | 1/2014 |
| KR | 10-2014-0010133 | 1/2014 |
| KR | 10-1423067 B1 | 7/2014 |
| KR | 10-2014-0144550 A | 12/2014 |
| KR | 10-2015-0036736 | 4/2015 |
| KR | 10-2015-0042335 A | 4/2015 |
| KR | 10-2015-0070860 A | 6/2015 |
| KR | 10-1542714 B1 | 7/2015 |
| KR | 10-2015-0116776 A | 10/2015 |
| KR | 10-2015-0129282 A | 11/2015 |
| KR | 10-2015-0131998 A | 11/2015 |
| KR | 10-2015-0136942 | 12/2015 |
| KR | 10-2016-0006633 A | 1/2016 |
| KR | 10-1593465 B1 | 2/2016 |
| KR | 10-2016-0028524 A | 3/2016 |
| KR | 10-2016-0034528 A | 3/2016 |
| KR | 2016-37909 | 3/2016 |
| KR | 10-2016-0038006 A | 4/2016 |
| KR | 10-2016-0055556 A | 5/2016 |
| KR | 10-2016-0080090 A | 7/2016 |
| KR | 10-2016-0110078 A | 9/2016 |
| KR | 10-2017-0022865 | 3/2017 |
| KR | 10-2017-0089599 A | 8/2017 |
| KR | 10-2017-0116992 A | 10/2017 |
| KR | 10-2017-0141144 A | 12/2017 |
| TW | 201609712 A | 3/2016 |
| TW | 201619152 A | 6/2016 |
| WO | WO 2010/044342 A1 | 4/2010 |
| WO | WO 2013/077352 A1 | 5/2013 |
| WO | WO 2014/054912 A1 | 4/2014 |
| WO | WO 2014208755 A1 | 12/2014 |
| WO | WO 2015/000549 A1 | 1/2015 |
| WO | WO 2015/156587 A1 | 10/2015 |
| WO | WO 2015/160224 A1 | 10/2015 |
| WO | WO 2016/076384 A1 | 5/2016 |
| WO | WO 2016084962 A1 | 6/2016 |
| WO | WO 2016 148390 A1 | 9/2016 |
| WO | WO 2016/172414 A1 | 10/2016 |
| WO | WO 2017/016630 A1 | 2/2017 |
| WO | WO 2017/146466 A1 | 8/2017 |
| WO | WO 2017/171420 A1 | 10/2017 |
| WO | WO 2018/016742 A1 | 1/2018 |
| WO | WO 2018/021663 A1 | 2/2018 |
| WO | WO 2018/062659 A1 | 4/2018 |
| WO | WO 2018/093026 A1 | 5/2018 |

(56) References Cited

FOREIGN PATENT DOCUMENTS

WO    WO 2018/097461 A1    5/2018
WO    WO 2018/128255 A1    7/2018

OTHER PUBLICATIONS

Machine translation of KR 20170089599 A (publication date Aug. 2017). (Year: 2017).*
Office action received in copending related U.S. Appl. No. 16/097,657.
Japanese Office action dated Sep. 29, 2020, received in Japanese Application No. 2018-568699.
Japanese Notice of Allowance dated Oct. 6, 2020, received in Japanese Application No. 2019-503551.
European Search Report dated Dec. 19, 2019, Application No. 17820373.3.
European Search Report dated Jan. 8, 2020, Application No. 17820372.5.
U.S. Office Action dated Jan. 13, 2021 from Co-pending U.S. Appl. No. 16/468,779.
Extended European Search Report dated Feb. 17, 2020, European Patent Application No. 17827792.7.
Extended European Search Report dated Feb. 28, 2020, European Patent Application No. 17834608.6.
International Search Report dated Apr. 24, 2017.
European Office action dated Mar. 25, 2021.
Final Office action received in Co-pending related U.S. Appl. No. 16/099,507, dated Sep. 24, 2021.
U.S. Office action received in co pending U.S. Appl. No. 16/099,507, dated Apr. 16, 2021.
U.S. Office Action received in Co Pending U.S. Appl. No. 16/321,228 dated Jun. 25, 2021.
European Office action received in copending Appln. No. EP17834608.6 dated Jan. 21, 2022.
European Office action received in corresponding EP No. EP 17820372.5 dated Dec. 17, 2021.
U.S. Advisory action received in copending U.S. Appl. No. 16/099,507 dated Dec. 1, 2021.
U.S. Office action received in co pending U.S. Appl. No. 16/099,507 dated May 17, 2022.
U.S. Office action received in co-pending U.S. Appl. No. 16/099,507, dated Oct. 21, 2022.

* cited by examiner

COMPOUND FOR ORGANIC OPTOELECTRONIC DEVICE, COMPOSITION FOR ORGANIC OPTOELECTRONIC DEVICE, ORGANIC OPTOELECTRONIC DEVICE AND DISPLAY APPARATUS

CROSS REFERENCE TO RELATED APPLICATIONS

This is the U.S. national phase application based on PCT Application No. PCT/KR 2017/000618, filed Jan. 18, 2017, which is based on Korean Patent Application No. 10-2016-0081769, filed Jun. 29, 2016, the entire contents of all of which are hereby incorporated by reference.

TECHNICAL FIELD

A compound for an organic optoelectronic device, a composition for an organic optoelectronic device, an organic optoelectronic device, and a display device are disclosed.

BACKGROUND ART

An organic optoelectronic device (organic optoelectronic diode) is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

DISCLOSURE

Technical Problem

An embodiment provides a composition for an organic optoelectronic device capable of realizing an organic optoelectronic device having high efficiency and a long life-span.

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

Technical Solution

According to an embodiment, a compound represented by Chemical Formula 1 for an organic optoelectronic device is provided.

[Chemical Formula 1]

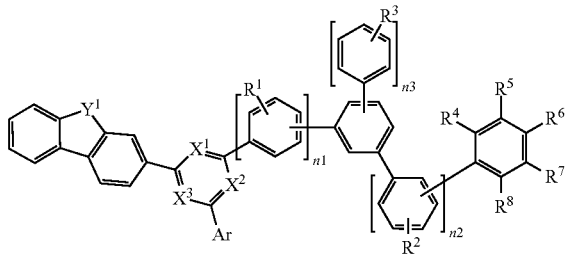

In Chemical Formula 1, $X^1$ to $X^3$ are independently N or $CR^a$, at least two of $X^1$ to $X^3$ are N, $Y^1$ is O or S, Ar is a substituted or unsubstituted C6 to C30 aryl group, $R^a$ and $R^1$ to $R^3$ are independently hydrogen, deuterium, a substituted or unsubstituted C1 to C10 alkyl group, a substituted or unsubstituted C6 to C30 aryl group, or a combination thereof, $R^4$ to $R^8$ are independently hydrogen, deuterium, a cyano group, a nitro group, a substituted or unsubstituted C1 to C10 alkyl group, a substituted or unsubstituted C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, a substituted or unsubstituted dibenzothiophenyl group, or a combination thereof, $R^4$ to $R^8$ are independently present or adjacent groups thereof are linked with each other to provide a substituted or unsubstituted aliphatic, aromatic, or heteroaromatic monocyclic ring or polycyclic ring and, n1 to n3 are independently an integer of 0 to 2, in case of n1+n2+n3=0, adjacent groups of $R^4$ to $R^8$ are linked with each other to provide a substituted or unsubstituted aliphatic, aromatic, or heteroaromatic monocyclic ring or polycyclic ring, and the "substituted" refers to replacement of at least one hydrogen by deuterium, a C1 to C20 alkyl group, a C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group.

According to another embodiment, a composition for an organic optoelectronic device includes the above compound for an organic optoelectronic device; and a second compound for an organic optoelectronic device represented by Chemical Formula 2.

[Chemical Formula 2]

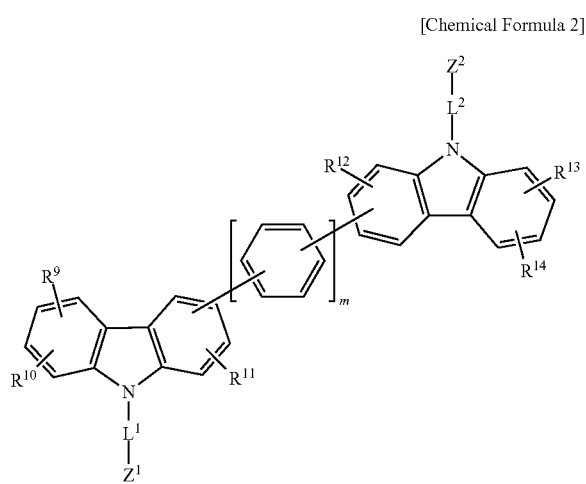

In Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^9$ to $R^{14}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group.

According to another embodiment, an organic optoelectronic device includes an anode and a cathode facing each other and at least one organic layer disposed between the anode and the cathode, wherein the organic layer includes the compound for an organic optoelectronic device, or the composition for an organic optoelectronic device.

According to another embodiment, a display device including the organic optoelectronic device is provided.

Advantageous Effects

An organic optoelectronic device having high efficiency and a long life-span may be realized.

DESCRIPTION OF SYMBOLS

Figure 1:
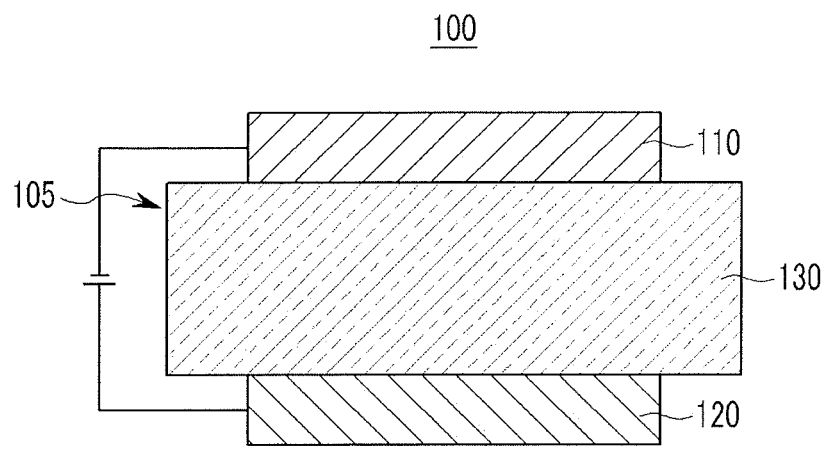
FIGS. 1 and 2 are cross-sectional views showing organic light emitting diodes according embodiments.

100, 200: organic light emitting diode
105: organic layer
110: cathode
120: anode
130: light-emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

As used herein, when a definition is not otherwise provided, the "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to 010 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a fluoro group, a C1 to 010 trifluoroalkyl group, a cyano group, or a combination thereof.

In one example of the present invention, the "substituted" refers to replacement of at least one hydrogen of a substituent or a compound by deuterium, a C1 to C20 alkyl group, a C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group.

As used herein, when a definition is not otherwise provided, "hetero" refers to one including one to three heteroatoms selected from N, O, S, P, and Si, and remaining carbons in one functional group.

As used herein, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to 010 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, an "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

As used herein, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in a light-emitting layer due to conductive characteristics according to a highest occupied molecular orbital (HOMO) level.

In addition, electron characteristics refer to an ability to accept an electron when an electric field is applied and that an electron formed in a cathode may be easily injected into a light-emitting layer, and an electron formed in a light-emitting layer may be easily transported into a cathode and transported in a light-emitting layer due to conductive characteristics according to a lowest unoccupied molecular orbital (LUMO) level. For example, ET core means a core which has electron characteristics.

Hereinafter, a compound for an organic optoelectronic device according to an embodiment is described.

A compound for an organic optoelectronic device according to an embodiment is represented by Chemical Formula 1.

[Chemical Formula 1]

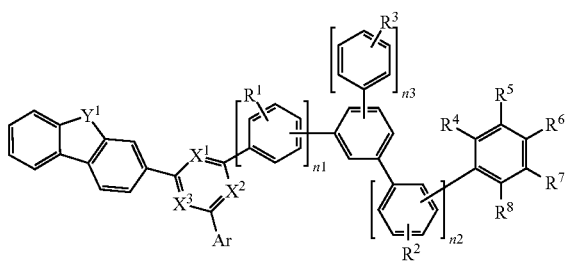

In Chemical Formula 1,
$X^1$ to $X^3$ are independently N or $CR^a$,
at least two of $X^1$ to $X^3$ are N,
$Y^1$ is O or S,
Ar is a substituted or unsubstituted C6 to C30 aryl group,
$R^a$ and $R^1$ to $R^3$ are independently hydrogen, deuterium, a substituted or unsubstituted C1 to 010 alkyl group, a substituted or unsubstituted C6 to C30 aryl group, or a combination thereof,
$R^4$ to $R^8$ are independently hydrogen, deuterium, a cyano group, a nitro group, a substituted or unsubstituted C1 to 010 alkyl group, a substituted or unsubstituted C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, a substituted or unsubstituted dibenzothiophenyl group, or a combination thereof,
$R^4$ to $R^8$ are independently present or adjacent groups thereof are linked with each other to provide a substituted or unsubstituted aliphatic, aromatic, or heteroaromatic monocyclic ring or polycyclic ring,
n1 to n3 are independently an integer of 0 to 2,
in case of n1+n2+n3=0, adjacent groups of $R^4$ to $R^8$ are linked with each other to provide a substituted or unsubstituted aliphatic, aromatic, or heteroaromatic monocyclic ring or polycyclic ring, and
the "substituted" refers to replacement of at least one hydrogen by deuterium, a C1 to C20 alkyl group, a C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group. In an embodiment of the present invention, the "substituted" refers to replacement of at least one hydrogen by deuterium, C1 to C5 alkyl group, a C6 to C18 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group. In a specific example embodiment of the present invention, the "substituted" refers to replacement of at least one hydrogen by deuterium, a phenyl group, a meta-biphenyl group, a para-biphenyl group, 3-dibenzofuranyl group, or a 3-dibenzothiophenyl group.

A compound for an organic optoelectronic device according to the present invention includes an ET core including an N-containing 6-membered ring that includes a substituent directly linked with dibenzofuran or dibenzothiophene at a position No. 3 without a linking group, and thereby a LUMO energy band is effectively expanded, planarity of a molecular structure is increased, and the compound may become a structure capable of accepting electrons when an electric field is applied, and accordingly an organic optoelectronic device including the compound for an organic optoelectronic device may exhibit a lowered driving voltage. Such a LUMO expansion and ring fusion increase stability for electrons of the ET core and life-span of a device is effectively improved.

In addition, interactions with adjacent molecules may be suppressed and crystallization is decreased due to steric hindrance characteristics by at least one meta-bound arylene and accordingly efficiency and life-span characteristics of an organic optoelectronic device including the compound for an organic optoelectronic device may be improved.

A kinked moiety such as the meta-bound arylene increases a glass transition temperature (Tg) of a compound and stability of a compound may be increased and degradation may be suppressed when it is applied to a device.

In the present invention, "adjacent groups thereof are linked with each other" in definition of $R^4$ to $R^8$ refers to fusion of a phenyl group linked with $R^4$ to $R^8$ with two substituents of $R^4$ to $R^8$ to provide a substituted or unsubstituted aliphatic, aromatic, or heteroaromatic monocyclic ring or polycyclic ring. For example, each of $R^4$ and $R^5$, $R^5$ and $R^6$, $R^6$ and $R^7$, and $R^7$ and $R^8$ may form a heteroaromatic polycyclic ring with the phenyl group. Herein examples of the heteroaromatic polycyclic ring may be a substituted or unsubstituted dibenzofuranyl group, a substituted or unsubstituted dibenzothiophenyl group, and the like, and for example adjacent groups of $R^4$ to $R^8$ may be linked with the phenyl group to provide a heteroaromatic polycyclic ring represented by Chemical Formula A.

[Chemical Formula A]

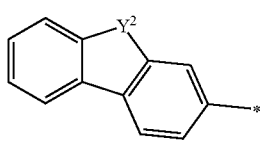

In Chemical Formula A, $Y^2$ is O or S, and * is a linking point with a substituted or unsubstituted phenylene.

Specific examples of a compound where adjacent groups of $R^4$ to $R^8$ are linked with each other to provide a heteroaromatic polycyclic ring may be "Compound B-10" of the following specific compounds of the present invention.

In an example embodiment of the present invention, an ET core consisting of $X^1$ to $X^3$ may be pyrimidine or triazine and may be for example represented by Chemical Formula 1-I, Chemical Formula 1-II, or Chemical Formula 1-III. More specifically, it may be represented by Chemical Formula 1-I or Chemical Formula 1-II.

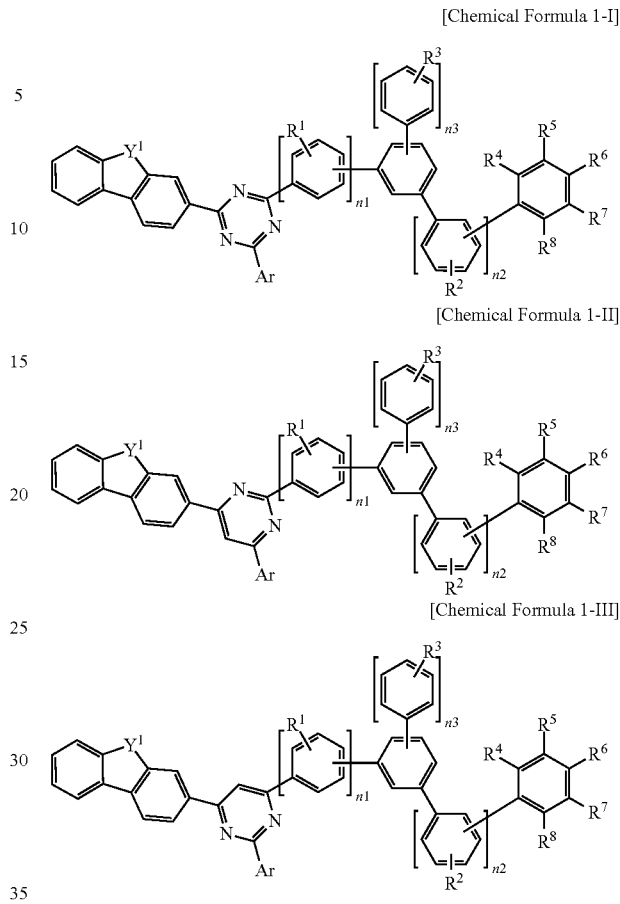

In Chemical Formula 1-I, Chemical Formula 1-II, and Chemical Formula 1-III, $Y^1$, Ar, $R^1$ to $R^8$, and n1 to n3 are the same as described above.

In an example embodiment of the present invention, n1 may be an integer ranging from 0 to 2 and n2 and n3 may independently be an integer of 0 or 1. When n1 is 2, each $R^1$ may be the same or different. Specifically, n1 may be an integer of 0 or 1.

In another example embodiment of the present invention, n2 may be an integer ranging from 0 to 2 and n1 and n3 may independently be an integer of 0 or 1. When n2 is 2, each $R^2$ may be the same or different. Specifically, n2 may be an integer of 0 or 1.

In another example embodiment of the present invention, n3 may be an integer ranging from 0 to 2 and n1 and n2 may independently be an integer of 0 or 1. When n3 is 2, each $R^3$ may be the same or different. Specifically, n3 may be an integer of 0 or 1.

In an example embodiment of the present invention, the n1 to n3 may independently be in integer of 0 or 1, for example n1 and n4 may be 0 or at least one of n1 and n2 may be 1.

Chemical Formula 1 may be for example represented by one of Chemical Formulae 1-1 to 1-5 according to presences of a linking group represented by

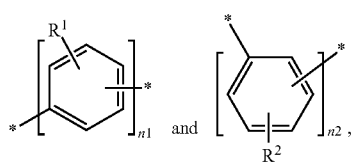

and a substituent represented by

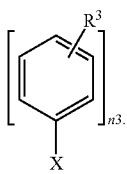

Herein, the linking group may be linked by a meta bond or a para bond.

[Chemical Formula 1-1]

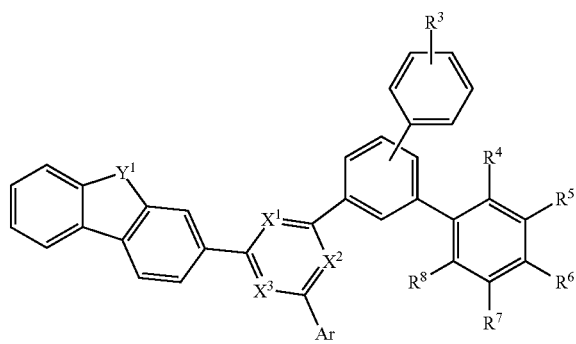

[Chemical Formula 1-2]

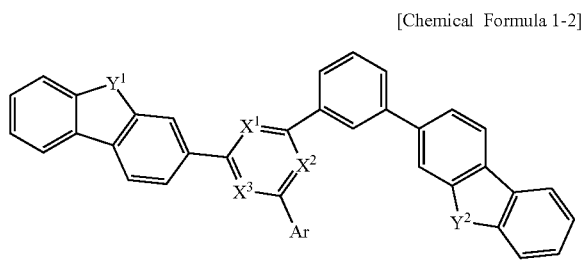

[Chemical Formula 1-3]

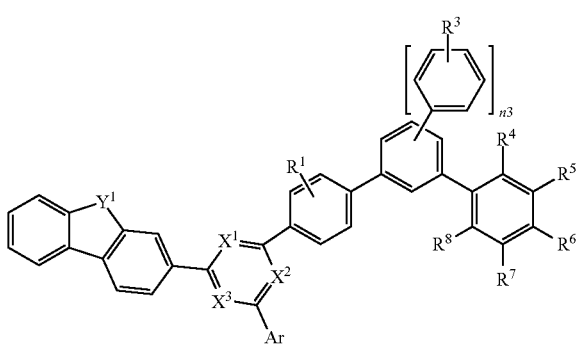

[Chemical Formula 1-4]

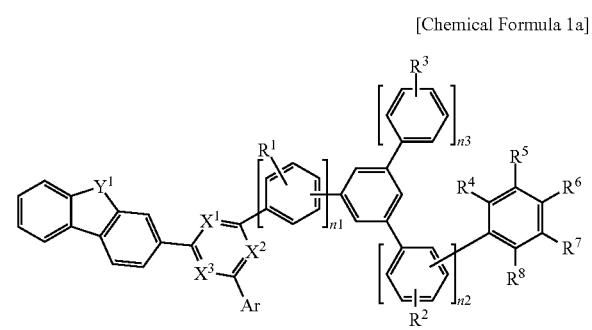

[Chemical Formula 1-5]

In Chemical Formulae 1-1 to 1-5, $R^1$ to $R^8$, $Y^1$ and $Y^2$, Ar, and n3 are the same as above, $X^1$ to $X^3$ are independently N or CH and at least two of $X^1$ to $X^3$ are N.

In an example embodiment of the present invention, Chemical Formula 1 may be represented by Chemical Formula 1-1, Chemical Formula 1-3, Chemical Formula 1-4, or Chemical Formula 1-5, and may be for example represented by Chemical Formula 1-4.

Particularly, when the substituent represented by is present, that is n3 is 1 or 2, Chemical Formula 1 may be represented by Chemical Formula 1a including a kinked terphenyl group.

[Chemical Formula 1a]

In addition, Chemical Formula 1 may be for example represented by one of Chemical Formula 1-1a, Chemical Formula 1-3a, Chemical Formula 1-4a, and Chemical Formula 1-5a according to presences of a linking group represented by

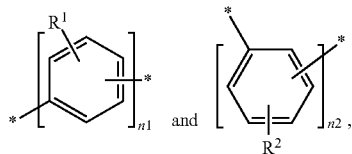

and a substituent represented by

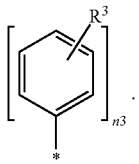

[Chemical Formula 1-1a]

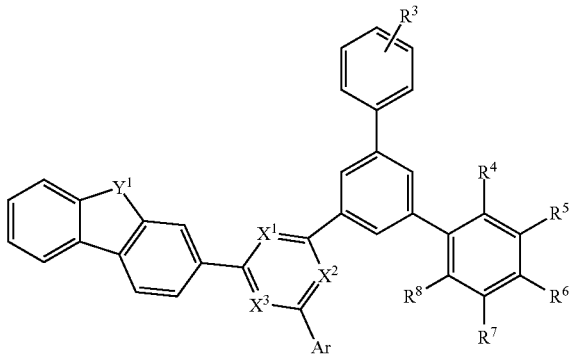

[Chemical Formula 1-3a]

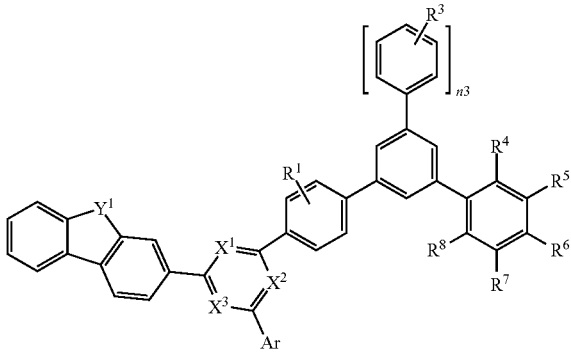

[Chemical Formula 1-4a]

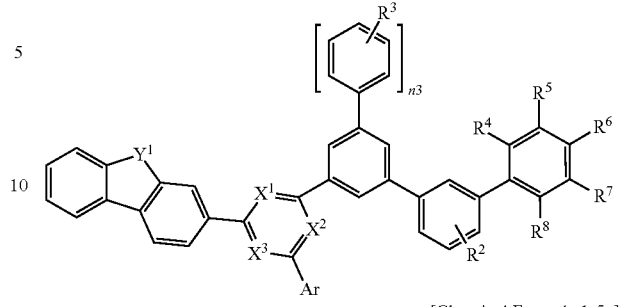

[Chemical Formula 1-5a]

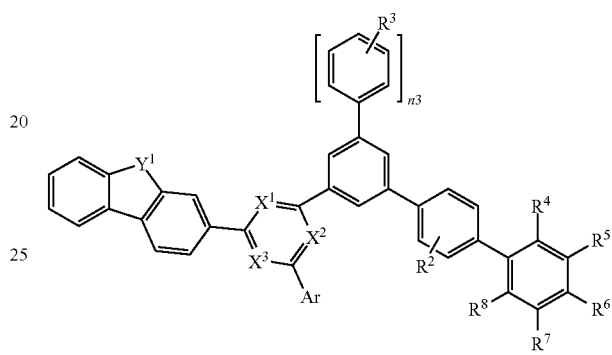

$Y^1$, $X^1$ to $X^3$, Ar, and $R^1$ to $R^8$ are the same as above and n3 is an integer of 1 or 2.

When the kinked terphenyl group is included, a glass transition temperature (Tg) may be increased effectively, and a low molecular weight compound having a high glass transition temperature (Tg) may be designed and thereby thermal characteristics may be ensured and stability and the like may be ensured.

The glass transition temperature (Tg) may have a relation with thermal stability of a compound and a device including the same. That is, when a compound for an organic optoelectronic device having a high glass transition temperature (Tg) is applied to an organic light emitting diode in a form of a thin film, degradation by temperature may be prevented and an organic compound and life-span characteristics of a device may be ensured in subsequent processes after deposition of the compound for an organic optoelectronic device.

In an example embodiment of the present invention, Ar may be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, or a combination thereof, for example, a phenyl group, a m-biphenyl group, or a p-biphenyl group.

In an example embodiment of the present invention, $R^a$ and $R^1$ to $R^3$ may independently be hydrogen, deuterium, a substituted or unsubstituted C1 to C10 alkyl group, a substituted or unsubstituted C6 to C30 aryl group, or a combination thereof, and specifically, hydrogen, deuterium, or a substituted or unsubstituted C6 to C18 aryl group, for example, hydrogen, or a phenyl group. In a specific example embodiment, $R^a$ may be hydrogen and $R^1$ to $R^3$ may be hydrogen or a phenyl group.

In an example embodiment of the present invention, $R^4$ to $R^8$ may be independently hydrogen, deuterium, a cyano group, a nitro group, a substituted or unsubstituted C1 to 010 alkyl group, a substituted or unsubstituted C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, a substituted or unsubstituted dibenzothiophenyl group, or a combination thereof, and $R^4$ to $R^8$ may independently be present or adjacent groups thereof may be linked with each other to provide a substituted or unsubstituted aliphatic, aromatic, or heteroaromatic monocyclic ring or polycyclic ring $R^4$ to $R^8$ may be independently present or adjacent groups thereof are linked with each other to provide a substituted or unsubstituted aliphatic, aromatic, or heteroaromatic monocyclic ring or polycyclic ring and examples of the heteroaromatic polycyclic ring may be a dibenzofuranyl group or a dibenzothiophenyl group.

For example, all $R^4$ to $R^8$ may be hydrogen or at least one of $R^5$ to $R^7$ may be a phenyl group, a biphenyl group, a dibenzofuranyl group, or a dibenzothiophenyl group and the rest may be hydrogen.

In addition, $R^5$ and $R^6$ or $R^6$ and $R^7$ are linked with each other to provide a heteroaromatic polycyclic ring represented by Chemical Formula A.

The compound for an organic optoelectronic device represented by Chemical Formula 1 may be for example selected from compounds of Group 1, but is not limited thereto.

[Group 1]

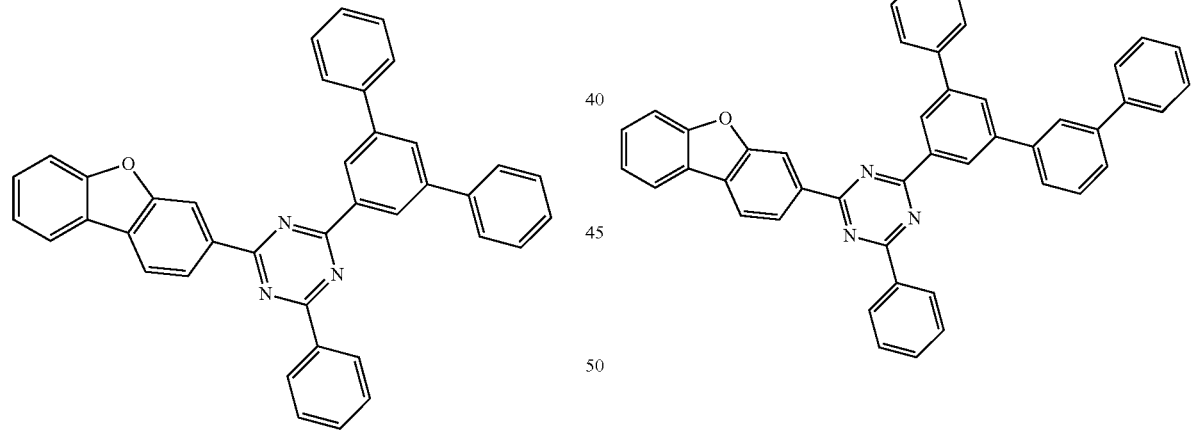

[B-1]

[B-2]

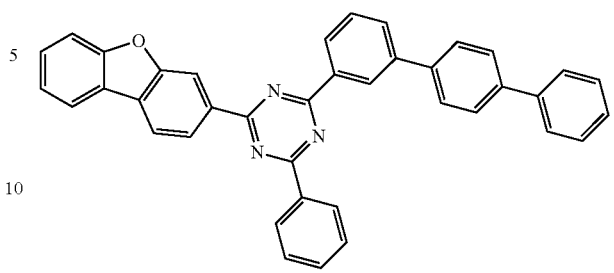

[B-3]

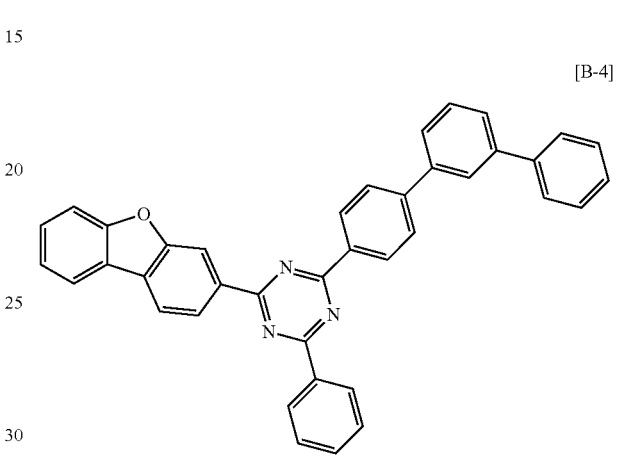

[B-4]

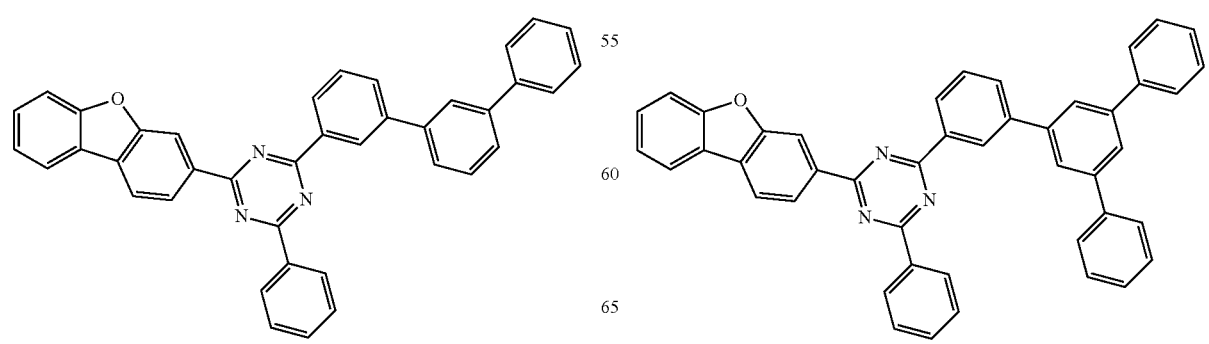

[B-5]

[B-6]

[B-7]
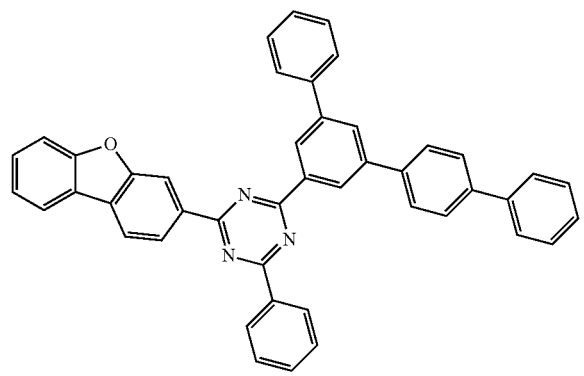
[B-11]
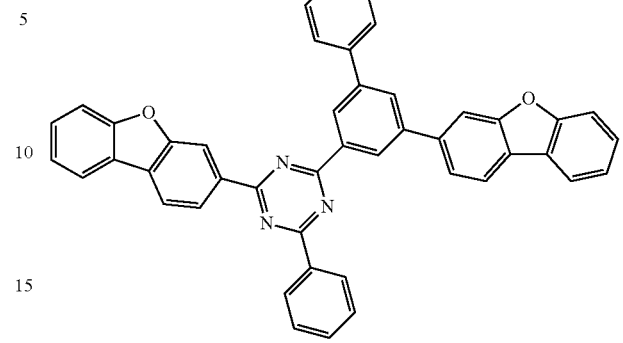
[B-8]
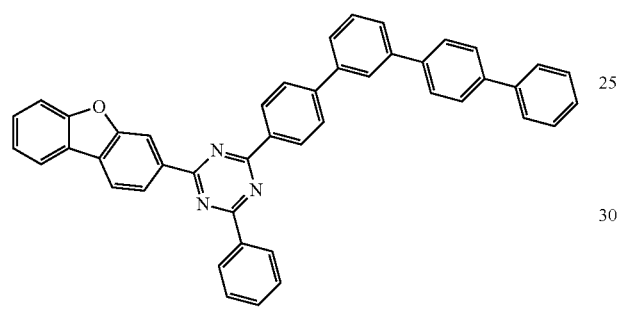
[B-12]
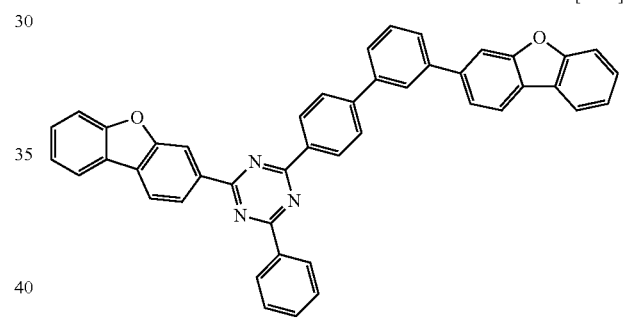
[B-9]
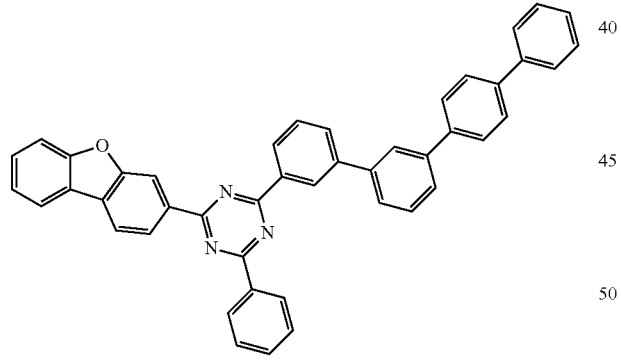
[B-10]
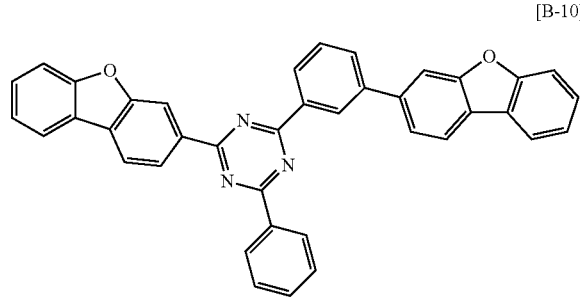
[B-13]
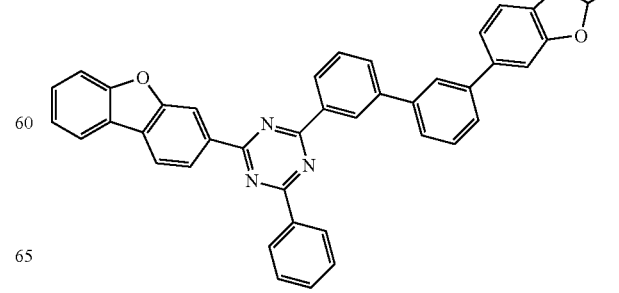

[B-14]
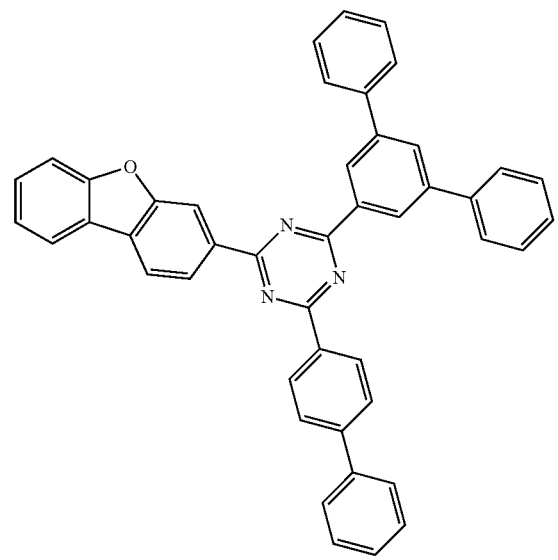
[B-15]
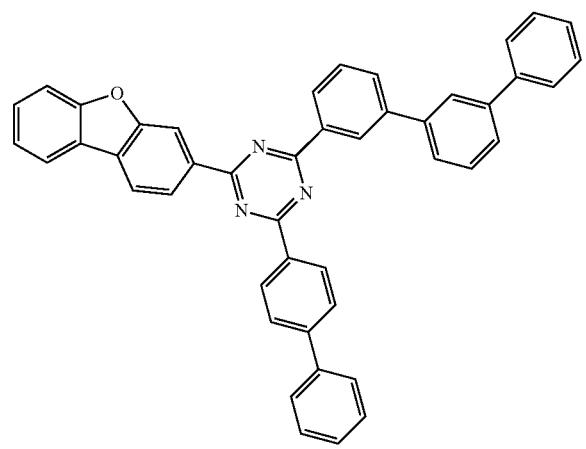
[B-16]
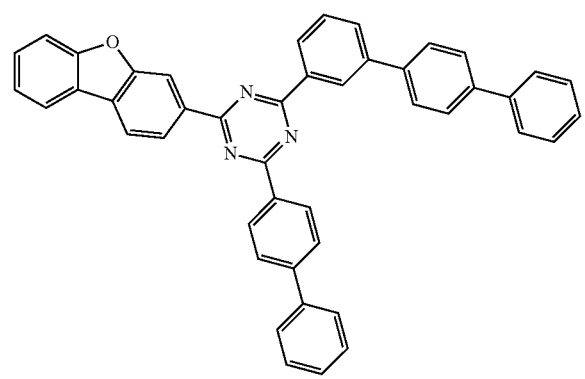
[B-17]
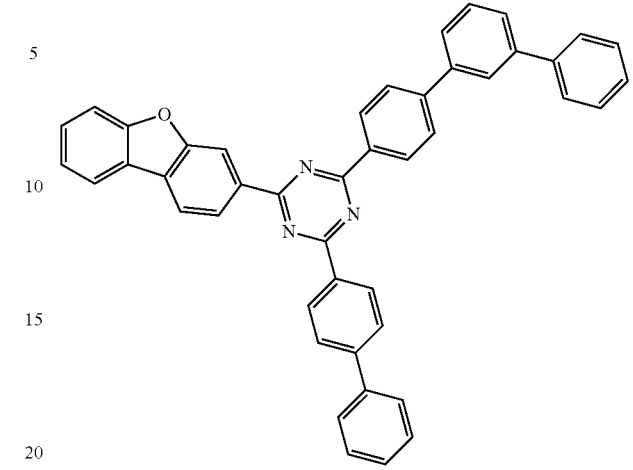
[B-18]
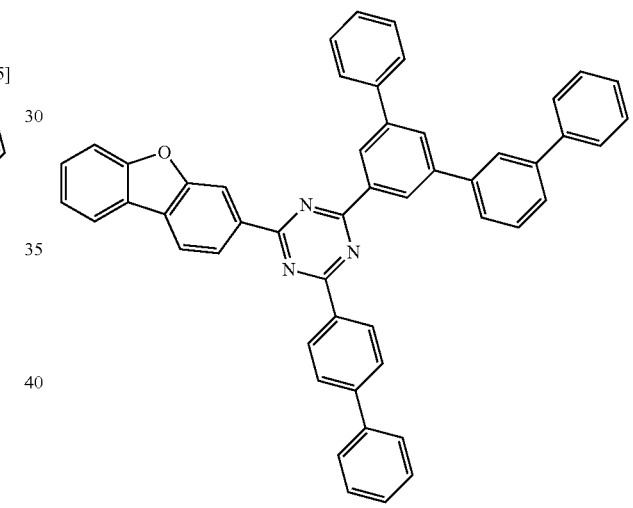
[B-19]
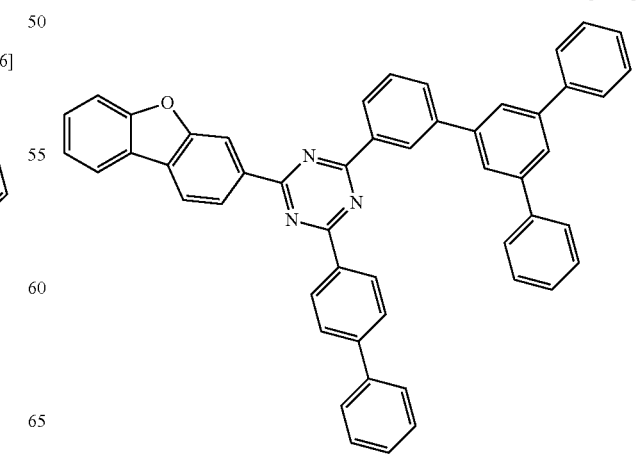

[B-20]
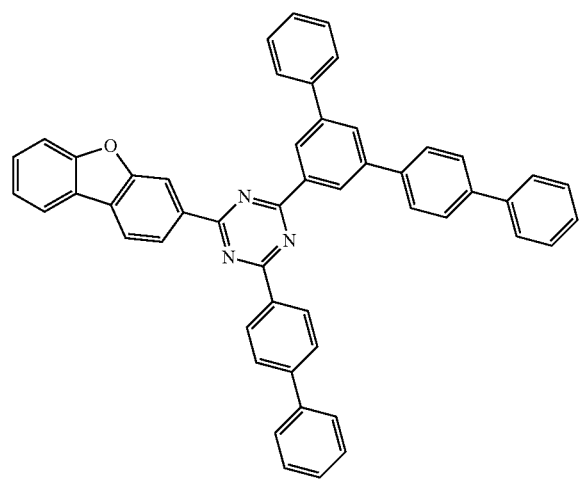
[B-23]
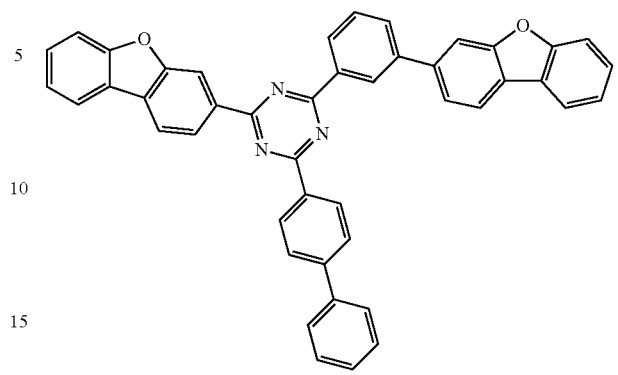
[B-21]
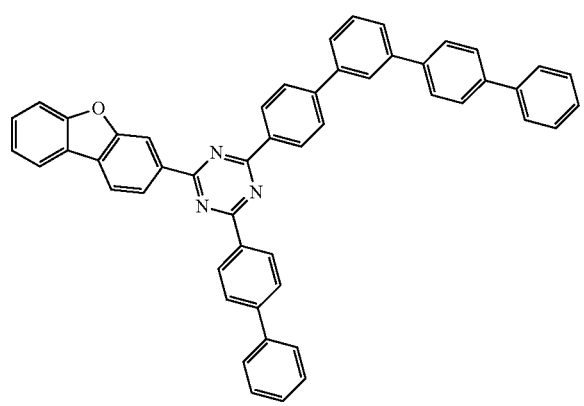
[B-24]
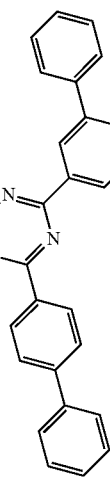
[B-22]
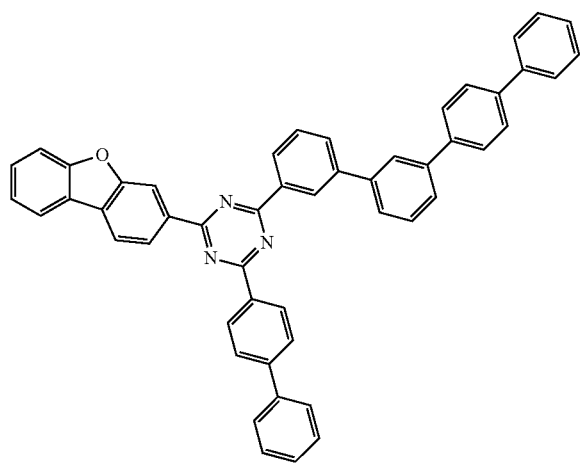
[B-25]
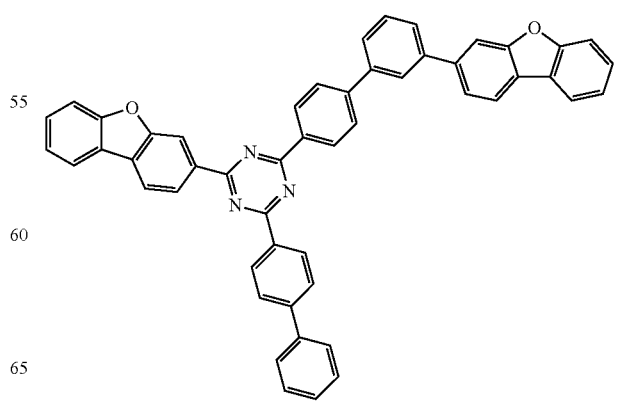

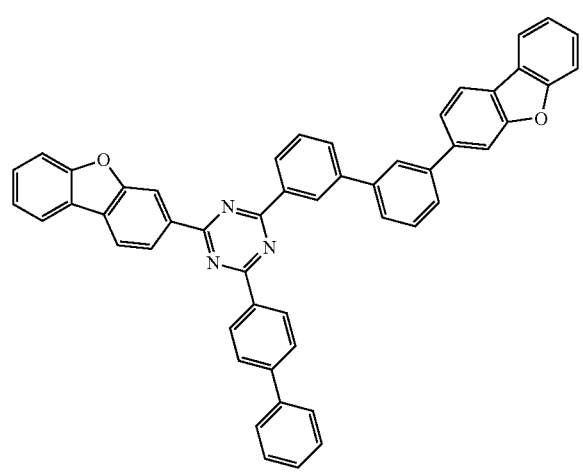
[B-26]
[B-27]
[B-28]
[B-29]
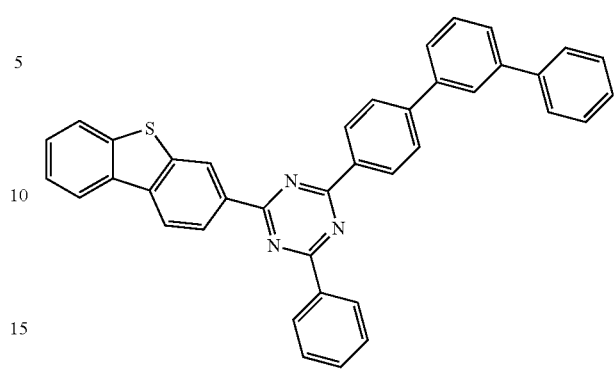
[B-30]
[B-31]
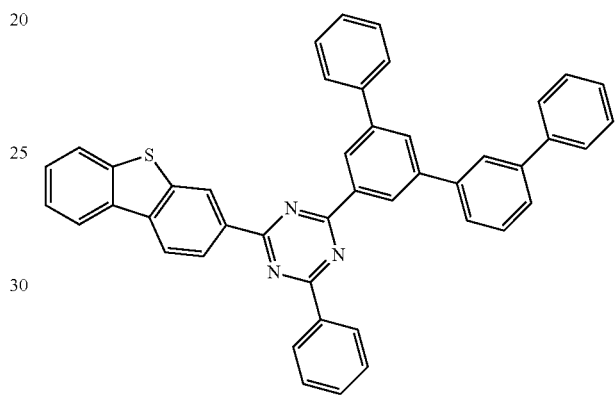
[B-32]
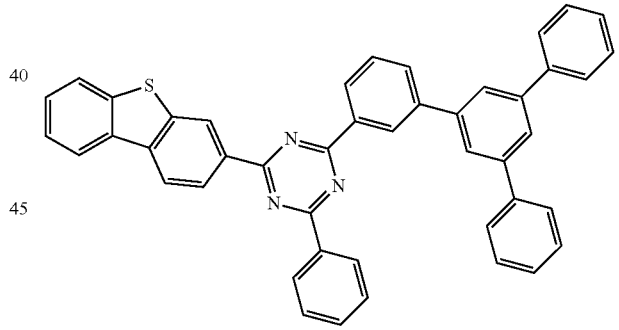
[B-33]
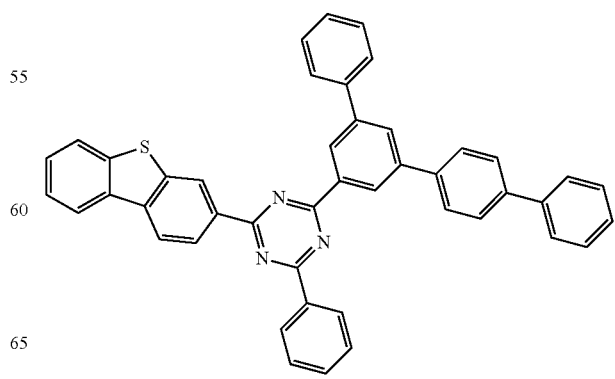

[B-34]
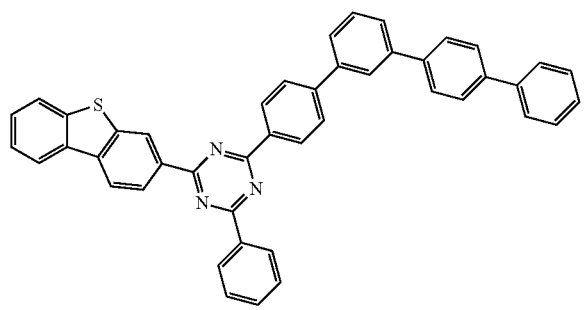
[B-38]
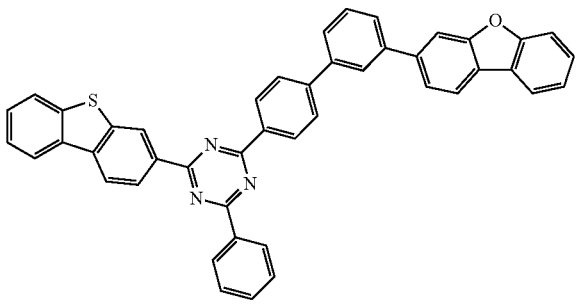
[B-35]
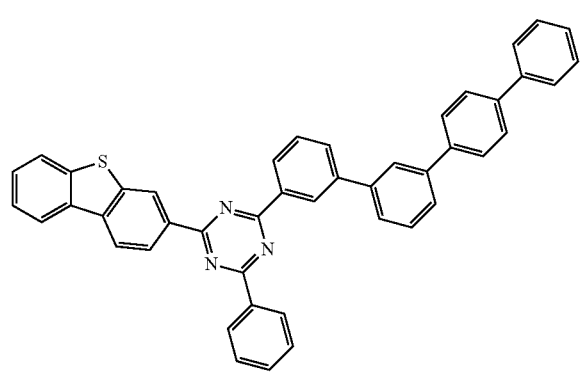
[B-39]
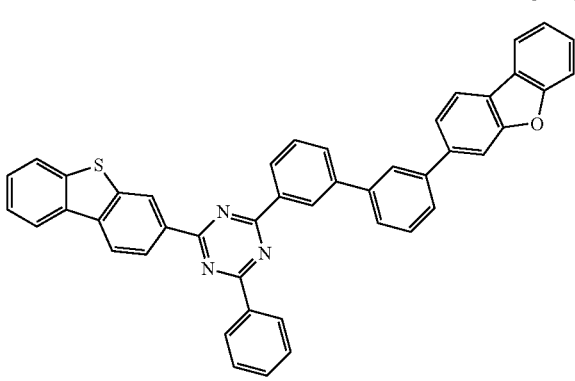
[B-36]
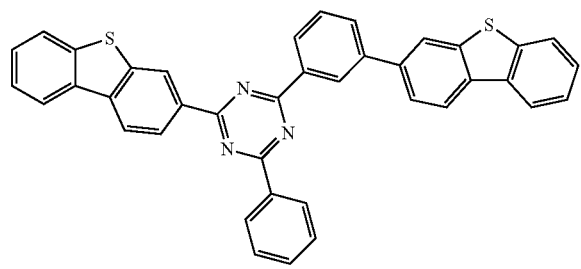
[B-37]
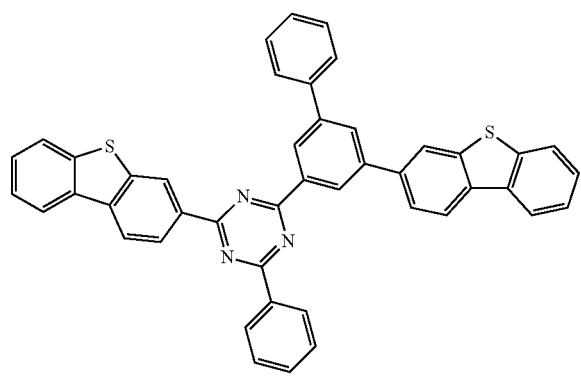
[B-40]
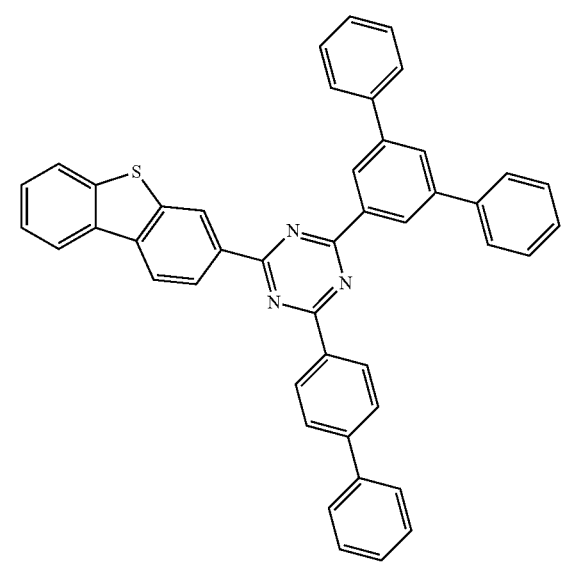

[B-41]
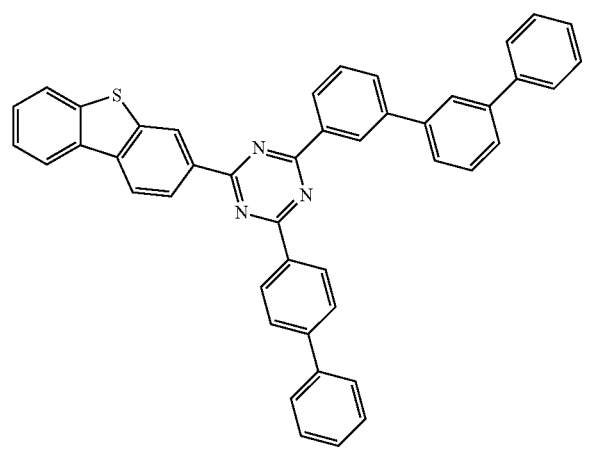
[B-42]
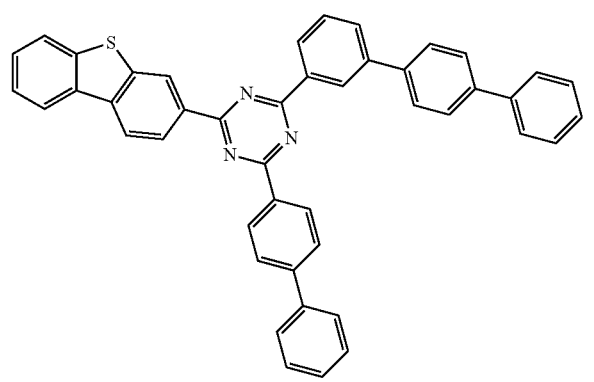
[B-43]
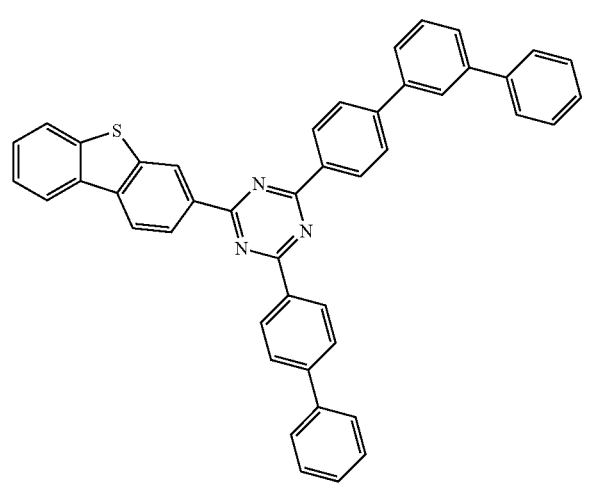
[B-44]
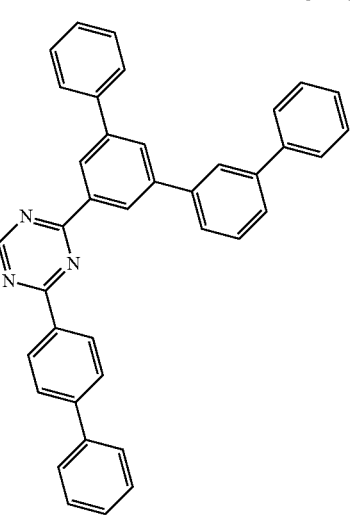
[B-45]
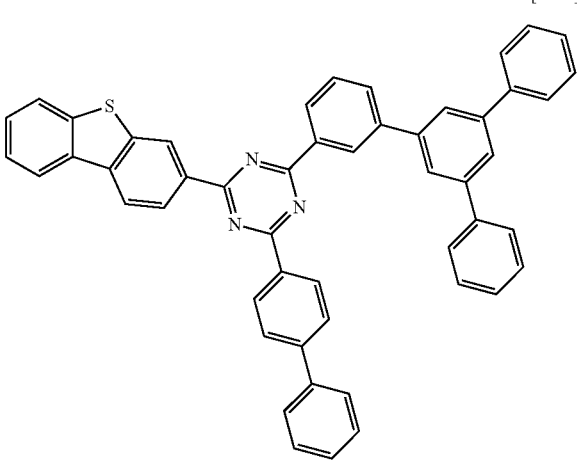
[B-46]
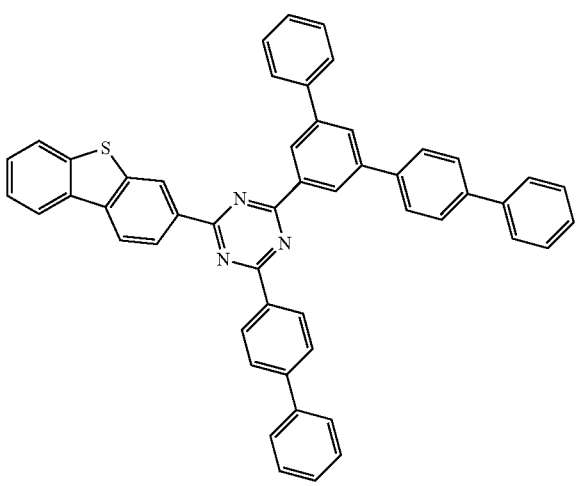

[B-47]
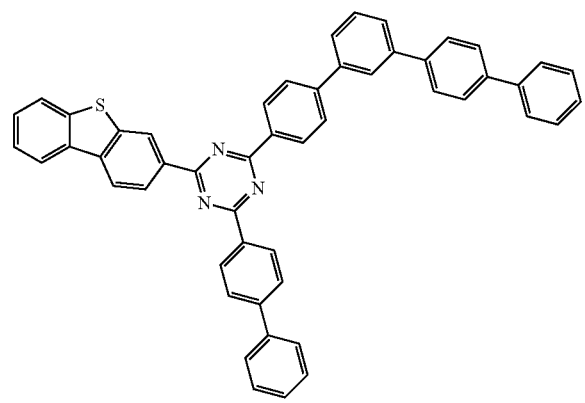
[B-48]
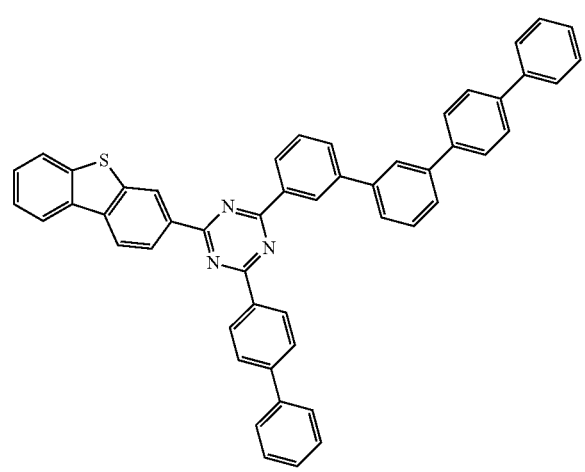
[B-49]
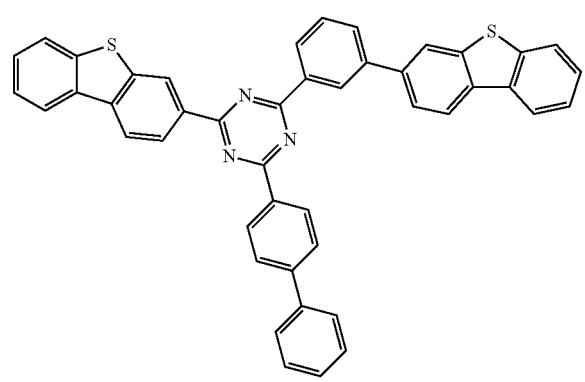
[B-50]
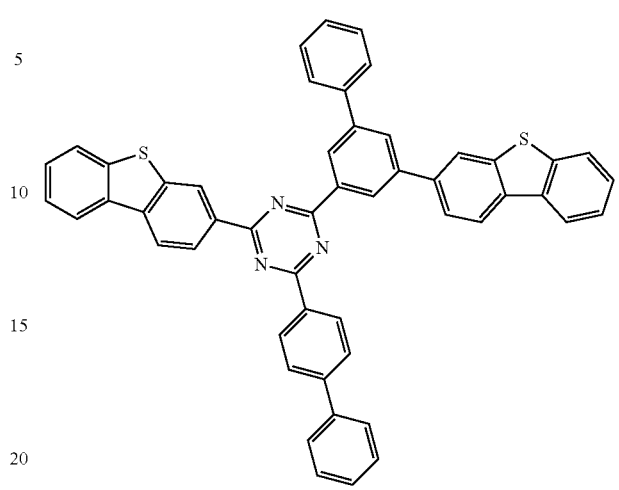
[B-51]
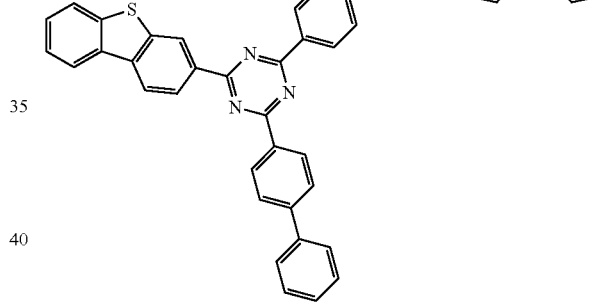
[B-52]
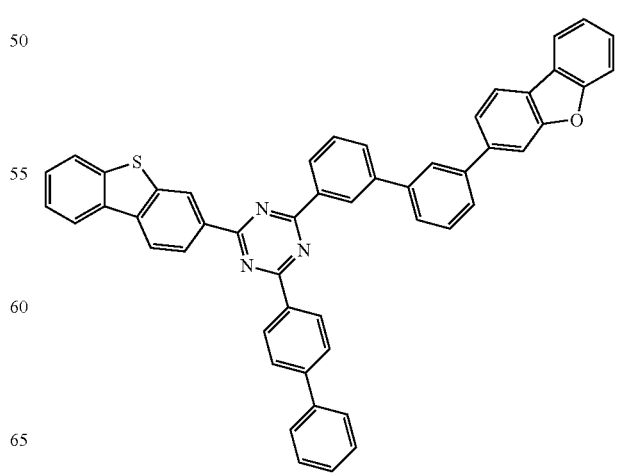

[B-53]
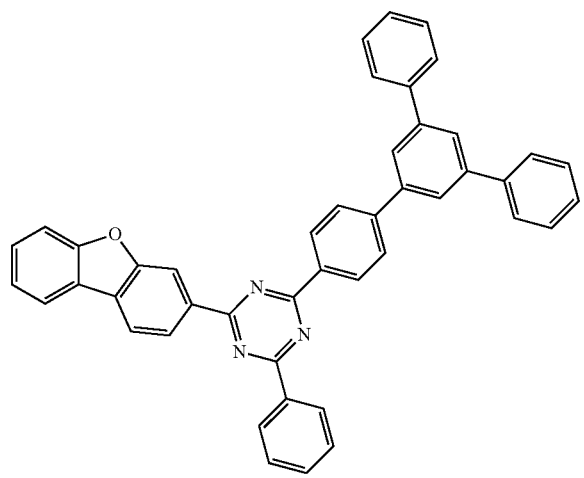
[B-54]
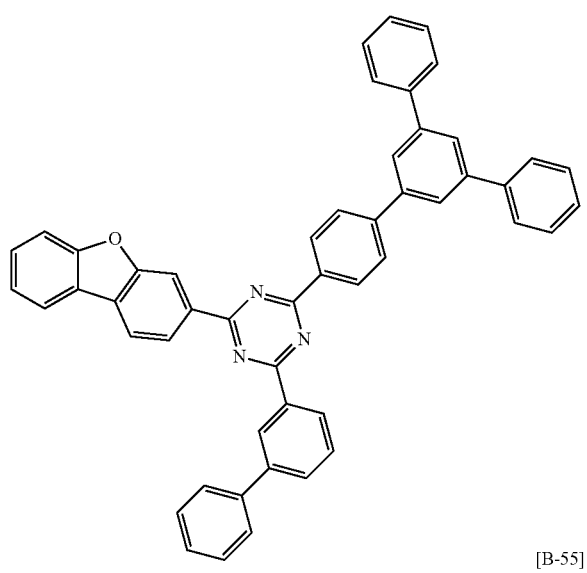
[B-55]
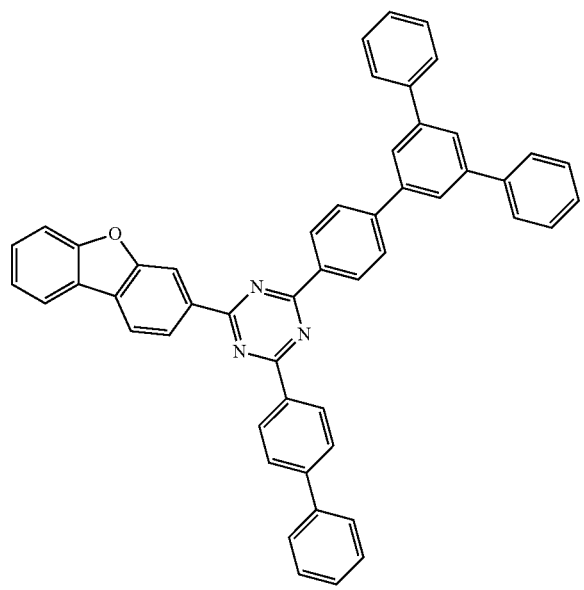
[B-56]
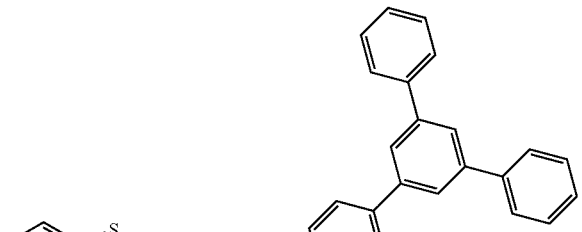
[B-57]
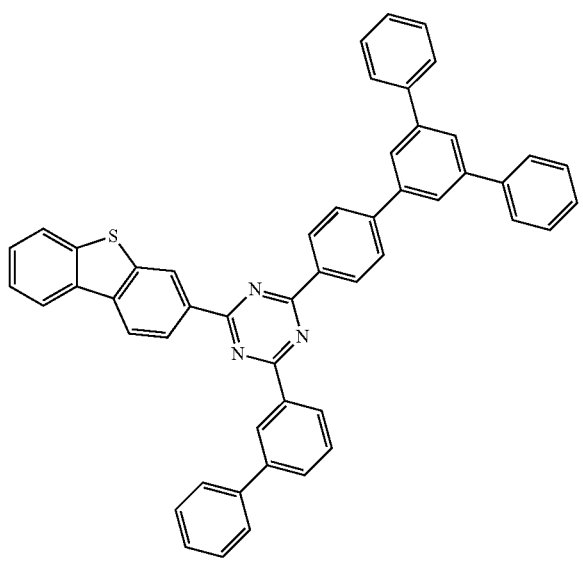
[B-58]
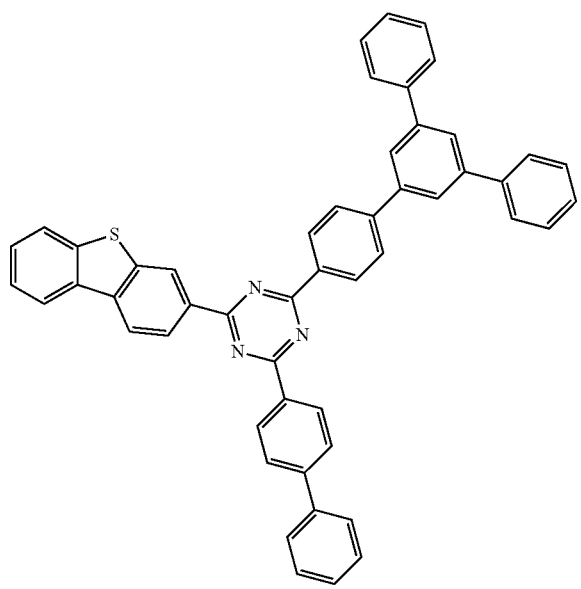

[B-59]
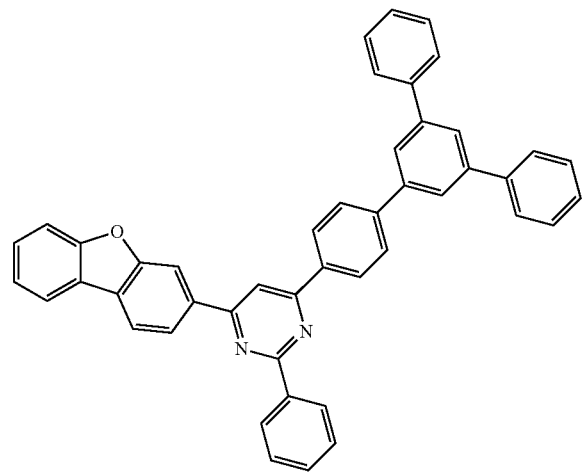
[B-60]
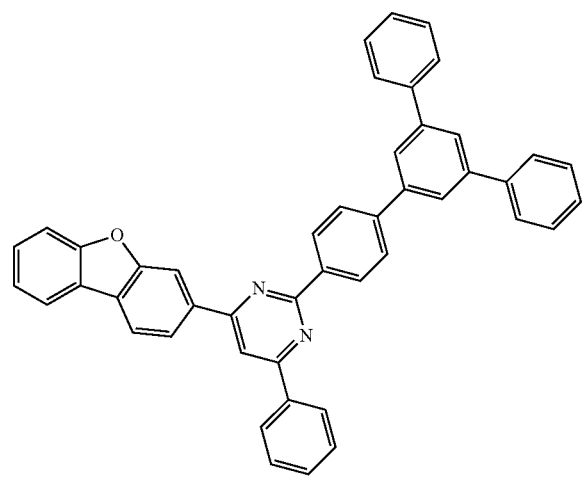
[B-61]
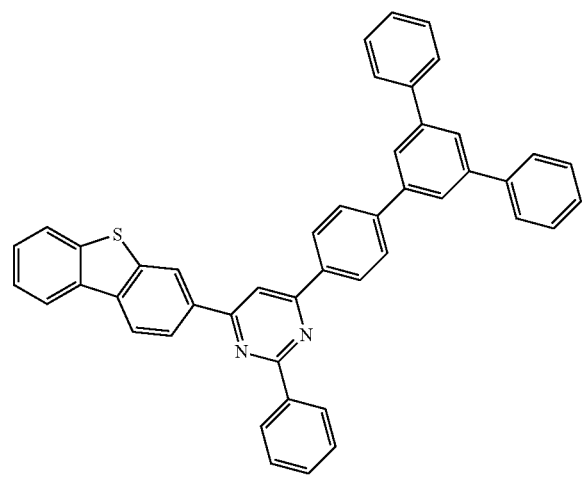
[B-62]
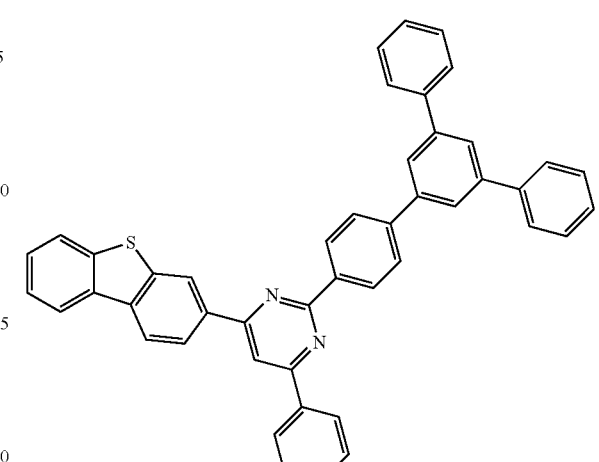
[B-63]
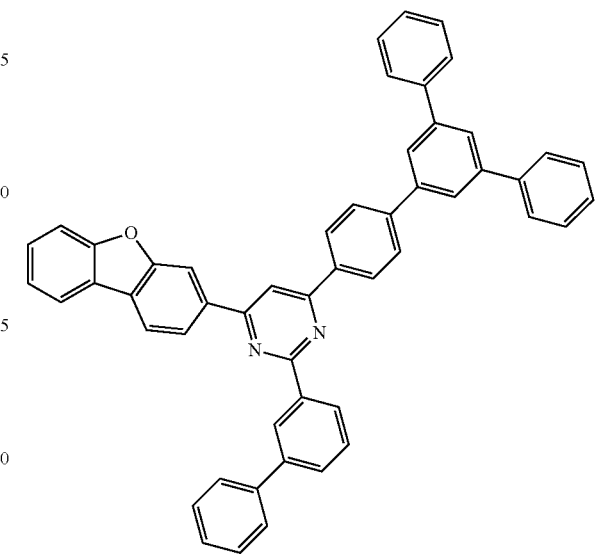
[B-64]
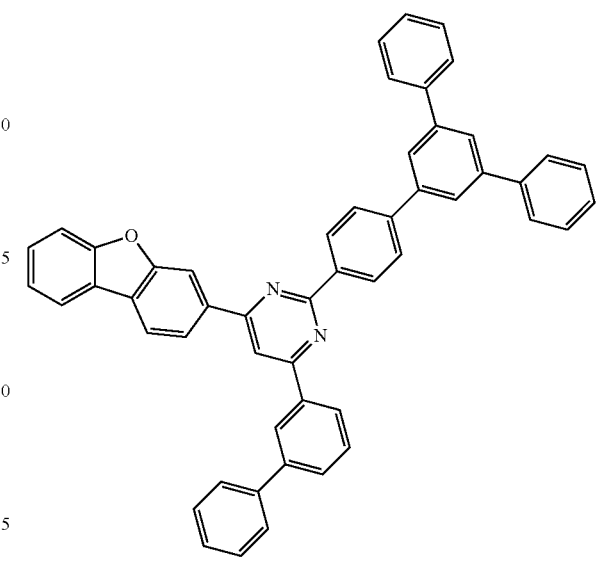

[B-65]
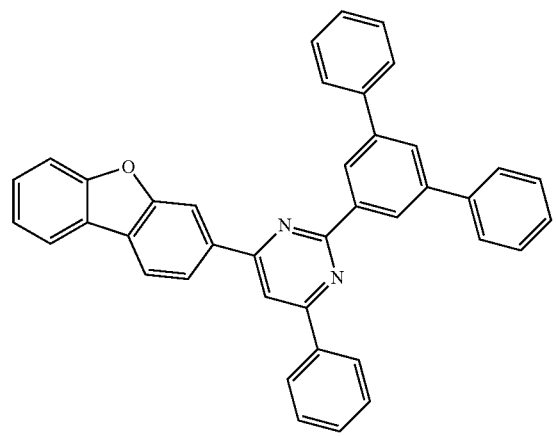
[B-66]
[B-67]
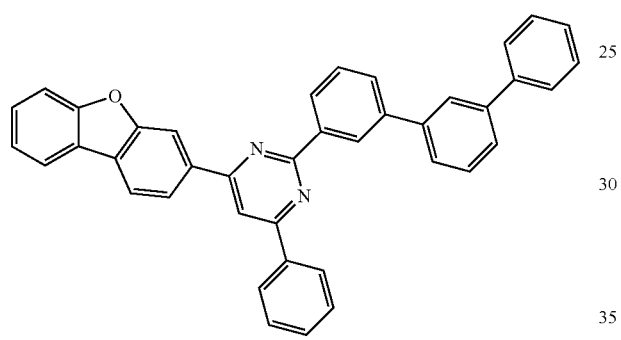
[B-68]
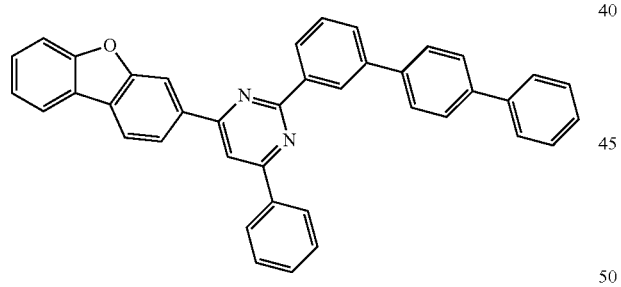
[B-69]
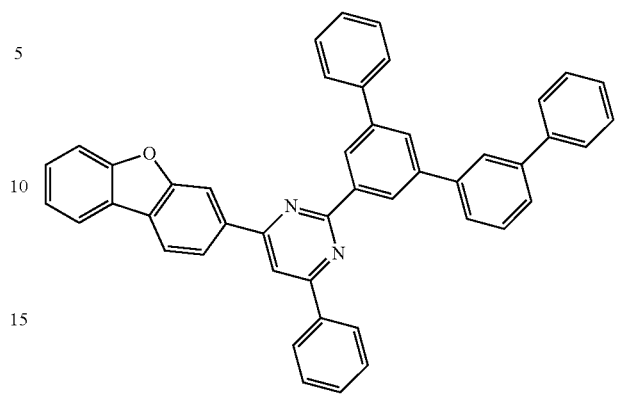
[B-70]
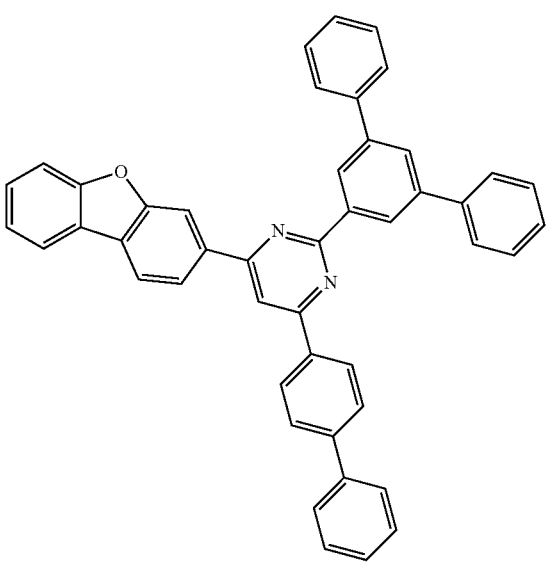
[B-71]
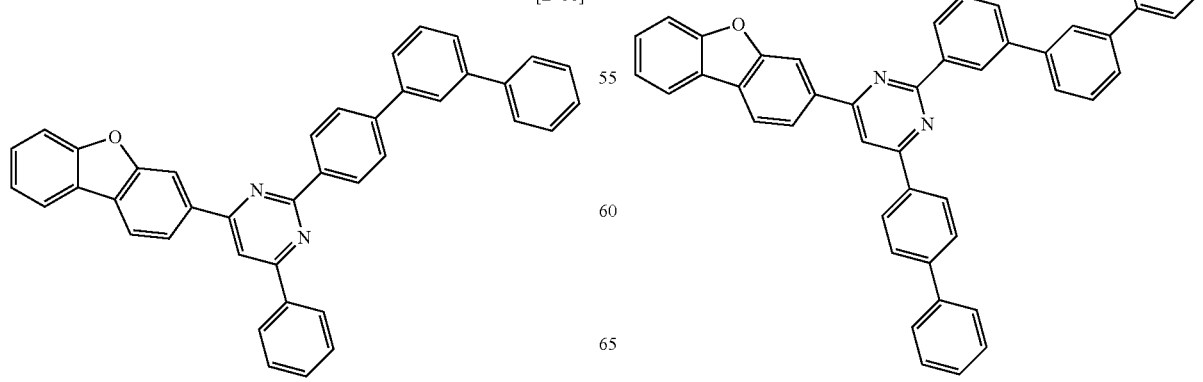

[B-72]
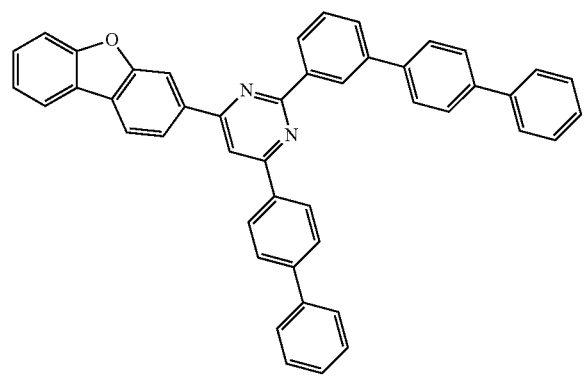
[B-73]
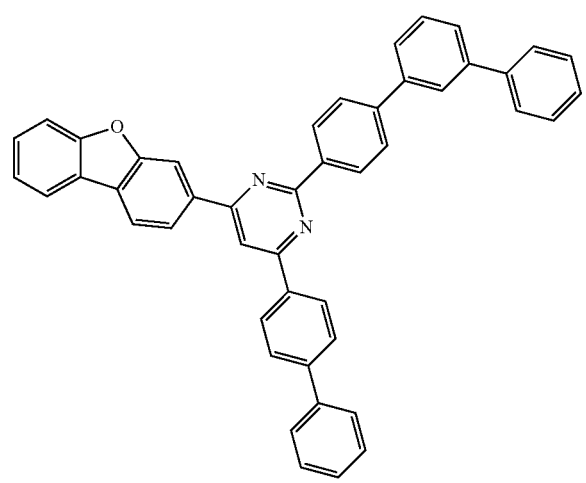
[B-74]
[B-75]
[B-76]
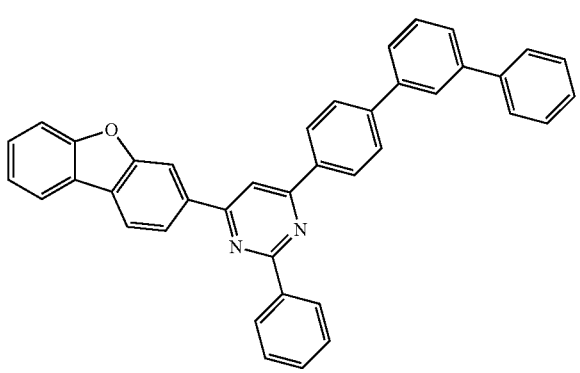
[B-77]
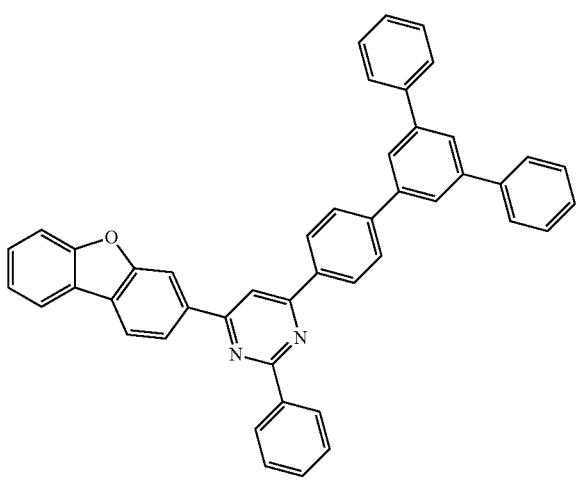
[B-78]
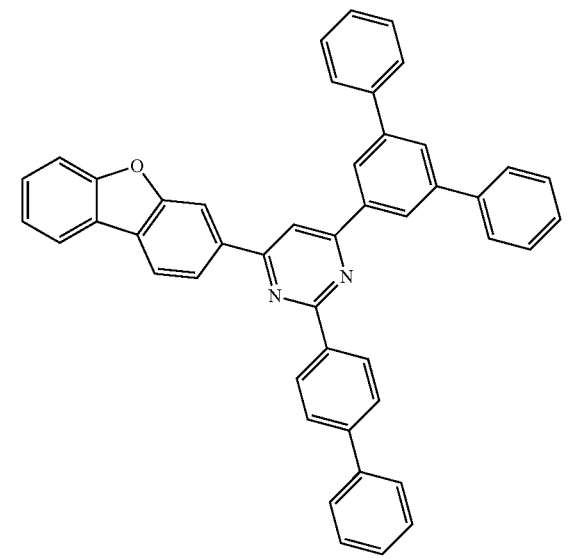

-continued

[B-79]

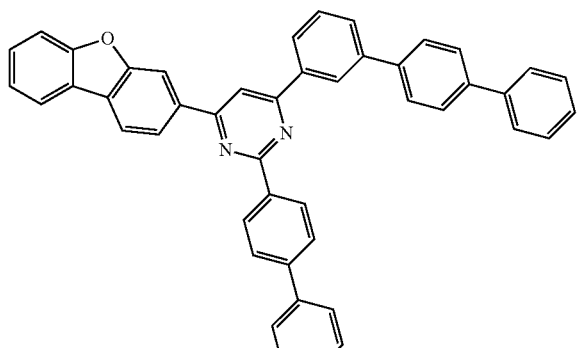

[B-80]

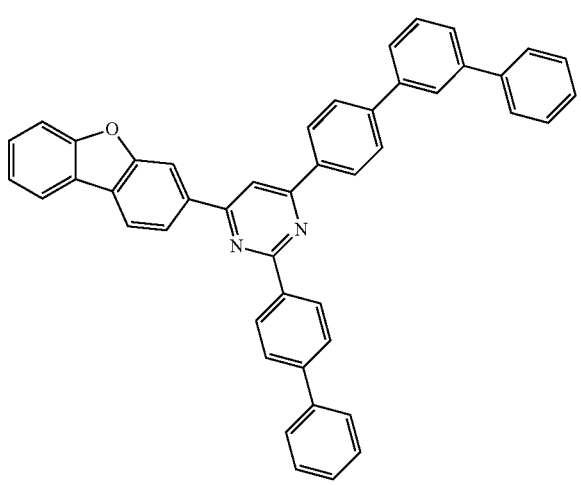

[B-81]

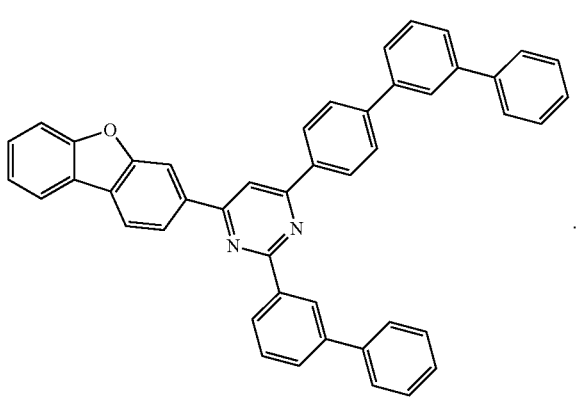

The first compound for an organic optoelectronic device may be applied to an organic optoelectronic device alone or with other compounds for an organic optoelectronic device. When the compound for an organic optoelectronic device is used with other compounds for an organic optoelectronic device, they may be applied in a form of a composition.

Hereinafter, one example of a composition for an organic optoelectronic device including the first compound for an organic optoelectronic device is described.

A composition for an organic optoelectronic device according to another embodiment of the present invention includes the first compound for an organic optoelectronic device; and a second compound for an organic optoelectronic device represented by Chemical Formula 2.

[Chemical Formula 2]

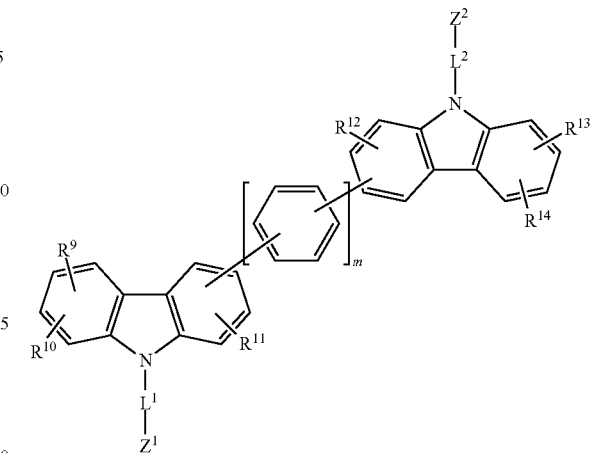

In Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^9$ to $R^{14}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group. In a specific example embodiment of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

In an example embodiment of the present invention, $L^1$ and $L^2$ of Chemical Formula 2 may independently be a single bond, or a substituted or unsubstituted C6 to C18 arylene group.

In an example embodiment of the present invention, $Z^1$ and $Z^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted triazinyl group, a substituted or unsubstituted quinolinyl group, a substituted or unsubstituted isoquinolinyl group, a substituted or unsubstituted carbazolyl group, a substituted or unsubstituted fluorenyl group, or a combination thereof.

Specifically, $Z^1$ and $Z^2$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted pyridinyl group, a substituted or unsubstituted pyrimidinyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof, and may be for example a phenyl group, a biphenyl group, a dibenzofuranyl group, or a dibenzothiophenyl group.

In an example embodiment of the present invention, $R^9$ to $R^{14}$ of Chemical Formula 2 may independently be hydrogen, deuterium, or a substituted or unsubstituted C6 to C12 aryl group.

In an example embodiment of the present invention, m of Chemical Formula 2 may be 0 or 1.

In a specific example embodiment of the present invention, Chemical Formula 2 may be one of structures of Group I and *-L$^1$-Z$^1$ and *-L$^2$-Z$^2$ may be one of substituents of Group II.

[Group I]

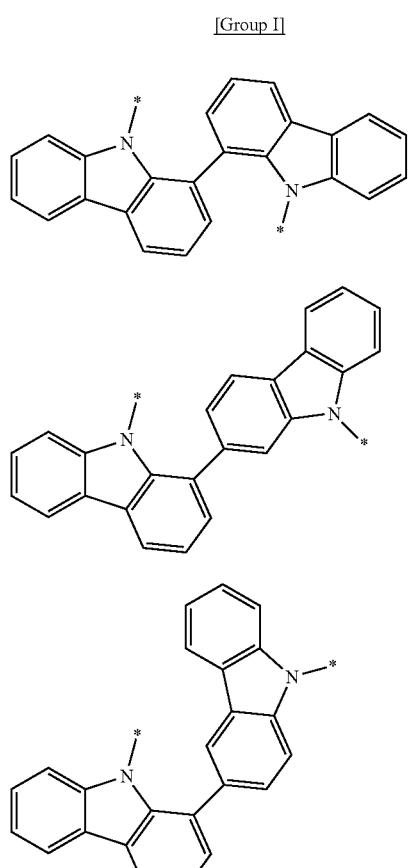

C-1

C-2

C-3

C-4

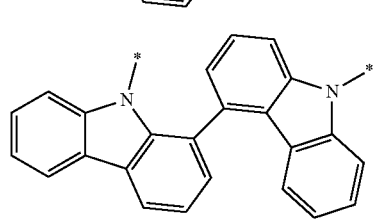

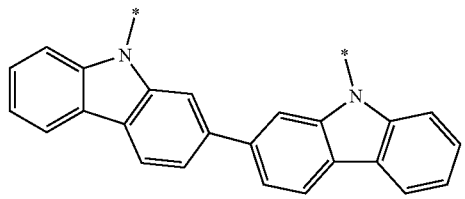

C-5

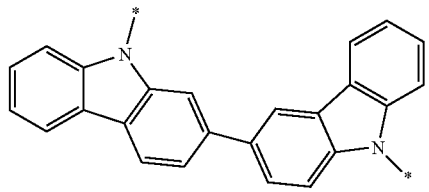

C-6

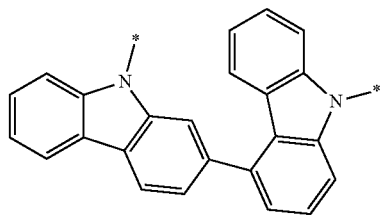

C-7

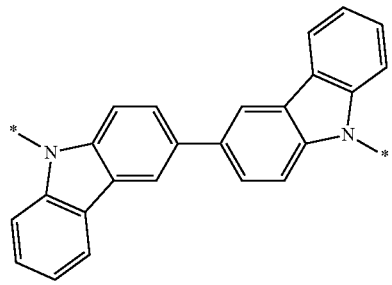

C-8

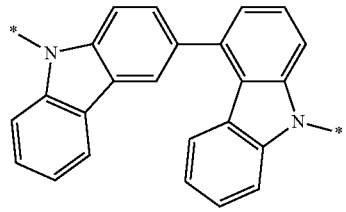

C-9

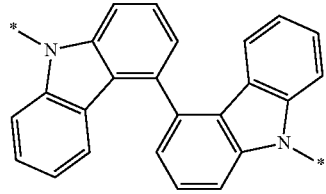

C-10

-continued
C-11
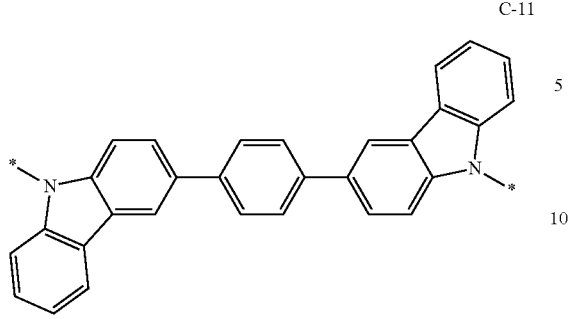
C-12
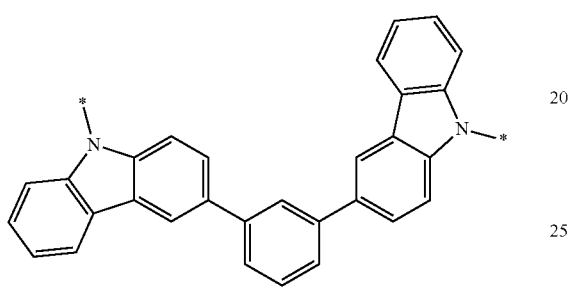
C-13
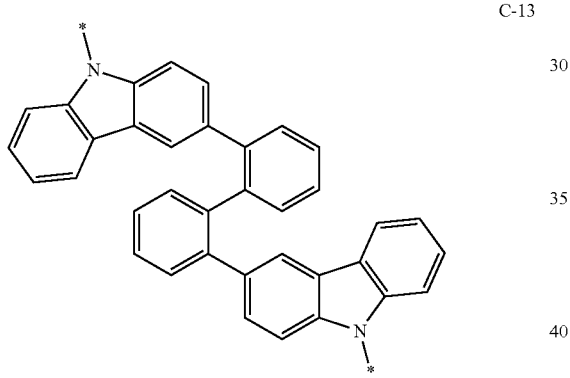
C-14
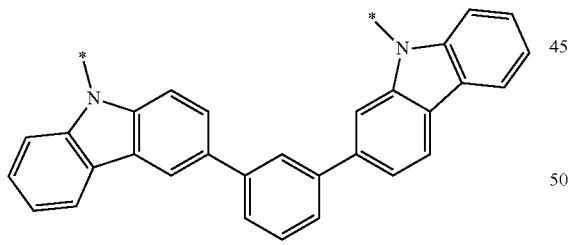
C-15
-continued
C-16
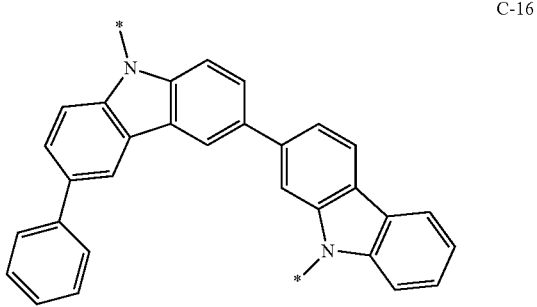
C-17
C-18
[Group II]
B-1
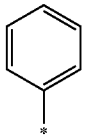
B-2
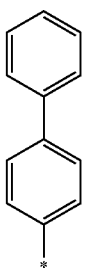

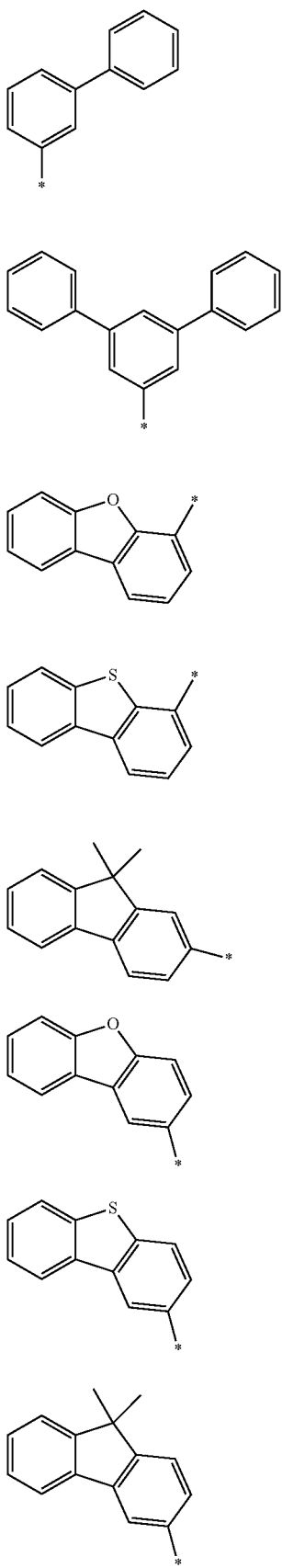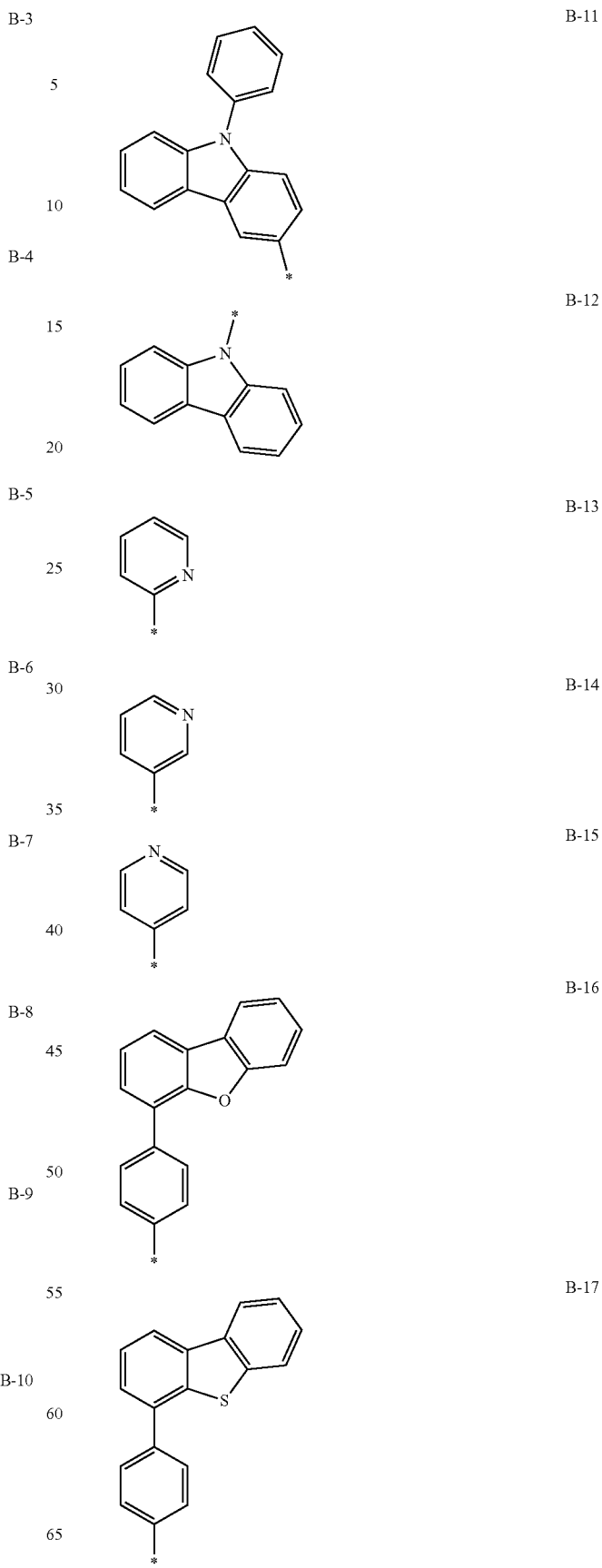

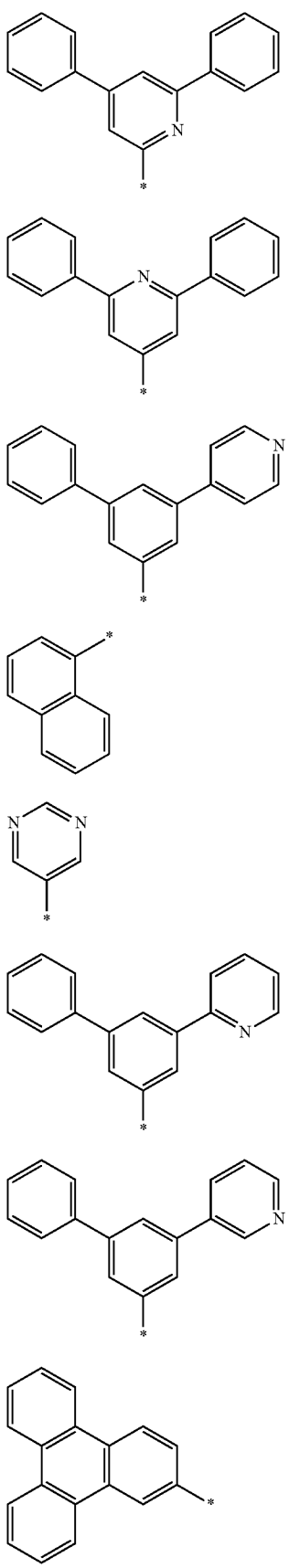
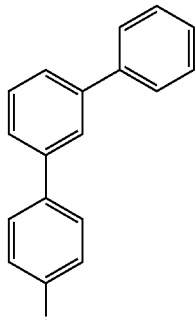
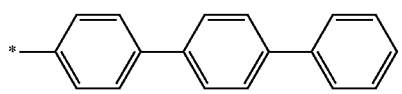
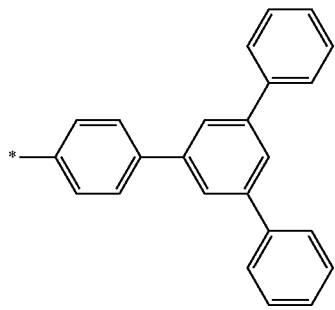
In Groups I and II, * is a linking point.
The second compound for an organic optoelectronic device represented by Chemical Formula 2 may be for example selected from compounds of Group 2.
[Group 2]
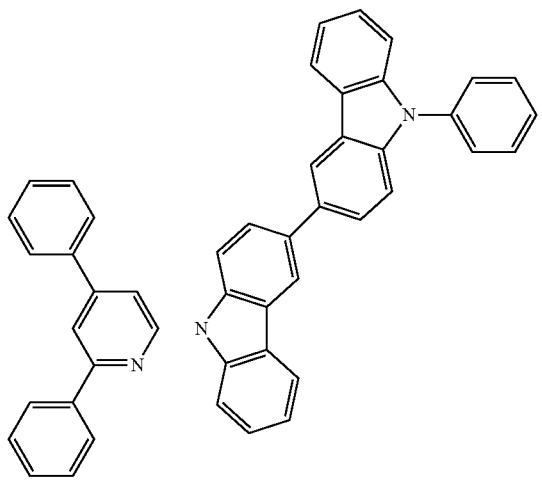

[E-2]
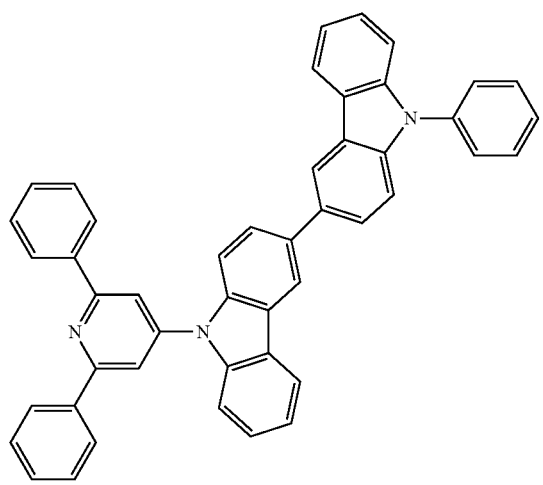
[E-3]
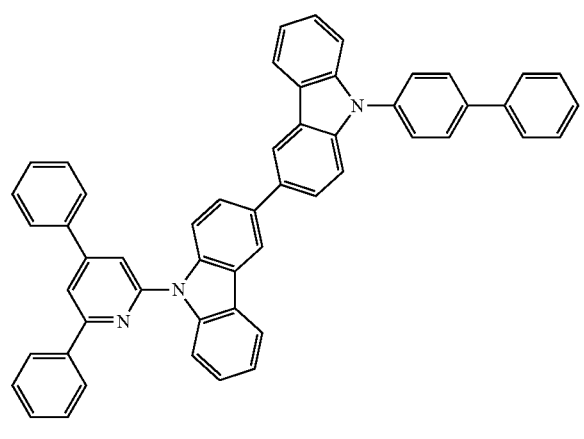
[E-4]
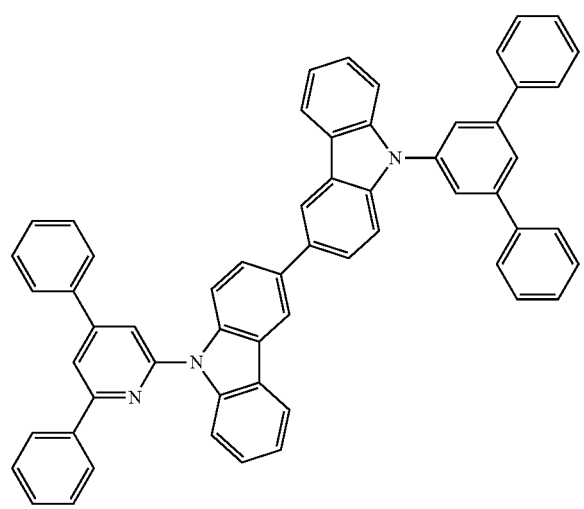
[E-5]
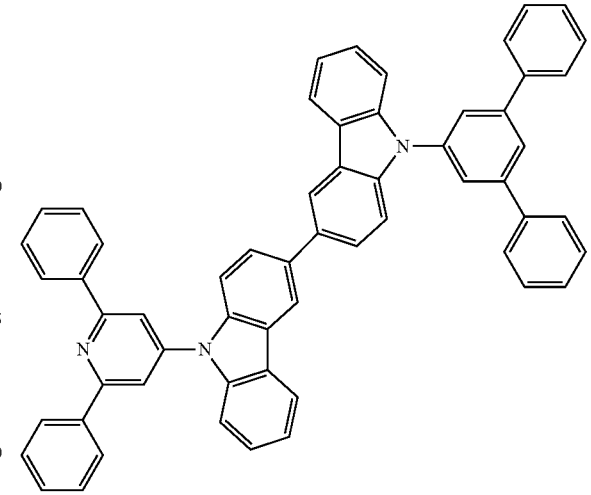
[E-6]
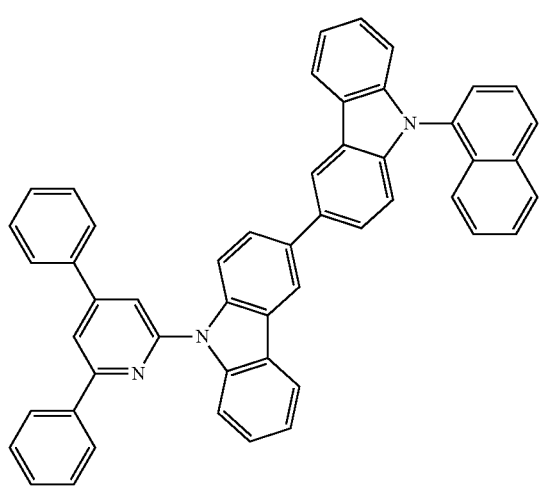
[E-7]
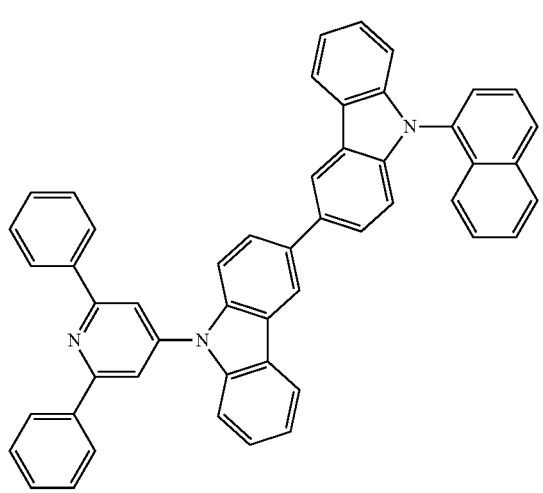

[E-8]
[E-9]
[E-10]
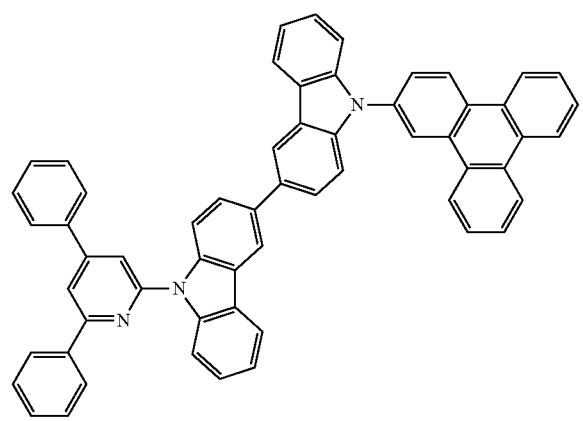
[E-11]
[E-12]
[E-13]
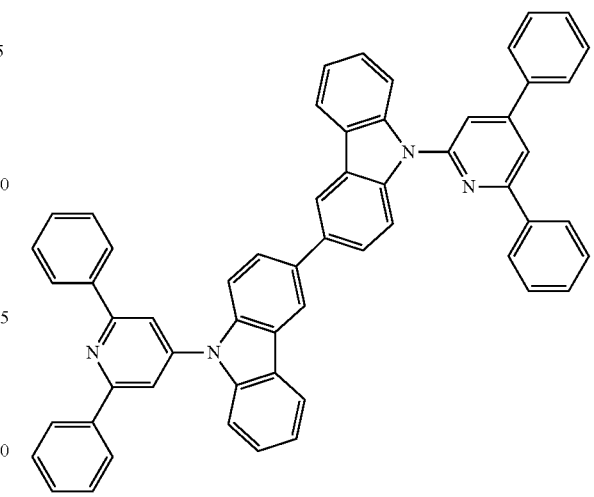
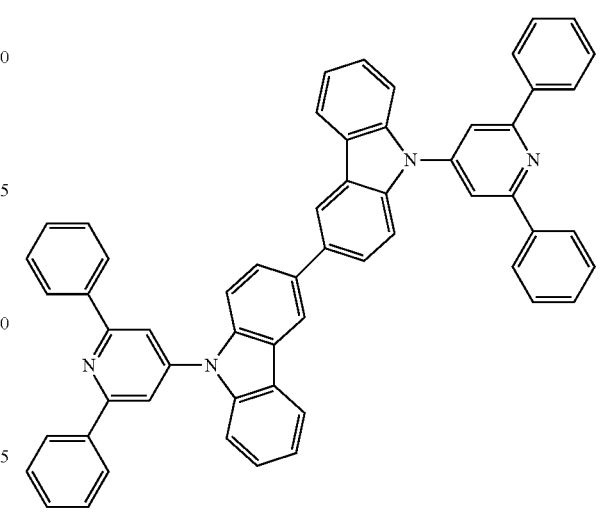
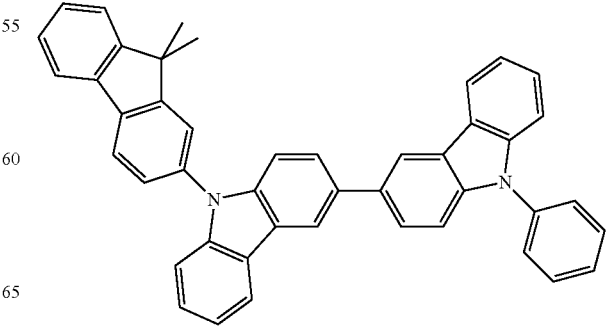

[E-14]
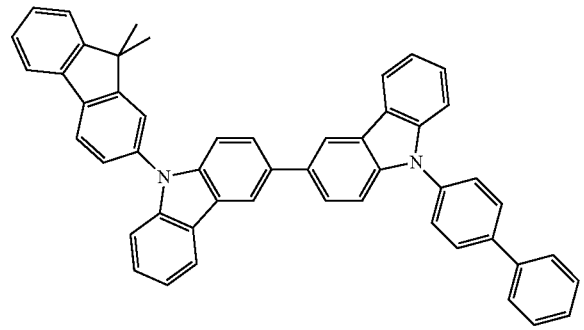
[E-15]
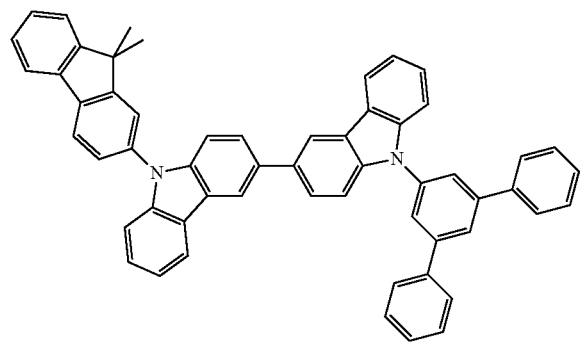
[E-16]
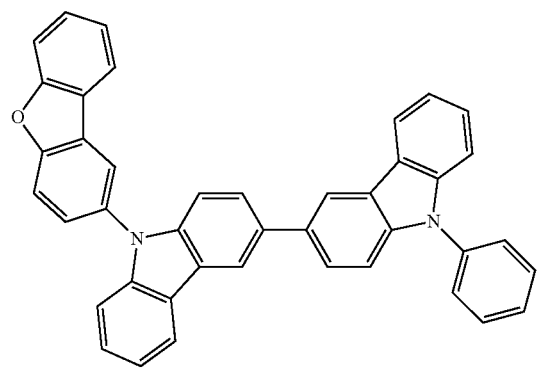
[E-17]
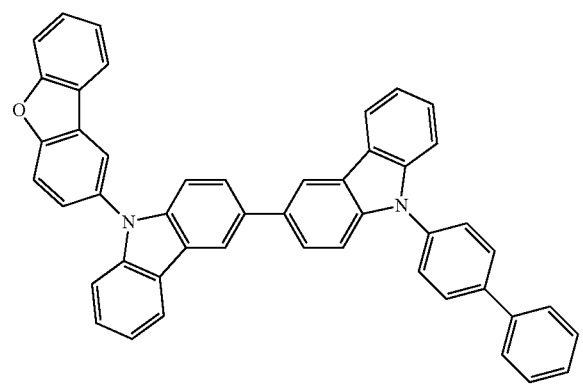
[E-18]
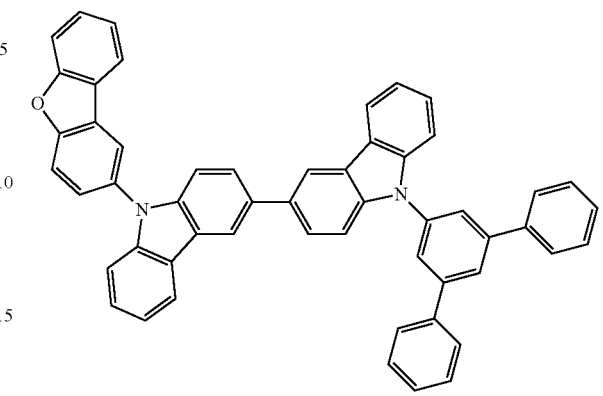
[E-19]
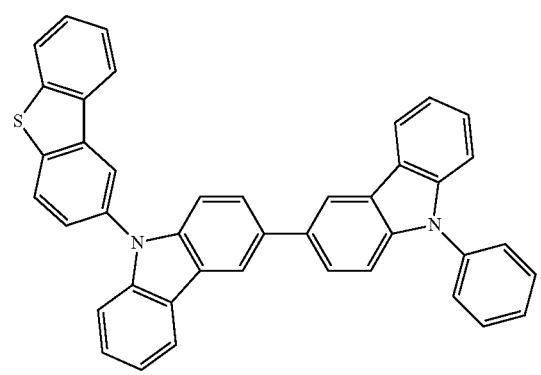
[E-20]
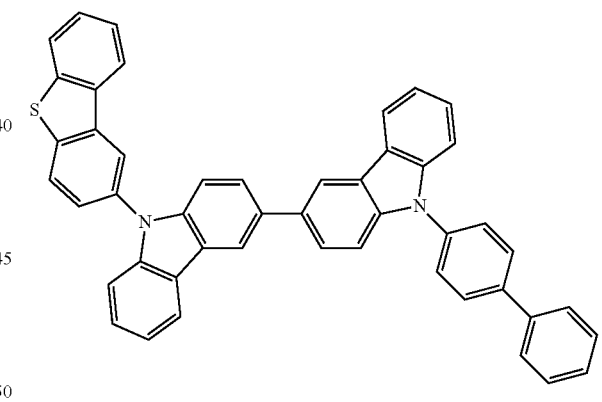
[E-21]
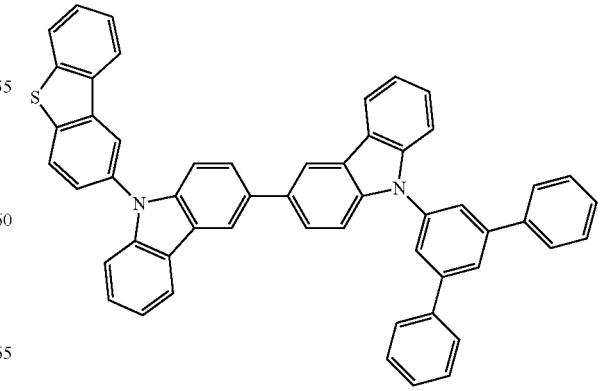

[E-22]
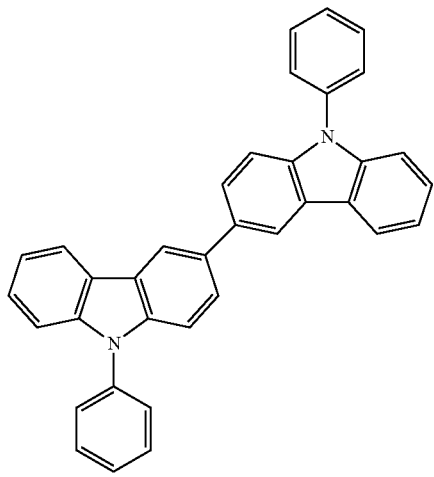
[E-23]
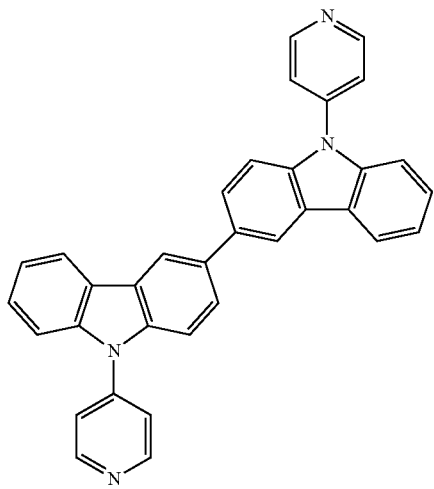
[E-24]
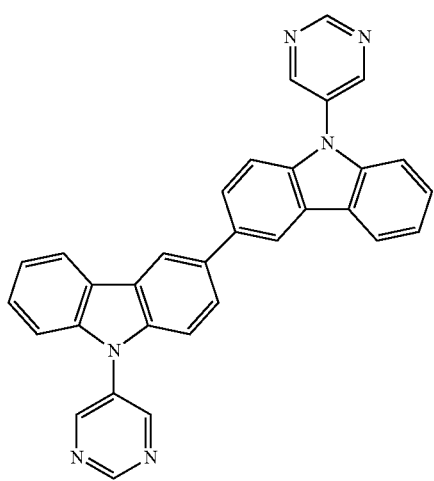
[E-25]
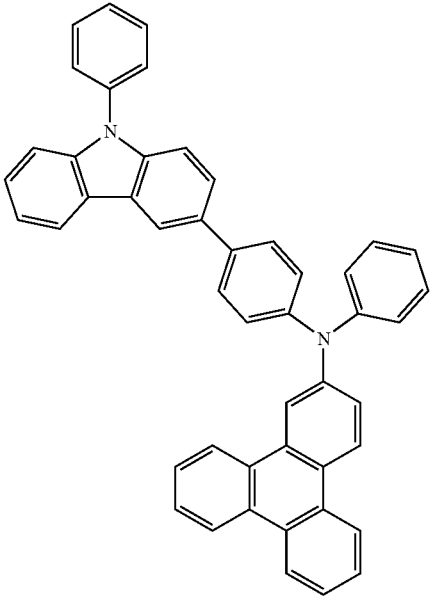
[E-26]
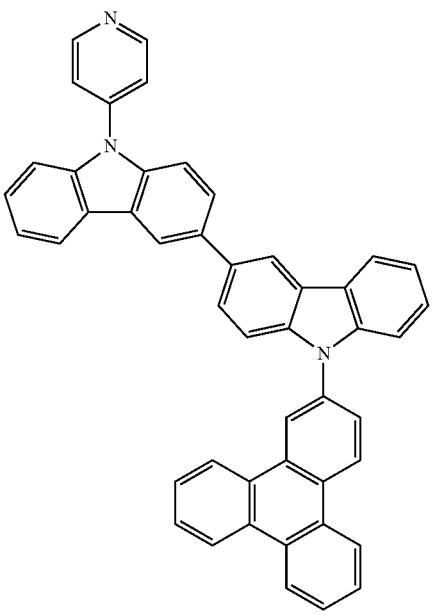

[E-27]
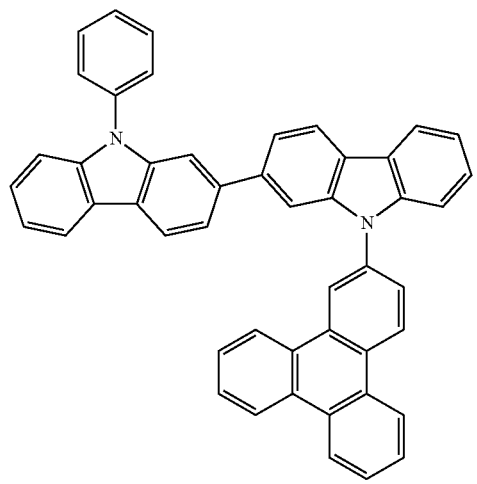
[E-28]
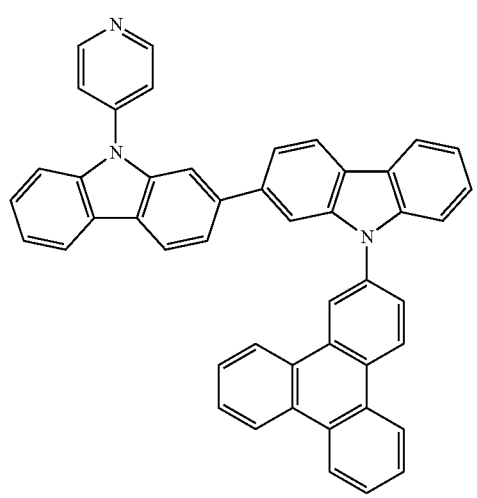
[E-29]
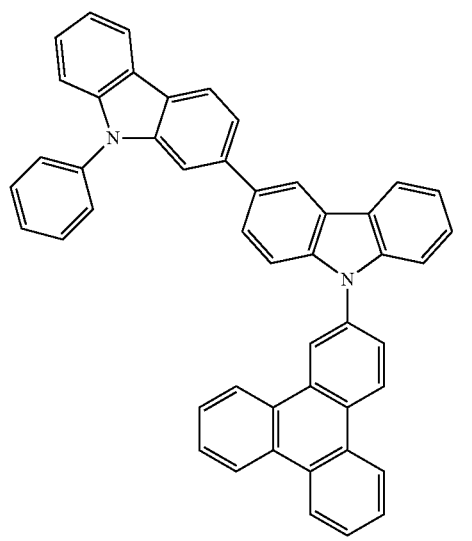
[E-30]
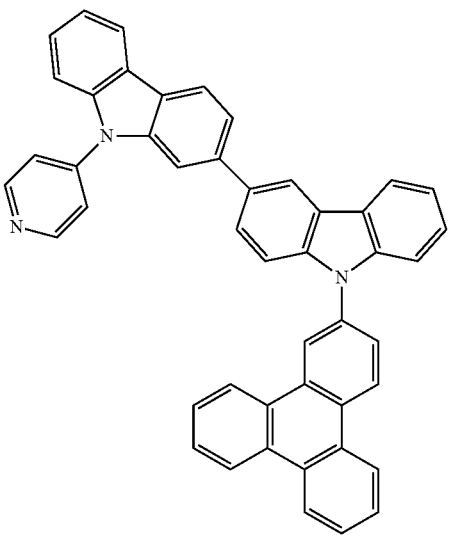
[E-31]
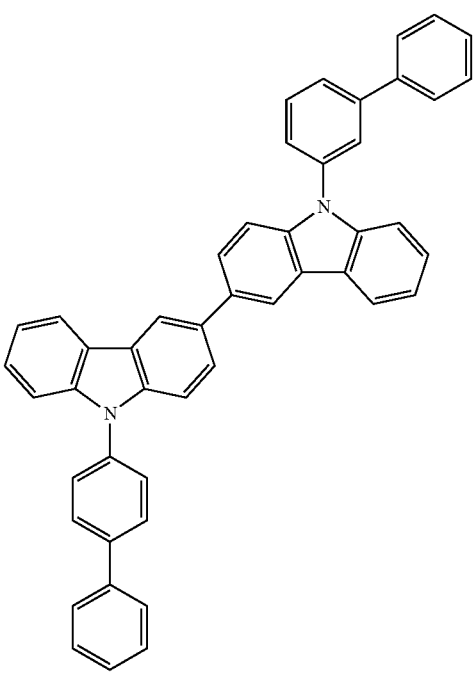

[E-32]
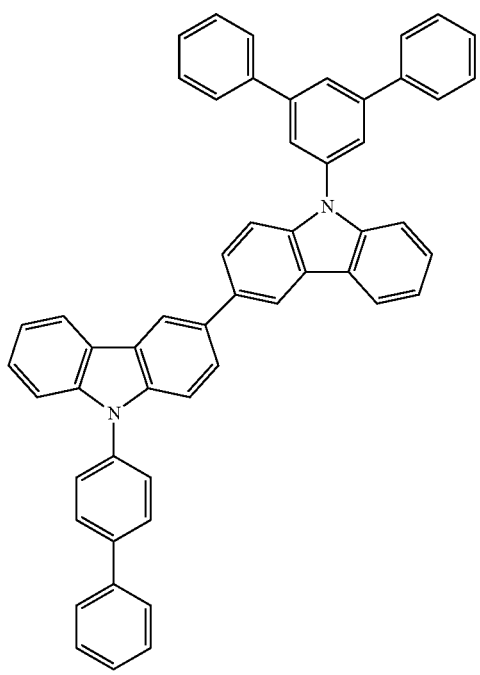
[E-34]
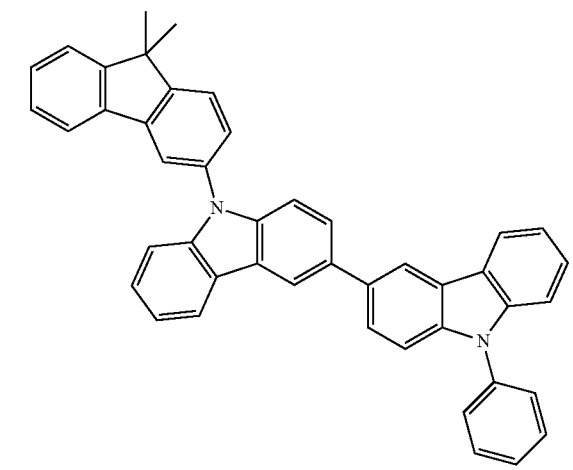
[E-35]
[E-33]
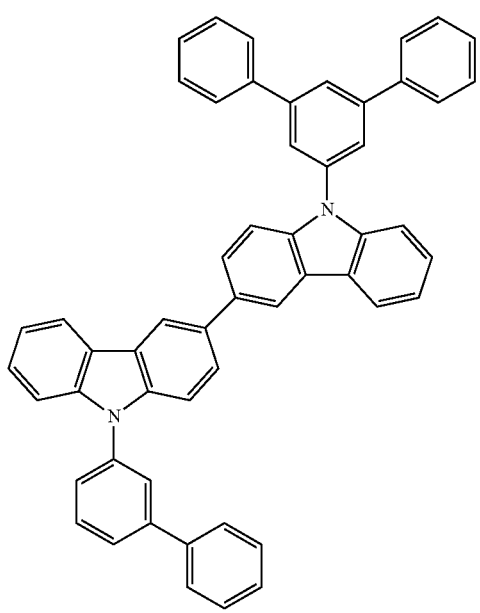
[E-36]
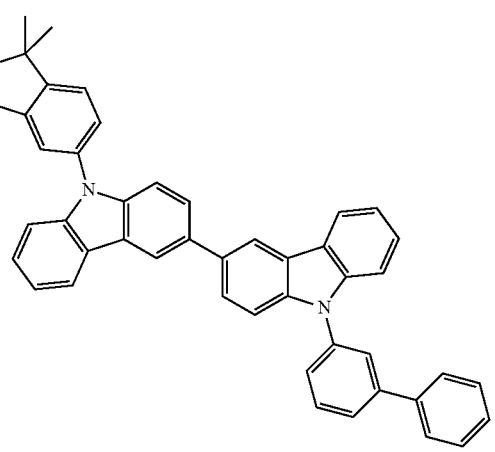

[E-37]
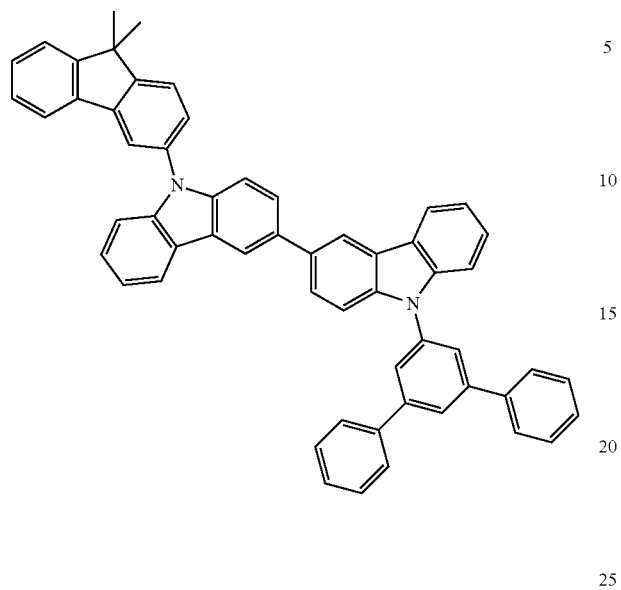
[E-40]
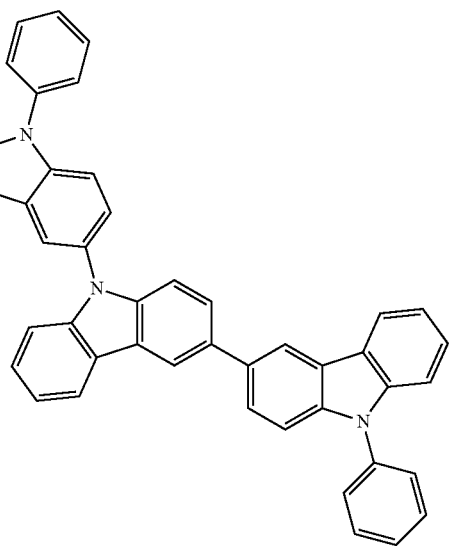
[E-38]
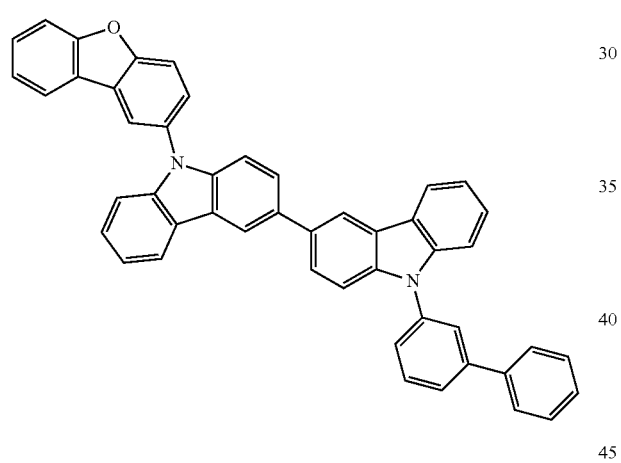
[E-41]
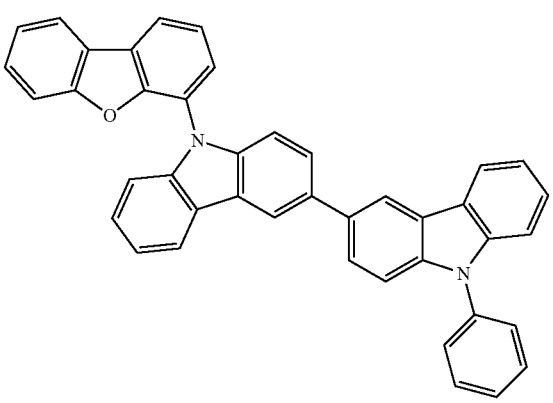
[E-39]
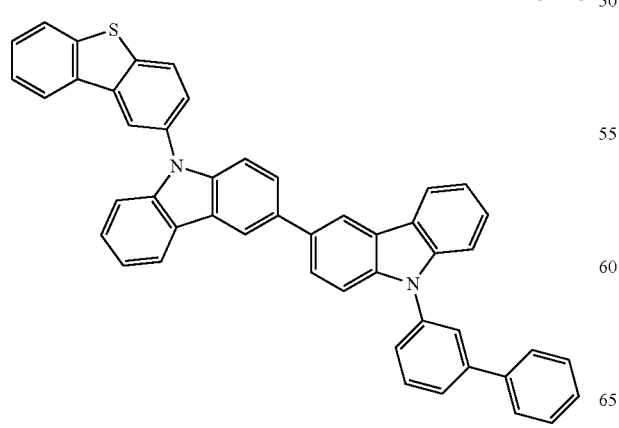
[E-42]
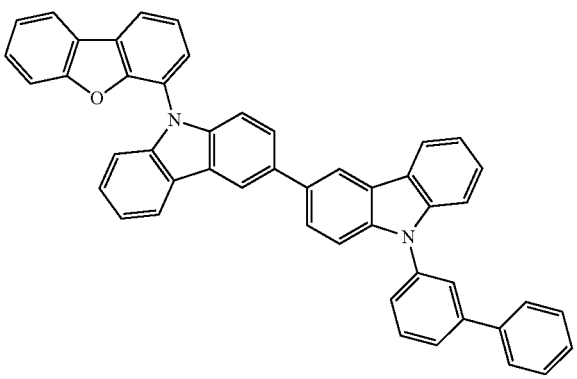

[E-43]
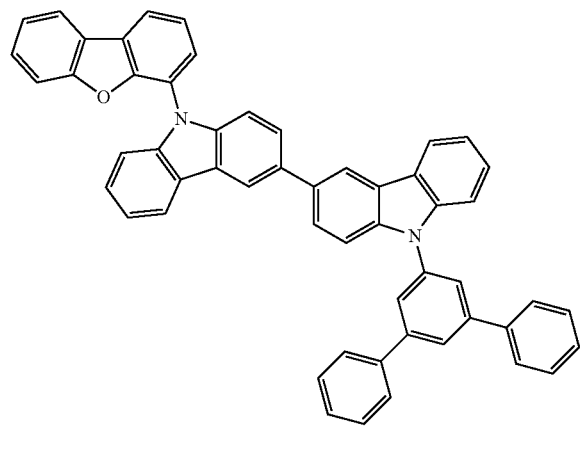
[E-44]
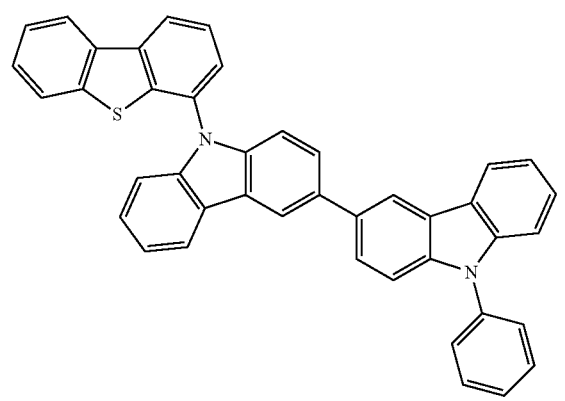
[E-46]
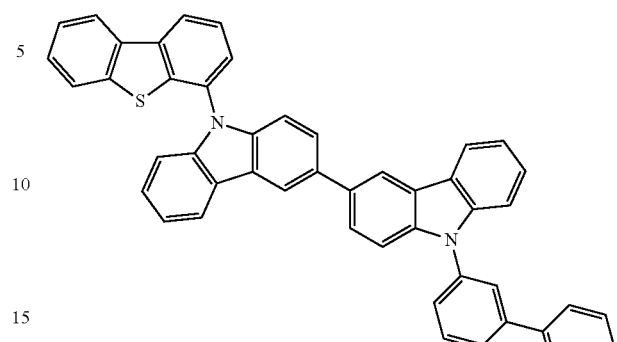
[E-47]
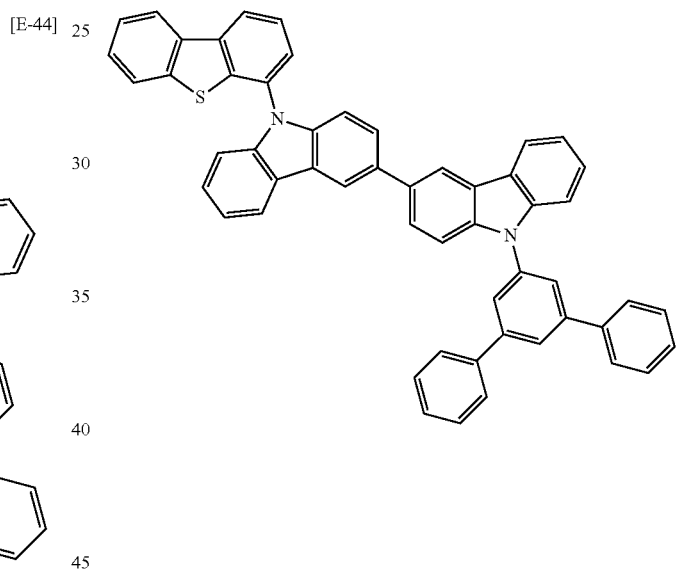
[E-45]
[E-48]
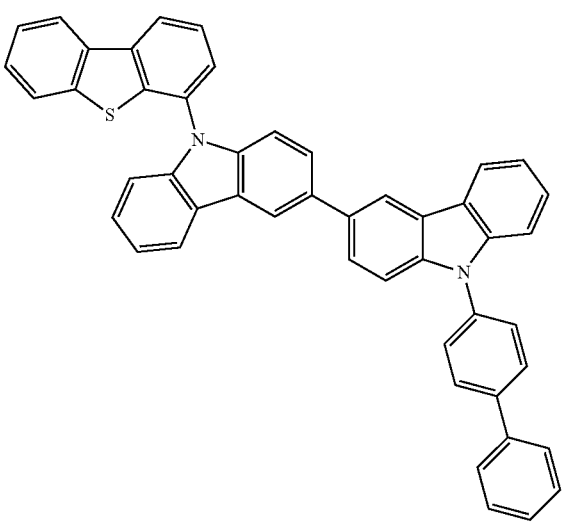

[E-49]
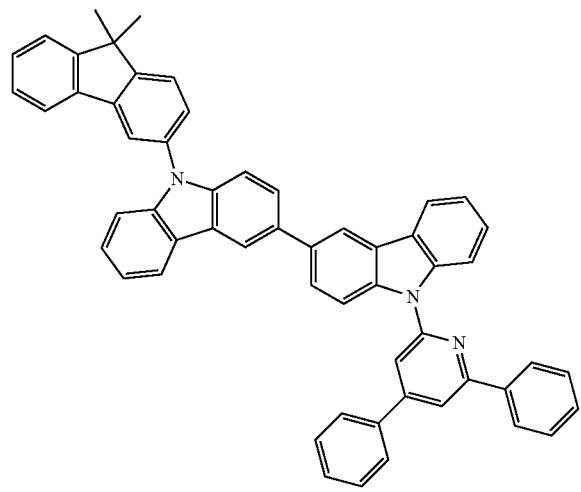
[E-52]
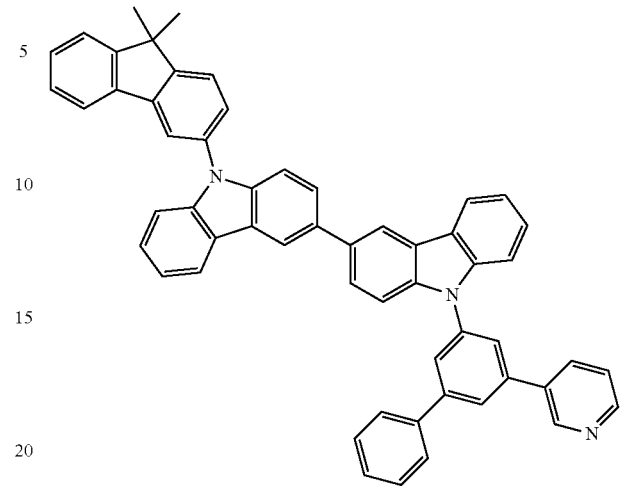
[E-50]
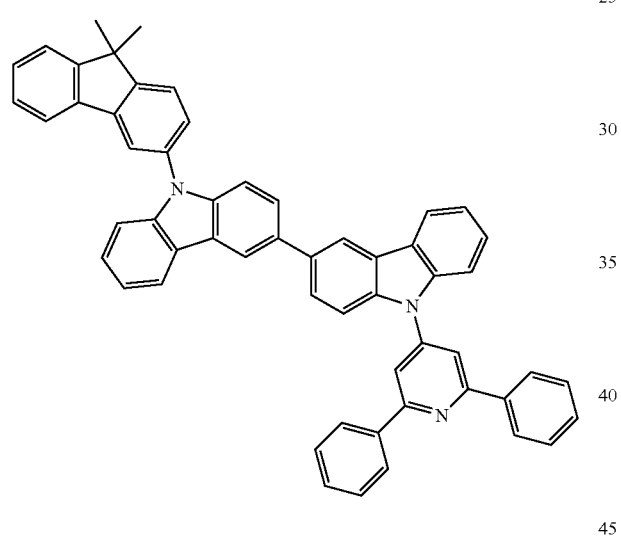
[E-53]
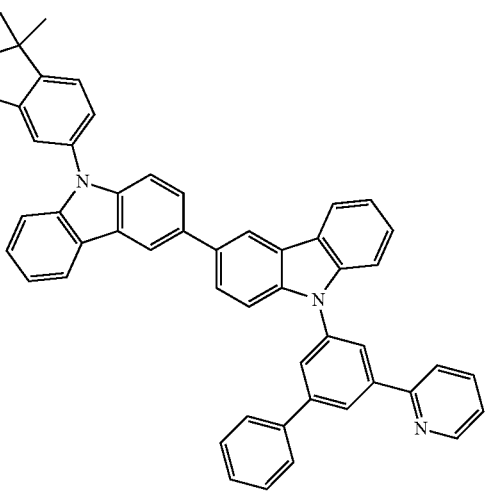
[E-51]
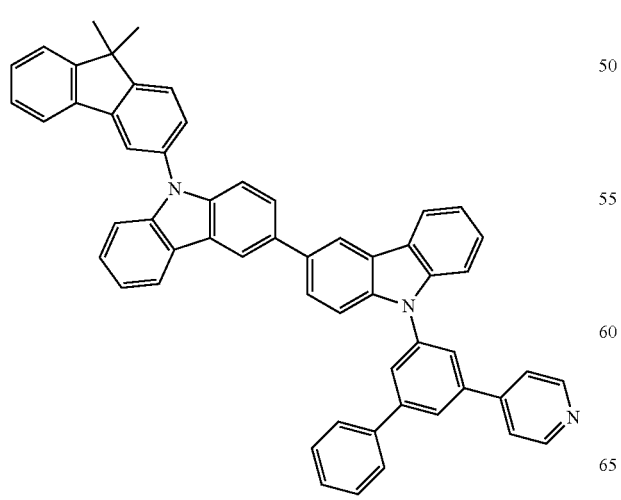
[E-54]
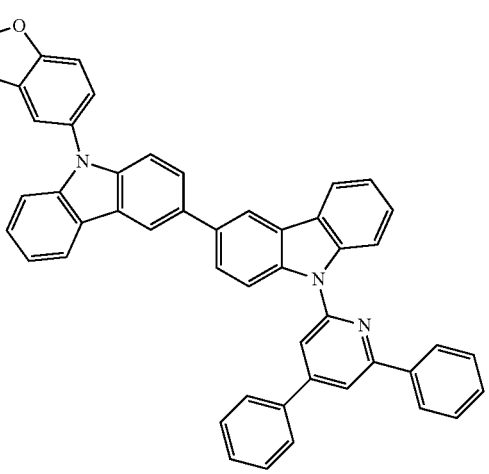

-continued
[E-55]
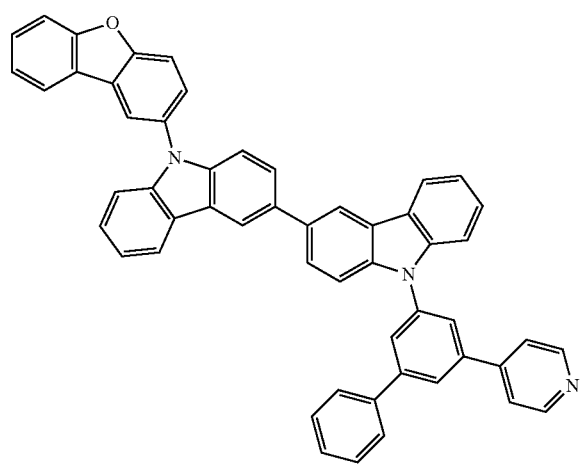
[E-58]
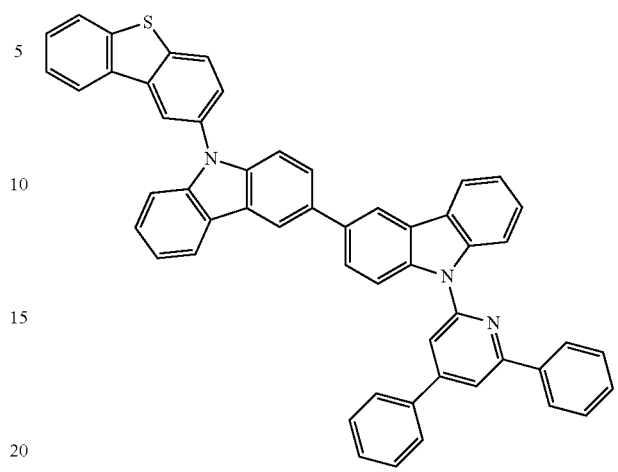
[E-56]
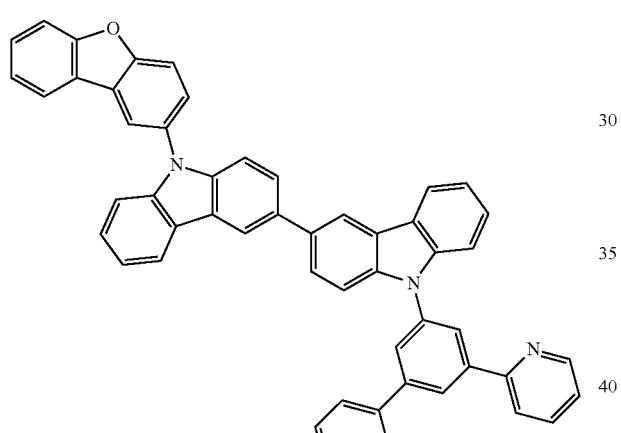
[E-59]
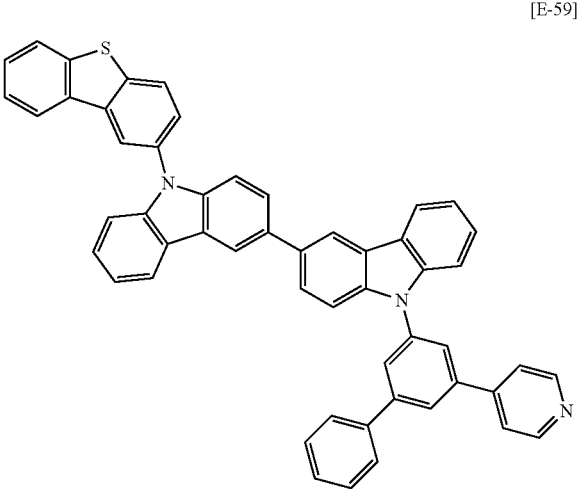
[E-57]
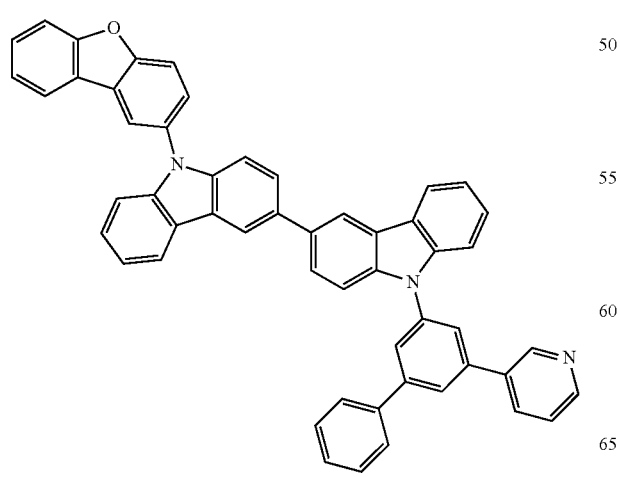
[E-60]
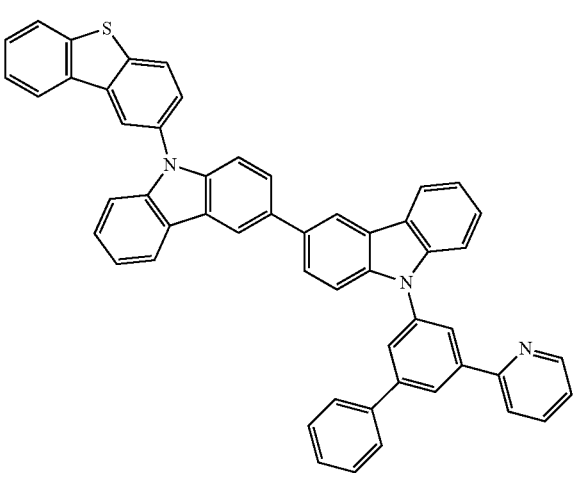

[E-61]
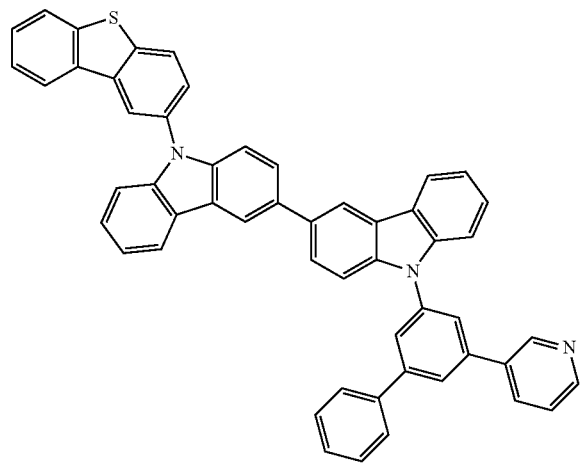
[E-62]
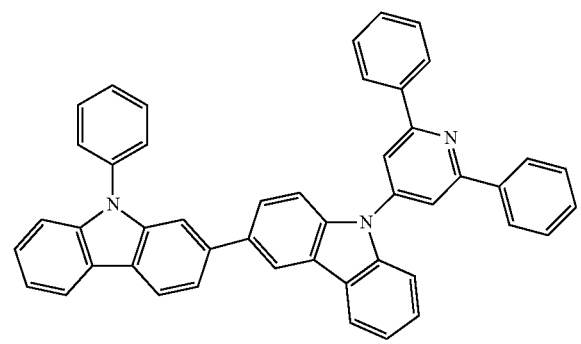
[E-63]
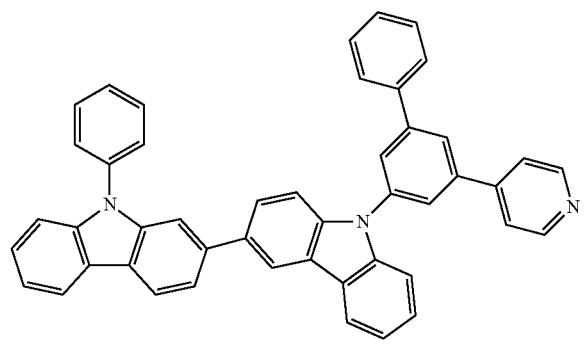
[E-64]
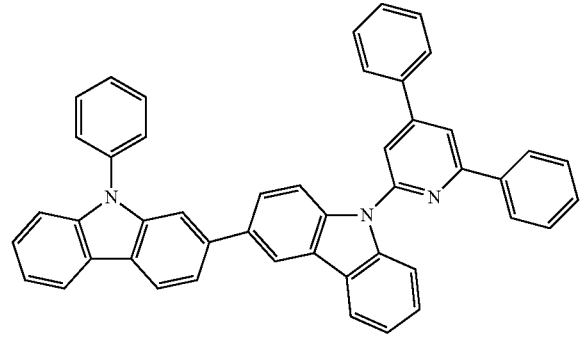
[E-65]
[E-66]
[E-67]
[E-68]
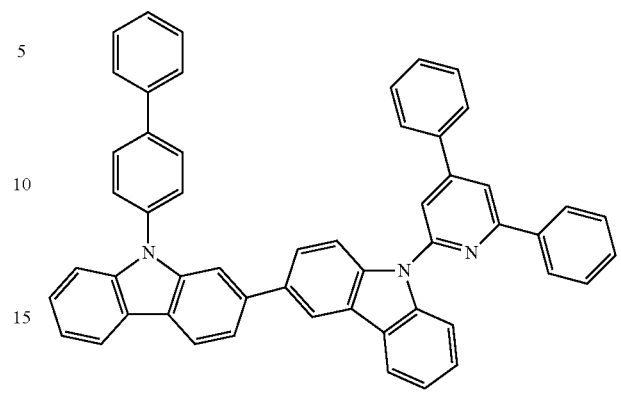

[E-69] 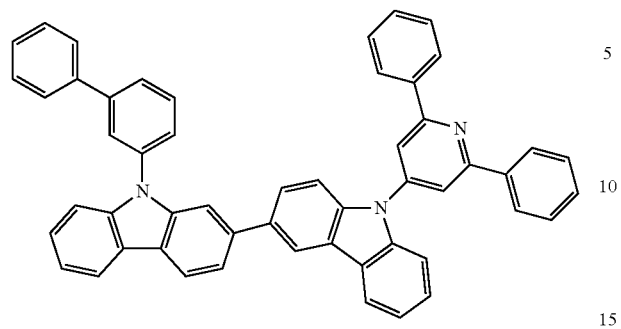
[E-73] 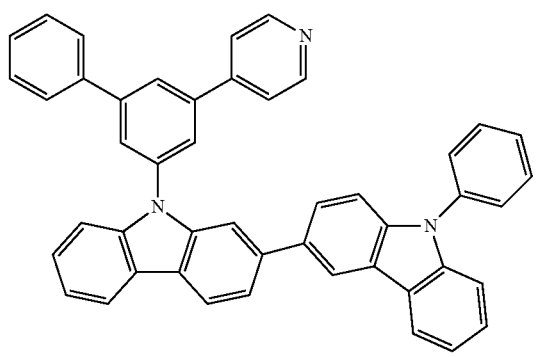
[E-70] 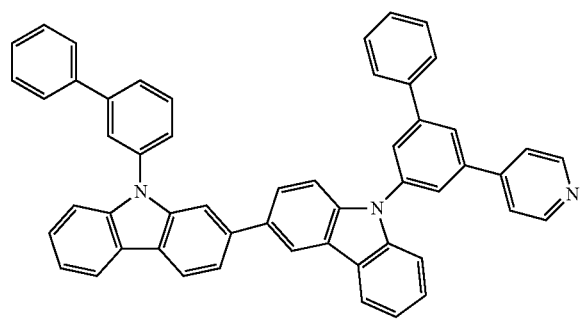
[E-74] 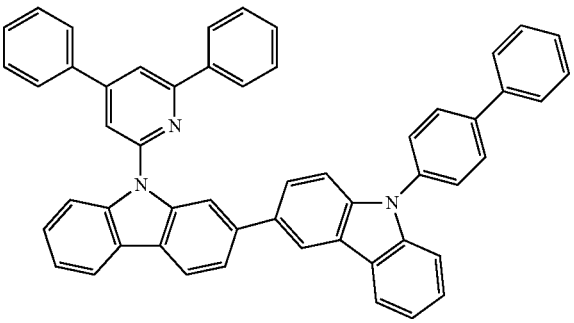
[E-71] 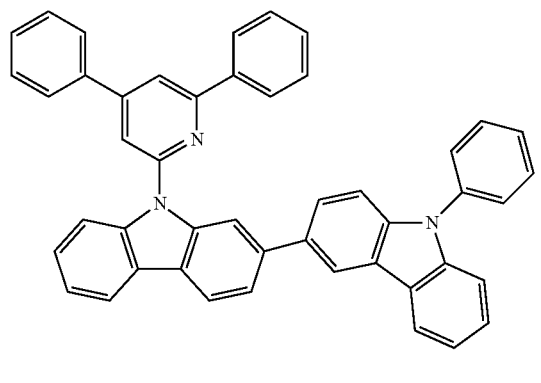
[E-75] 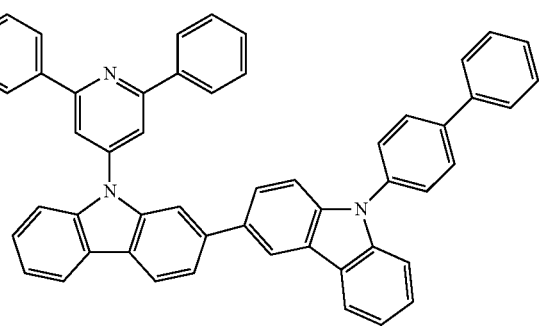
[E-72] 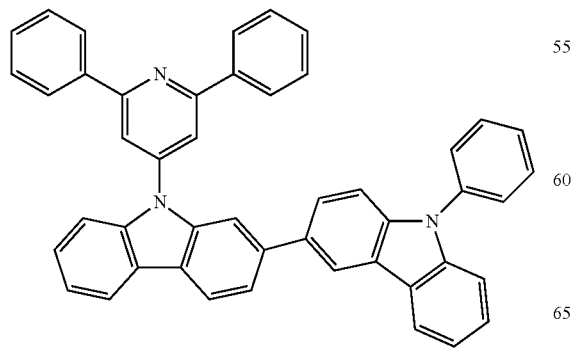
[E-76] 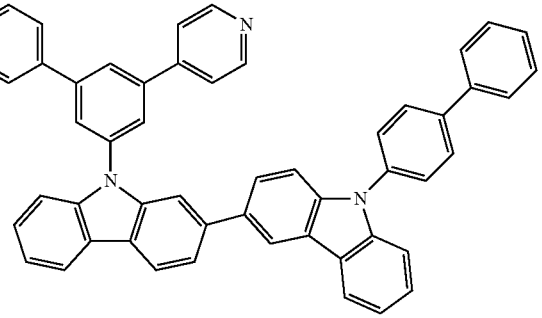

[E-77]
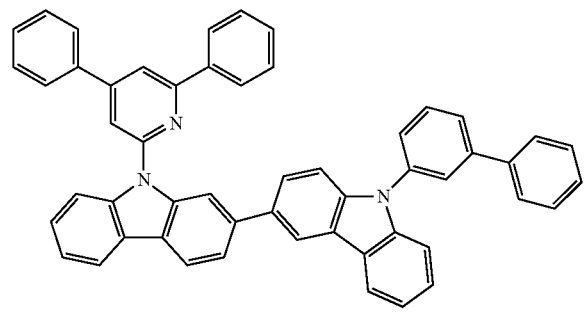
[E-81]
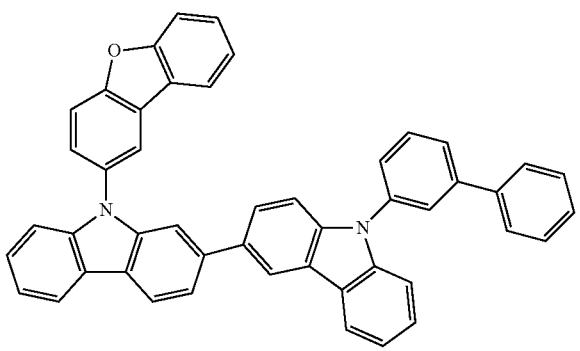
[E-78]
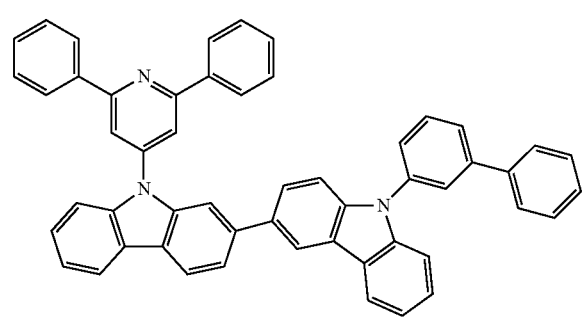
[E-82]
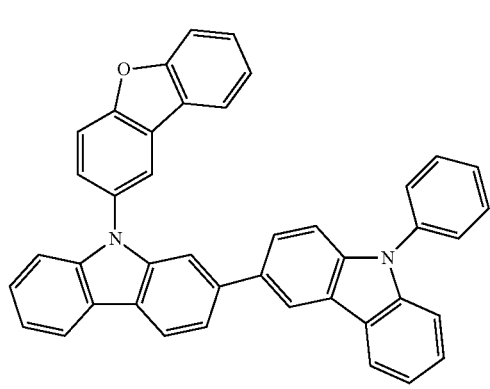
[E-79]
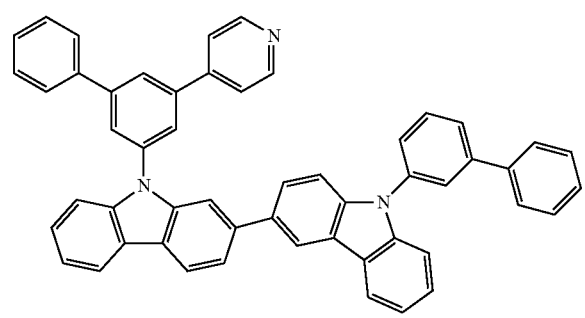
[E-83]
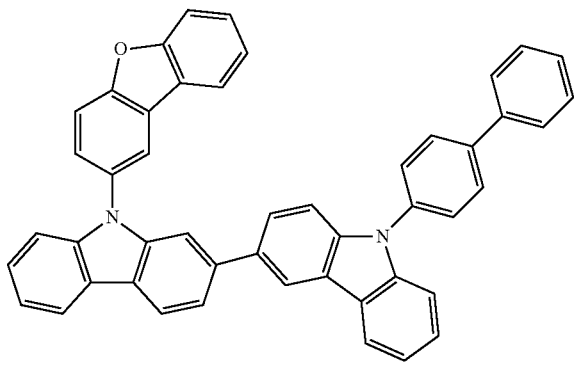
[E-80]
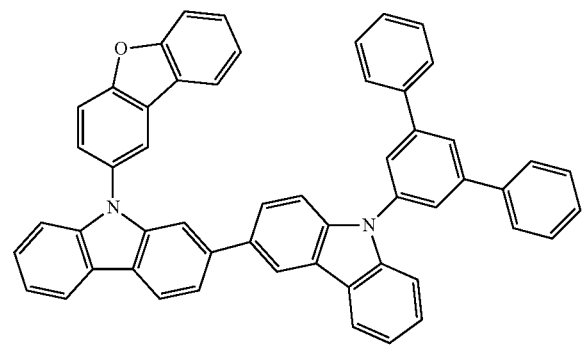
[E-84]
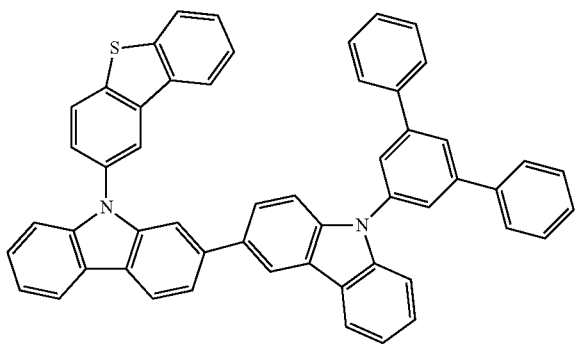

-continued
[E-85]
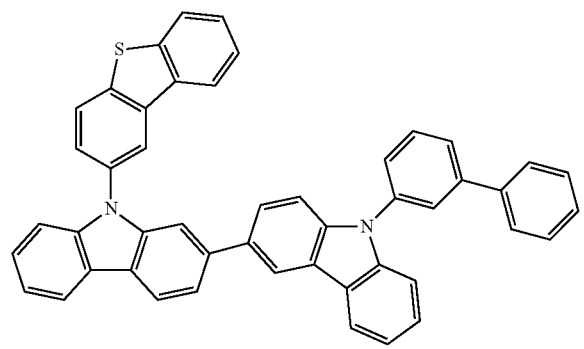
[E-86]
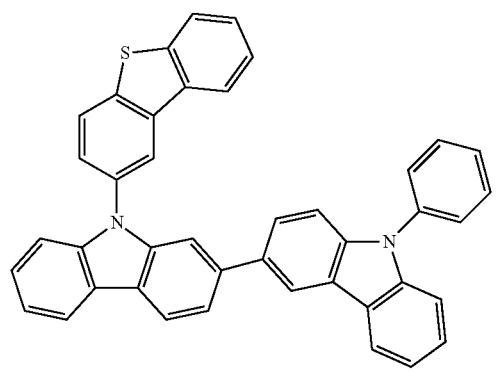
[E-87]
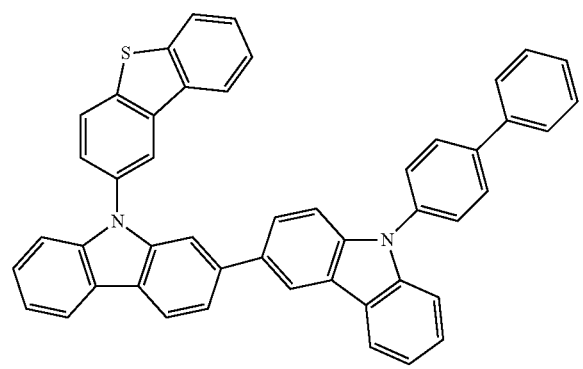
[E-88]
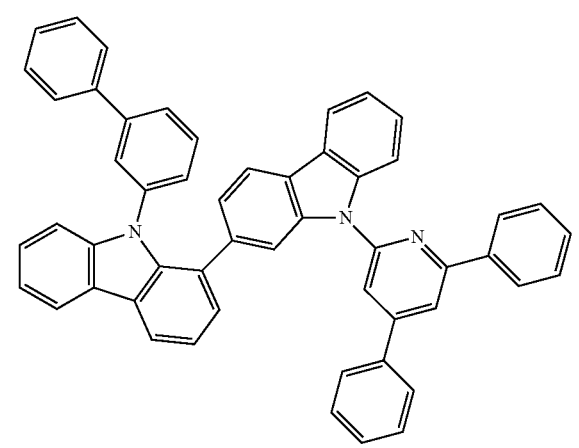
-continued
[E-89]
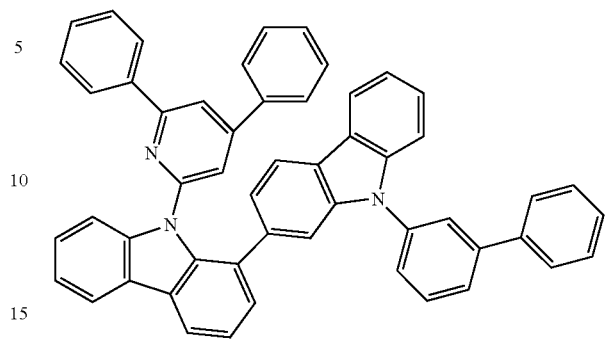
[E-90]
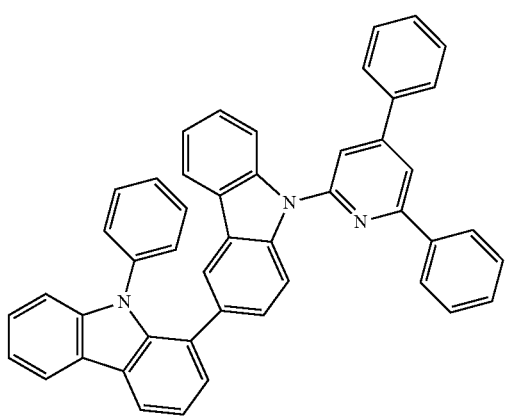
[E-91]
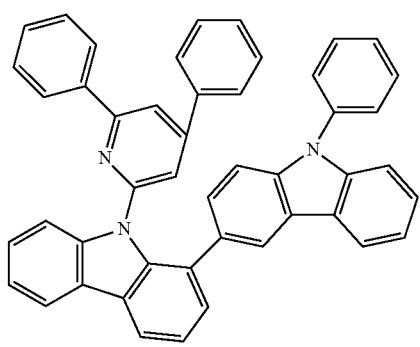
[E-92]
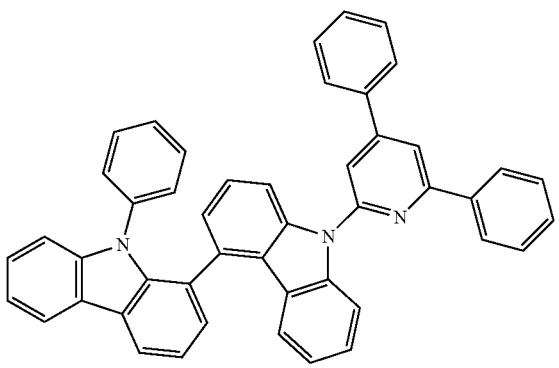

[E-93]
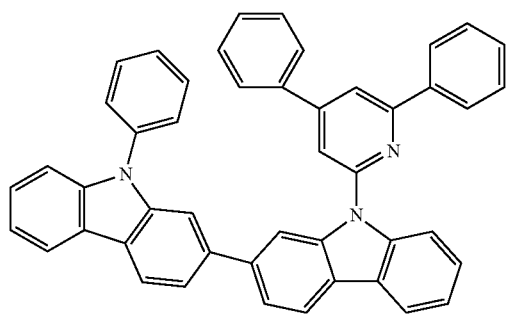
[E-97]
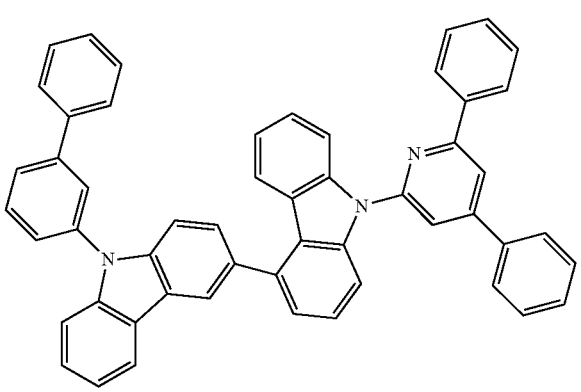
[E-94]
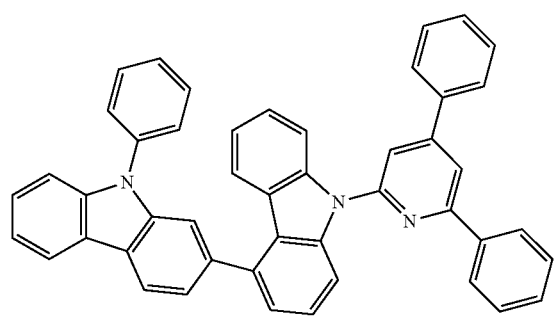
[E-98]
[E-95]
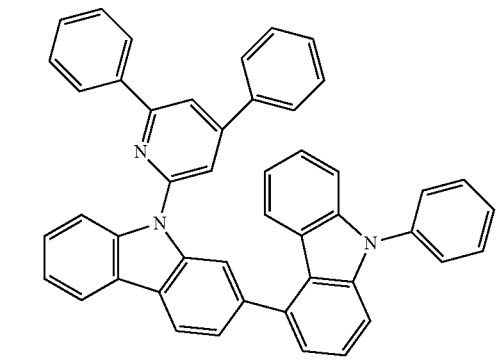
[E-99]
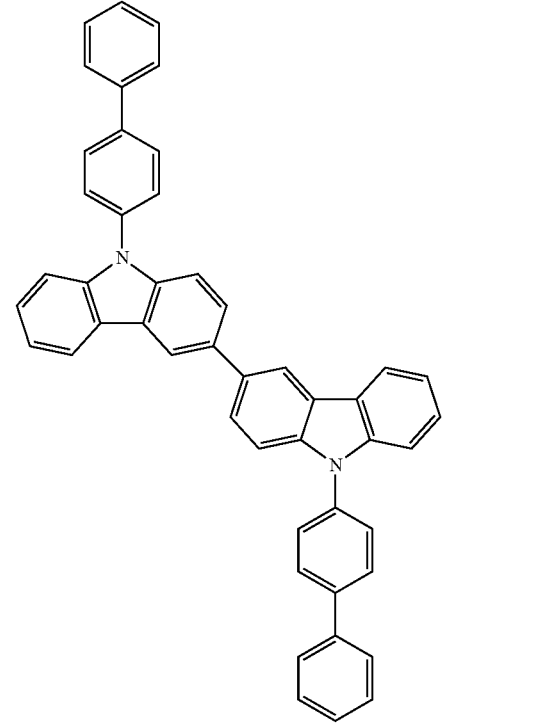
[E-96]
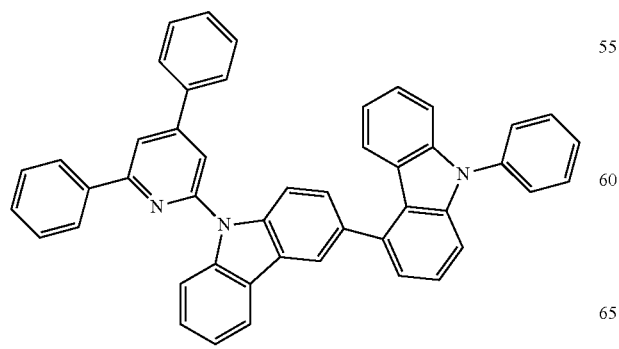

[E-100]
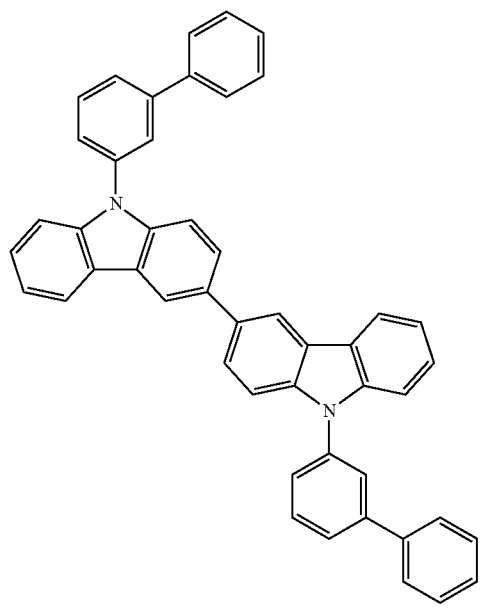
[E-103]
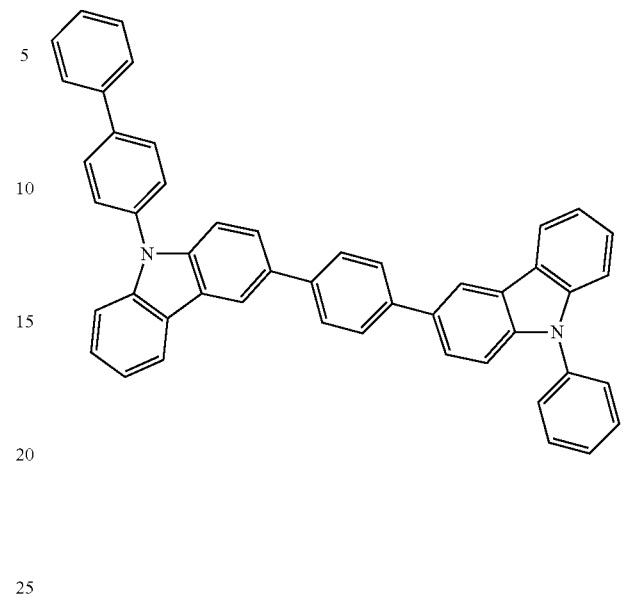
[E-101]
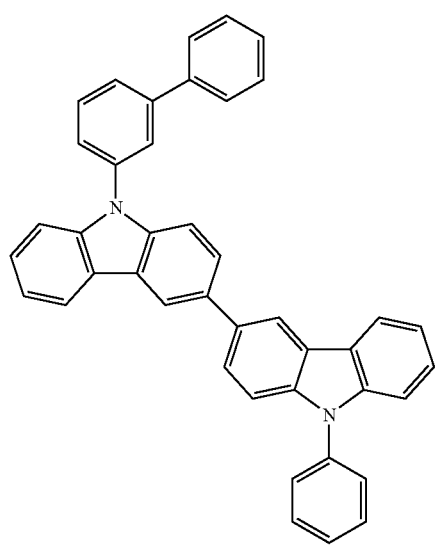
[E-104]
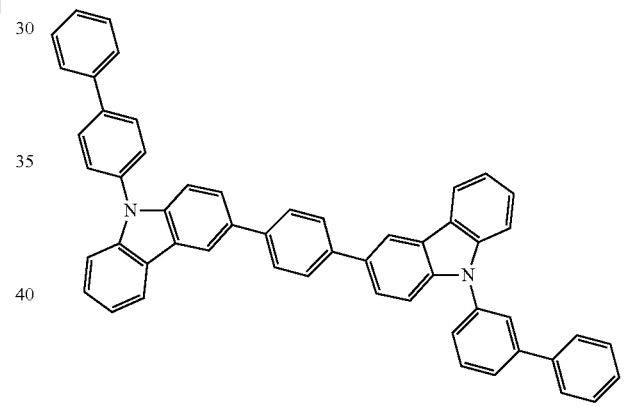
[E-102]
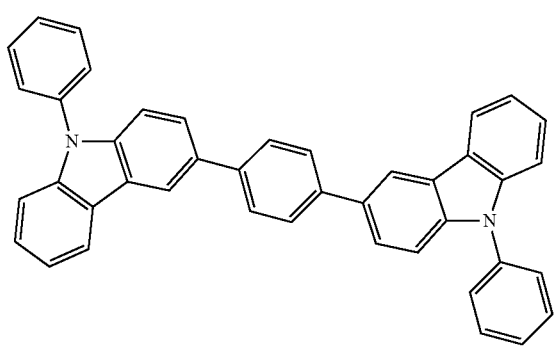
[E-105]
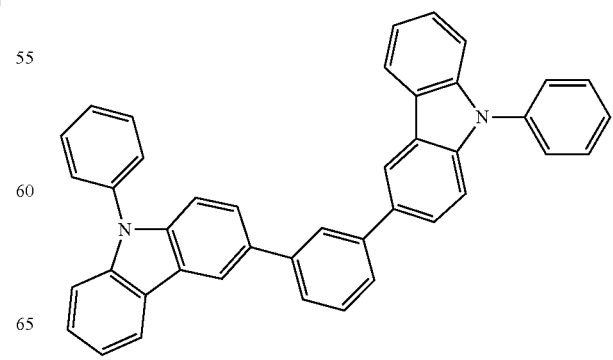

-continued
[E-106]
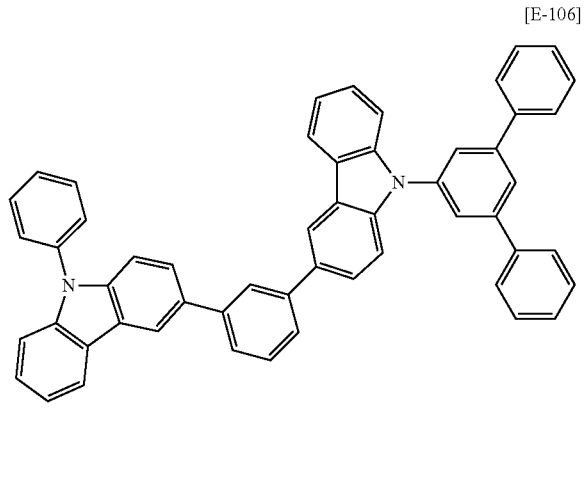
[E-109]
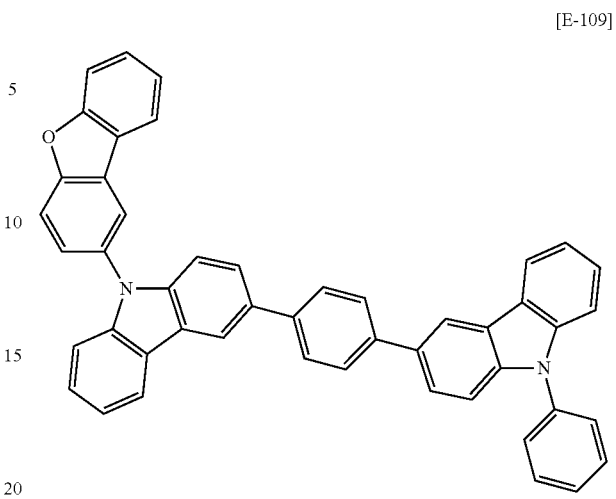
[E-107]
[E-110]
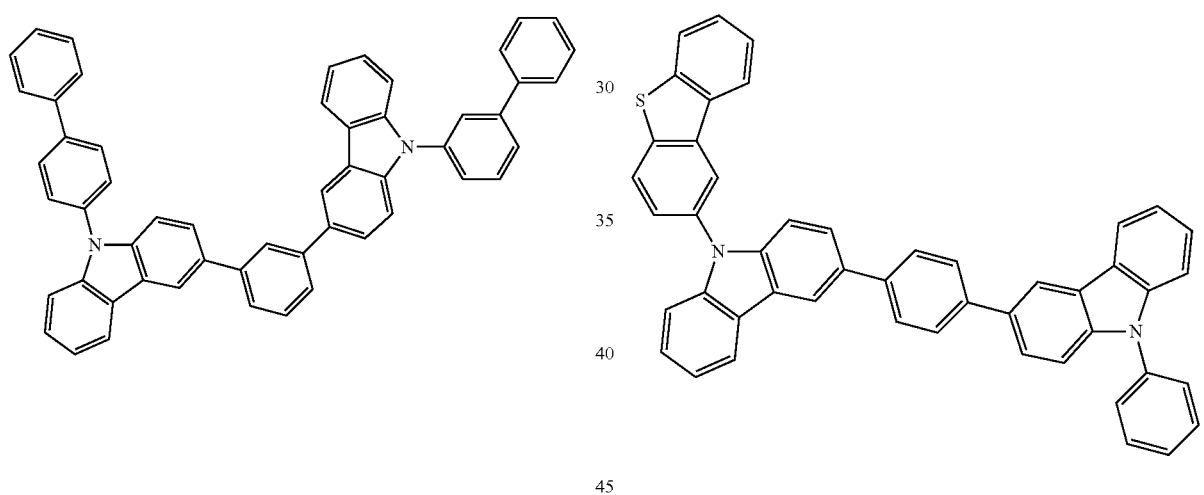
[E-108]
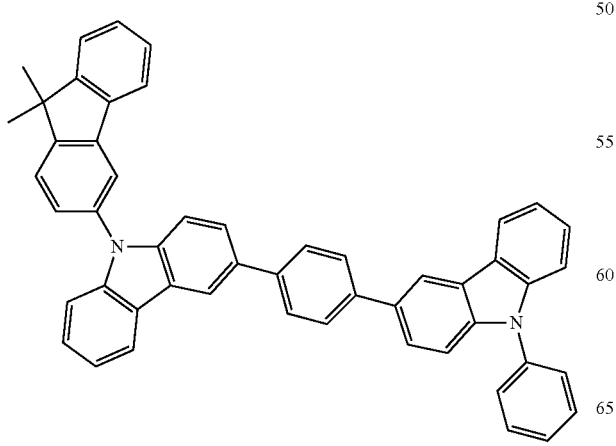
[E-111]
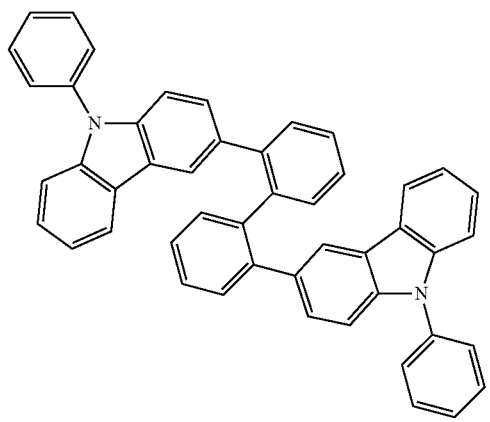

-continued
[E-112]
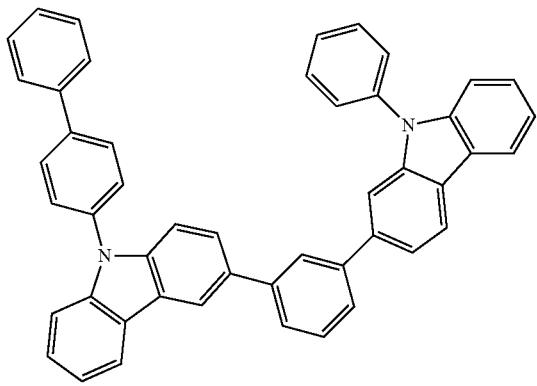
[E-115]
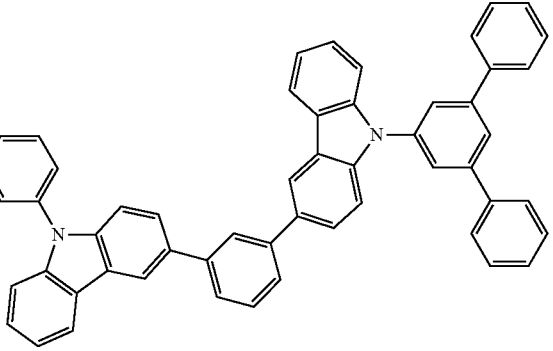
[E-113]
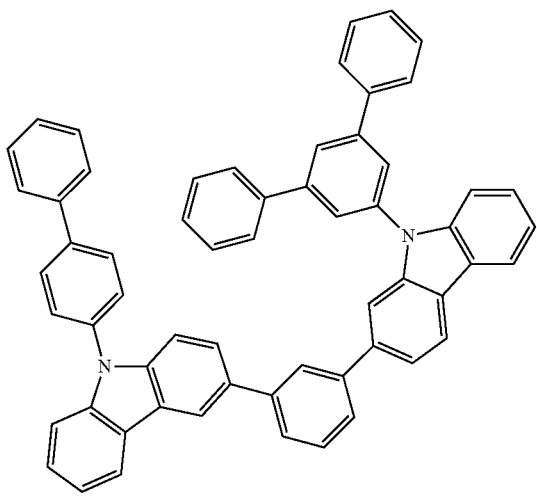
[E-116]
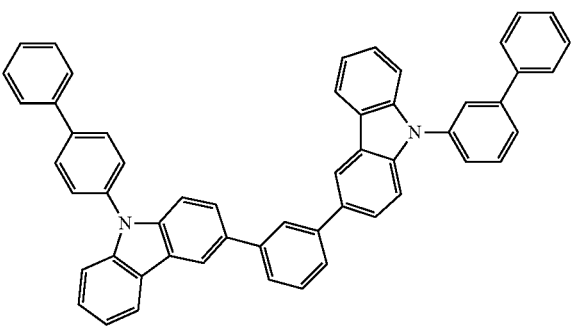
[E-114]
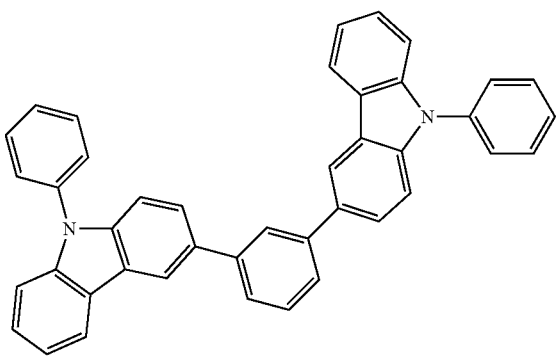
[E-117]
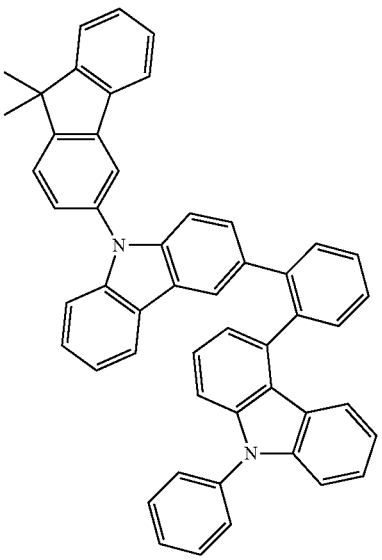

[E-118]
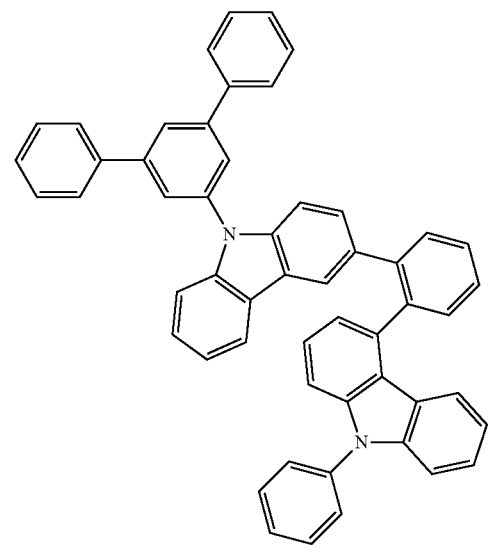
[E-119]
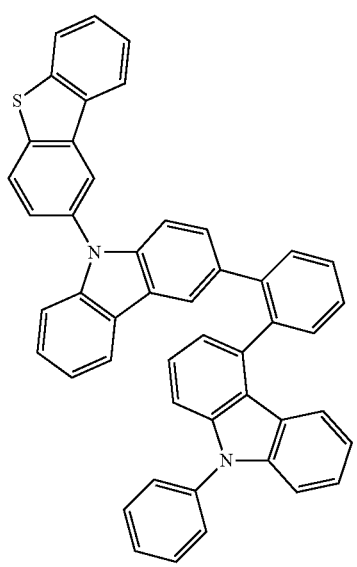
[E-120]
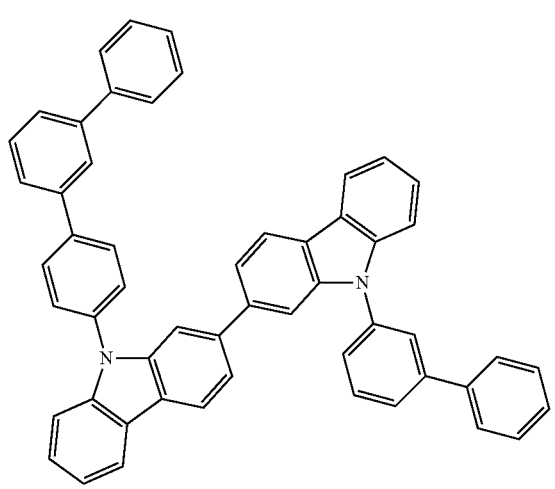
[E-121]
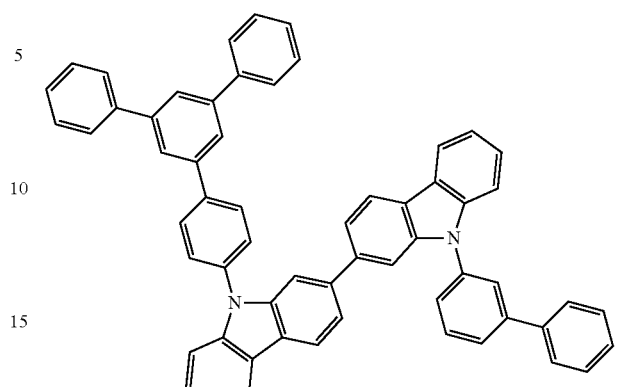
[E-122]
[E-123]
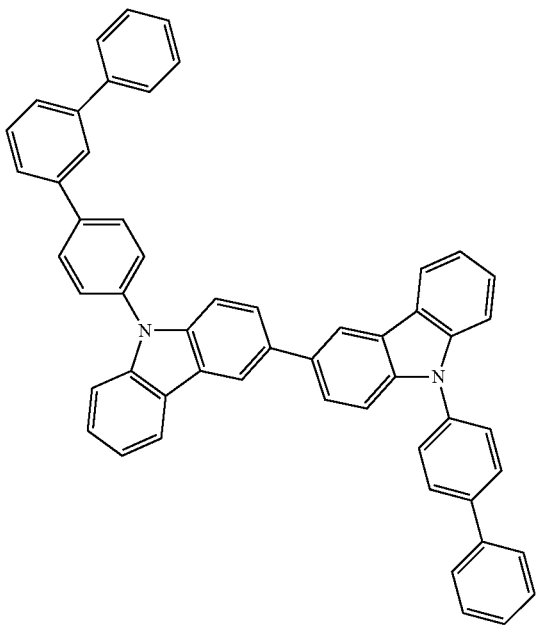

[E-124]
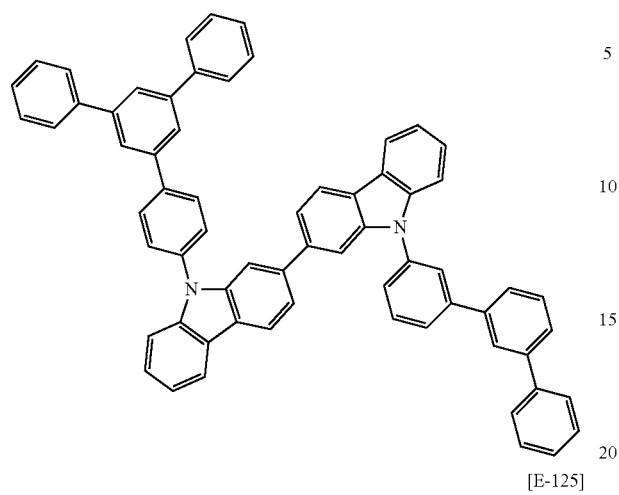
[E-125]
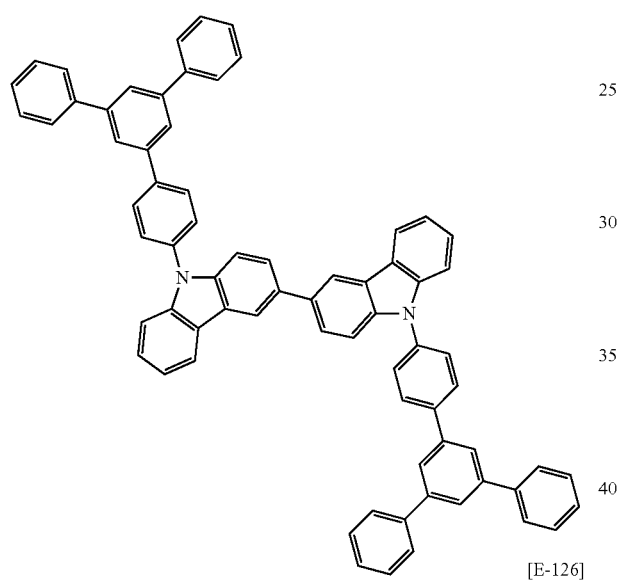
[E-126]
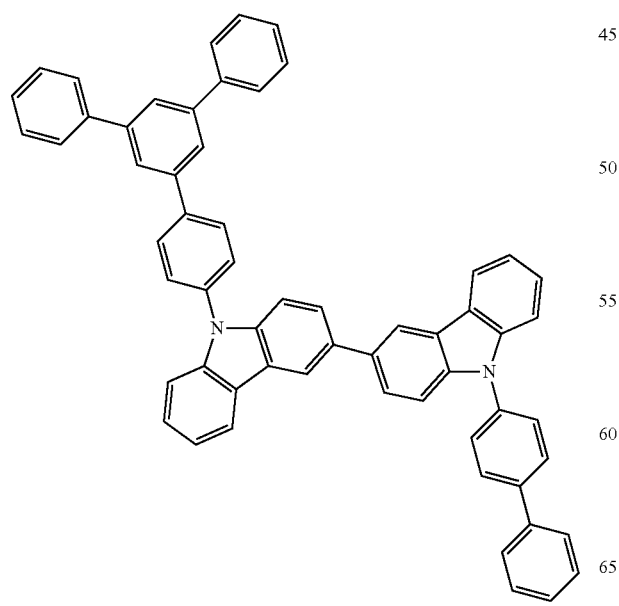
[E-127]
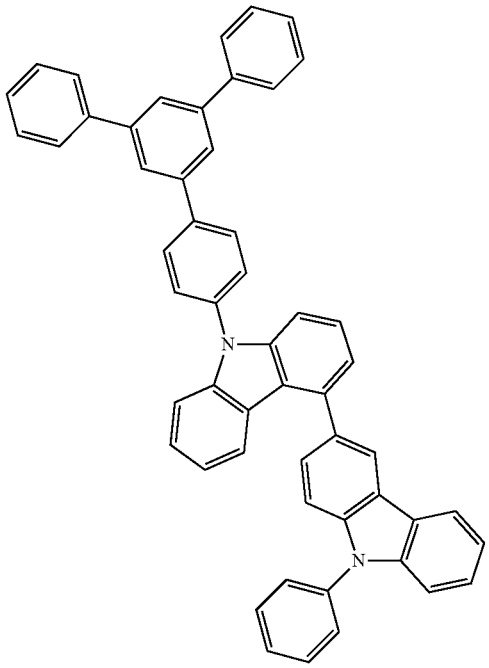
[E-128]
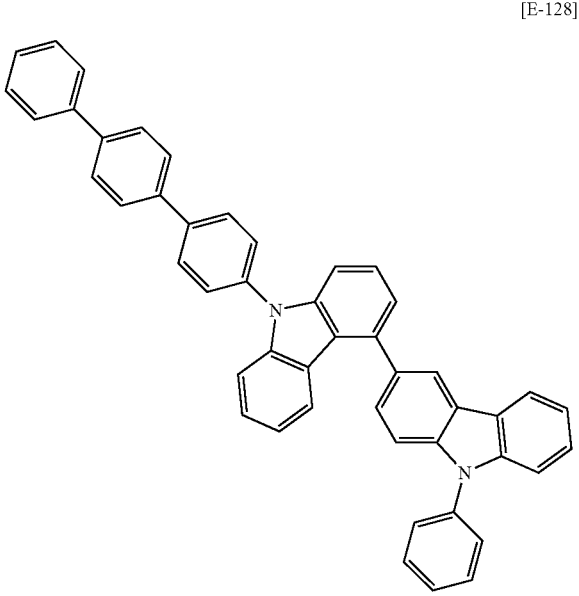

[E-129]
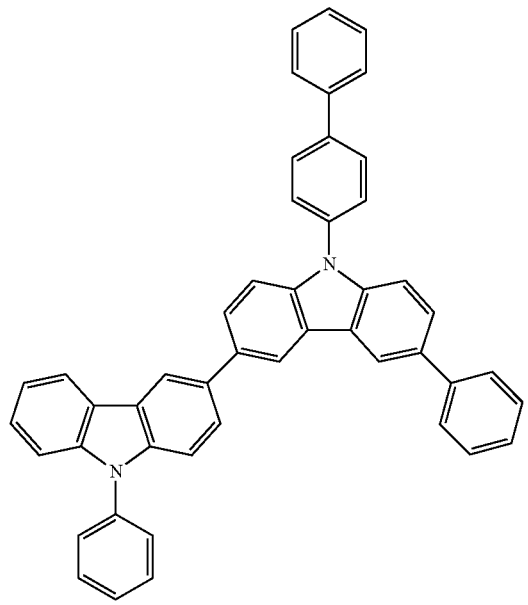
[E-130]
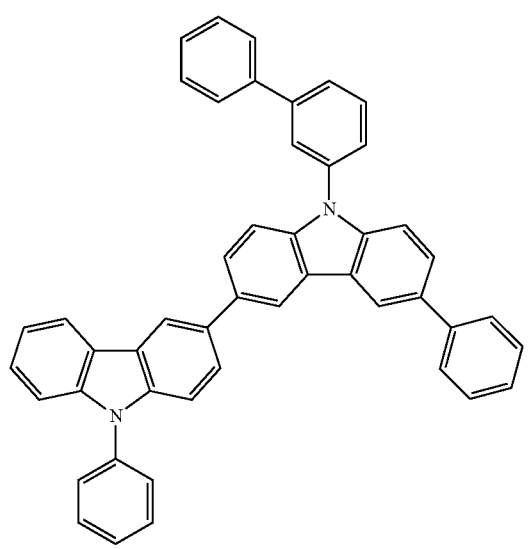
[E-131]
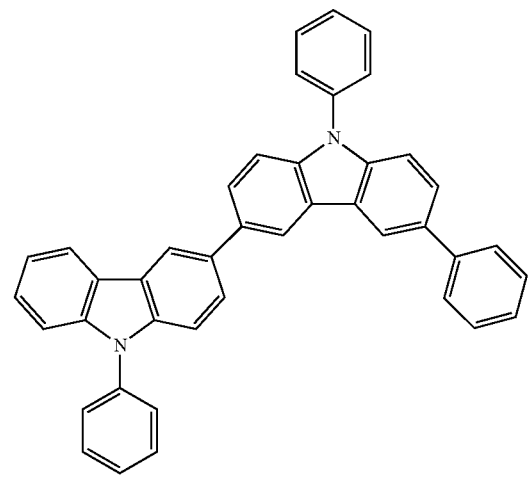
[E-132]
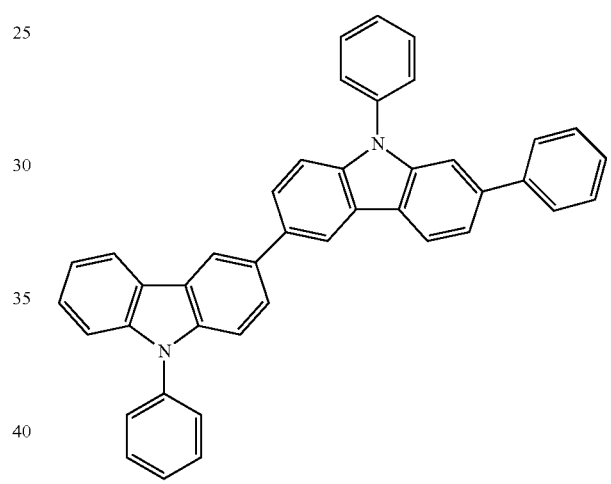
[E-133]
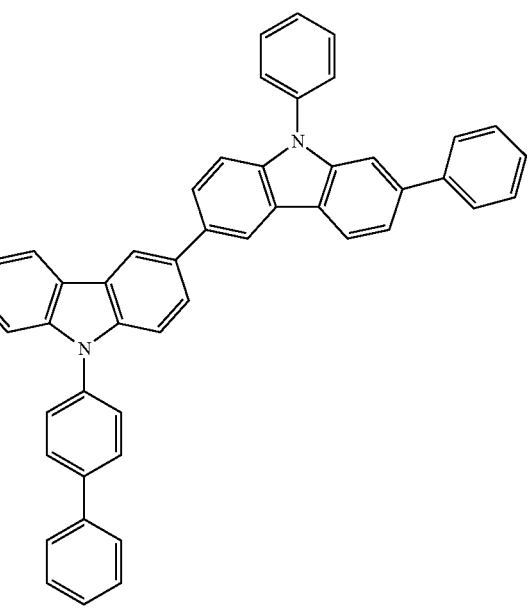

[E-134]
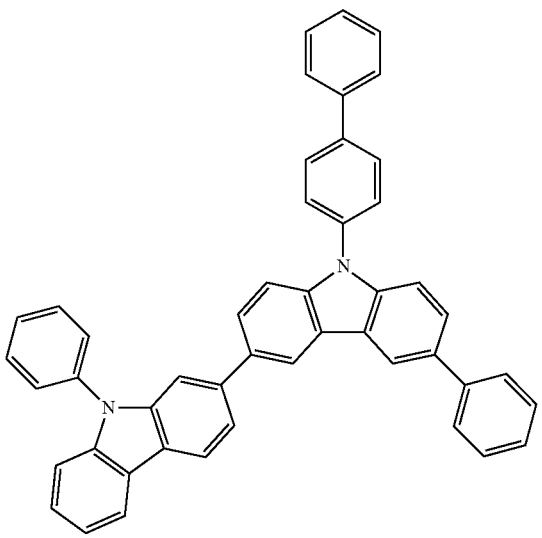

[E-135]
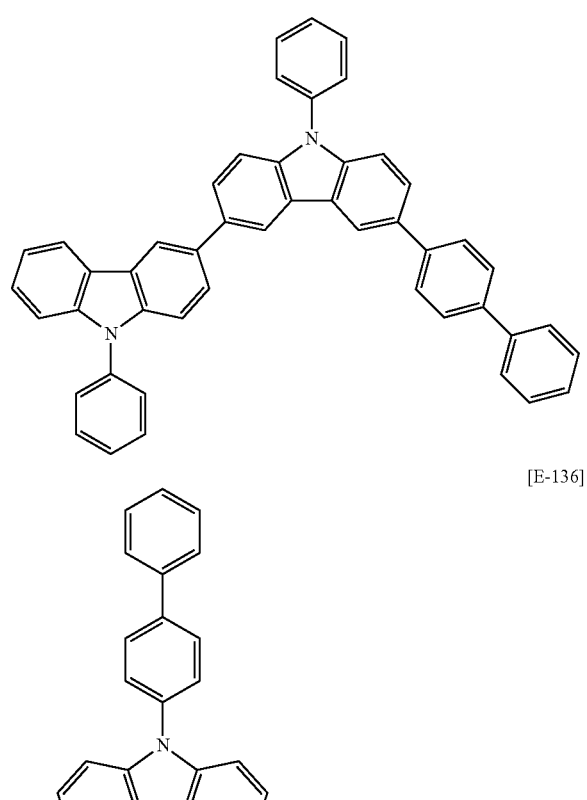

[E-136]

[E-137]
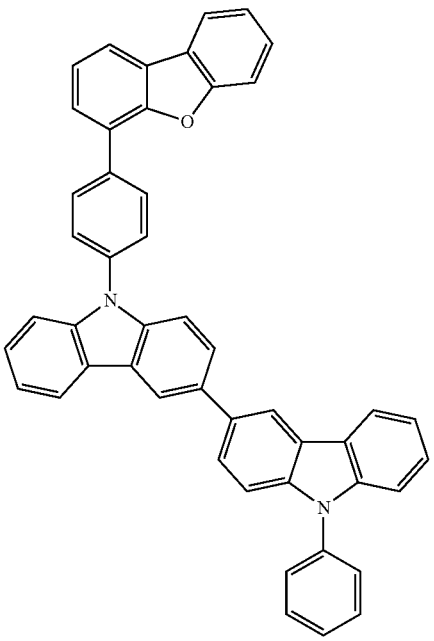

[E-138]
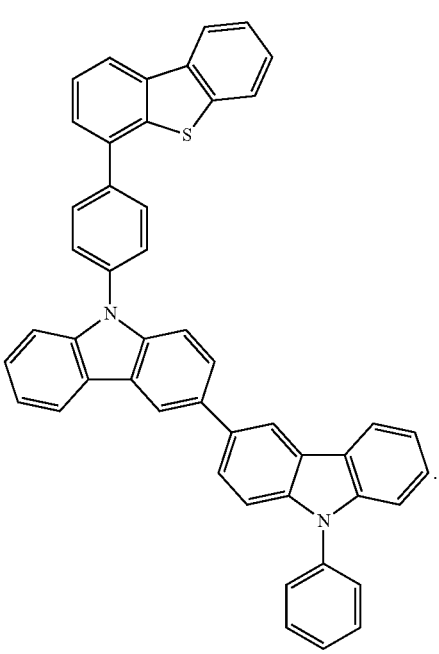

The first compound (first host) and the second compound (second host) may variously be combined to provide various compositions.

A composition according to an example embodiment of the present invention includes a compound represented by Chemical Formula 1-1, Chemical Formula 1-3, Chemical Formula 1-4, or Chemical Formula 1-5 as a first host, and a compound represented by Chemical Formula C-8 or Chemical Formula C-17 of Group I as a second host.

In addition, a first host represented by Chemical Formula 1-I, Chemical Formula 1-II, or Chemical Formula 1-III and a second host represented by Chemical Formula C-8 or Chemical Formula C-17 of Group I may be included.

For example, *-L$^1$-Z$^1$ and *-L$^2$-Z$^2$ of Chemical Formula 2 may be selected from B-1, B-2, B-3, and B-16 of Group II.

The second compound for an organic optoelectronic device is used with the first compound for an organic optoelectronic device in a light-emitting layer, and thereby charge mobility and stability are increased and luminous efficiency and life-span characteristics are improved. In addition, a ratio between the second compound for an organic optoelectronic device and the first compound for an organic optoelectronic device is controlled and thereby charge mobility may be controlled.

For example, the first compound for an organic optoelectronic device and the second compound for an organic optoelectronic device may be included in a weight ratio of about 1:9 to 9:1, specifically 2:8 to 8:2, 3:7 to 7:3, 4:6 to 6:4, or 5:5, and for example the first compound for an organic optoelectronic device and the second compound for an organic optoelectronic device may be included in a weight ratio of 3:7. Within the ranges, efficiency and life-span may be improved simultaneously.

The composition may further include one or more organic compound in addition to the first compound for an organic optoelectronic device and the second compound for an organic optoelectronic device.

The compound for an organic optoelectronic device may further include a dopant. The dopant may be a red, green, or blue dopant.

The dopant is a material in small amount to cause light emission and may be generally a material such as a metal complex that emits light by multiple excitation into a triplet or more. The dopant may be for example an inorganic, organic, or organic/inorganic compound, and one or more kinds thereof may be used.

One example of the dopant may be a phosphorescent dopant and examples of the phosphorescent dopant may be an organometal compound including Ir, Pt, Os, Ti, Zr, Hf, Eu, Tb, Tm, Fe, Co, Ni, Ru, Rh, Pd, or a combination thereof. The phosphorescent dopant may be, for example a compound represented by Chemical Formula Z, but is not limited thereto.

$$L_2MX \qquad \text{[Chemical Formula Z]}$$

In Chemical Formula Z, M is a metal, and L and X are the same or different, and are a ligand to form a complex compound with M.

The M may be for example, Ir, Pt, Os, Ti, Zr, Hf, Eu, Tb, Tm, Fe, Co, Ni, Ru, Rh, Pd, or a combination thereof and L and X may be for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer disposed between the anode and the cathode, wherein the organic layer includes the compound for an organic optoelectronic device or the composition for an organic optoelectronic device.

For example, the organic layer may include a light-emitting layer and the light-emitting layer may include the compound for an organic optoelectronic device or the composition for an organic optoelectronic device.

Specifically, the compound for an organic optoelectronic device or the composition for an organic optoelectronic device may be included as a green host of the light-emitting layer.

In addition, the organic layer includes a light-emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The auxiliary layer may further include an electron transport auxiliary layer that is adjacent to the light-emitting layer and the electron transport auxiliary layer may include the compound for an organic optoelectronic device, or the composition for an organic optoelectronic device.

In an example embodiment of the present invention, the compound for an organic optoelectronic device in the electron transport auxiliary layer may be represented by Chemical Formula 1-3.

The organic optoelectronic device may be any device to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic device is described referring to drawings.

Figure 2:
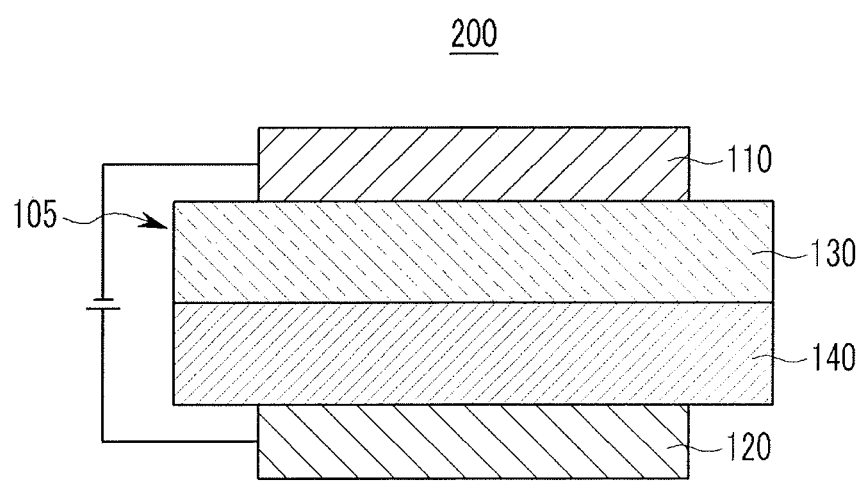

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or SnO$_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum, silver, tin, lead, cesium, barium, and the like; a multi-layer structure material such as LiF/Al, LiO$_2$/Al, LiF/Ca, LiF/Al and BaF$_2$/Ca, but is not limited thereto.

The organic layer 105 includes a light-emitting layer 130 including the compound for an organic optoelectronic device.

FIG. 2 is a cross-sectional view of an organic light emitting diode according to another embodiment.

Referring to FIG. 2, an organic light emitting diode 200 further includes a hole auxiliary layer 140 in addition to the light-emitting layer 130. The hole auxiliary layer 140 may further increase hole injection and/or hole mobility and block electrons between the anode 120 and the light-emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co., Ltd. or TCI Inc. as far as there is no particular comment or were synthesized by known methods.

(Preparation of Compound for Organic Optoelectronic Device)

The compound as one specific examples of the present invention was synthesized through the following steps.

(First Compound for Organic Optoelectronic Device)

Synthesis Example 1: Synthesis of Compound B-1

[Reaction Scheme 1]

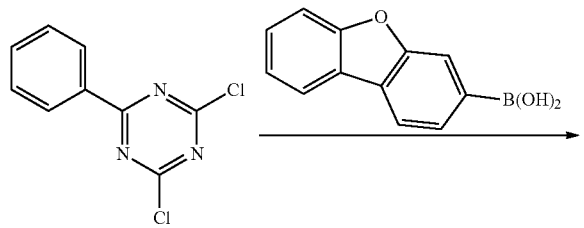

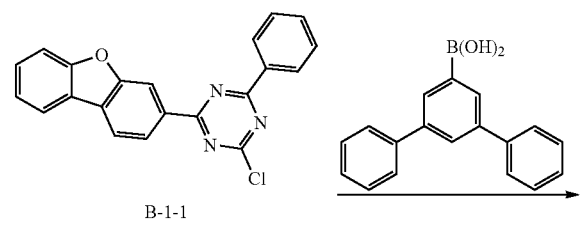

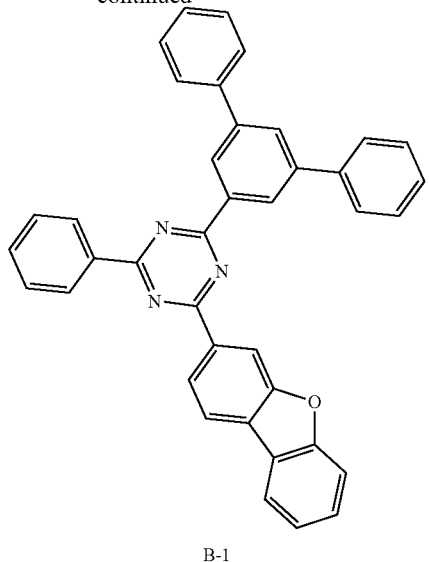

B-1 a) Synthesis of Intermediate B-1-1

2,4-dichloro-6-phenyltriazine (22.6 g, 100 mmol) was put in tetrahydrofuran (100 mL), toluene (100 mL), and distilled water (100 mL) in a 500 mL round-bottomed flask, 0.9 equivalents of dibenzofuran-3-boronic acid (CAS No: 395087-89-5), 0.03 equivalents of tetrakistriphenylphosphine palladium, and 2 equivalents of potassium carbonate were added, and the mixture was heated and refluxed under a under a nitrogen atmosphere. After 6 hours, a reaction solution was cooled down, an aqueous layer was removed and then an organic layer was dried under reduced pressure. Obtained solid was washed with water and hexane, and the solid was recrystallized with toluene (200 mL) to obtain 21.4 g (60% yield) of Intermediate B-1-1.

b) Synthesis of Compound B-1

The synthesized Intermediate B-1-1 (56.9 mmol) was put in tetrahydrofuran (200 mL) and distilled water (100 mL) in a 500 mL round-bottomed flask, and 1.1 equivalents of 3,5-diphenylbenzeneboronic acid (CAS No.: 128388-54-5), 0.03 equivalents of tetrakistriphenylphosphine palladium, and 2 equivalents of potassium carbonate were added, and the mixture was heated and refluxed under a under a nitrogen atmosphere. After 18 hours, a reaction solution was cooled, and a solid precipitated therein was filtered and washed with water (500 mL). The solid was recrystallized with monochlorobenzene (500 mL) to obtain Compound B-1.

LC/MS calculated for: C39H25N3O Exact Mass: 555.1998 found for 556.21 [M+H].

Synthesis Example 2: Synthesis of Compound B-7
[Reaction Scheme 2]
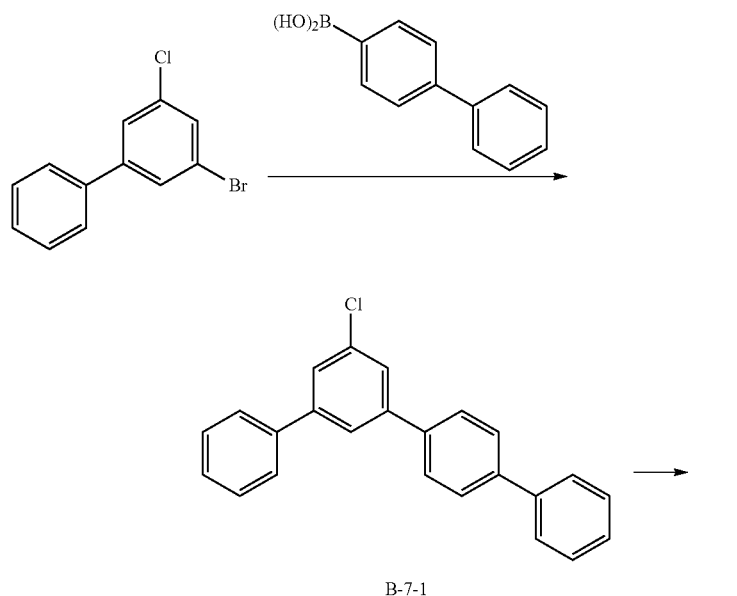
B-7-1
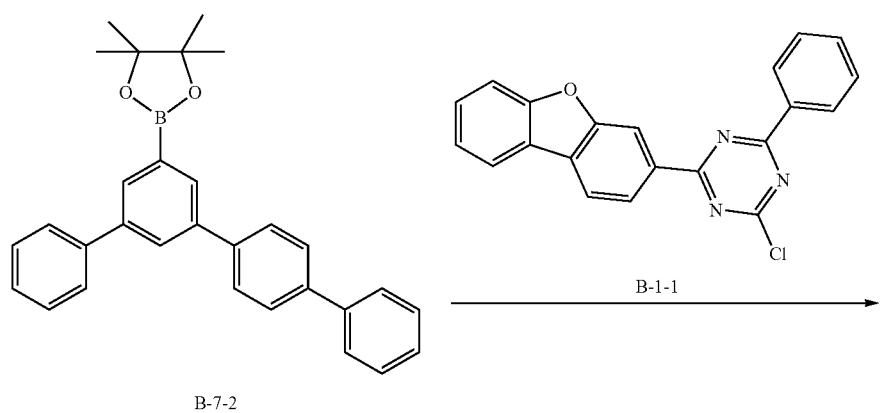
B-7-2
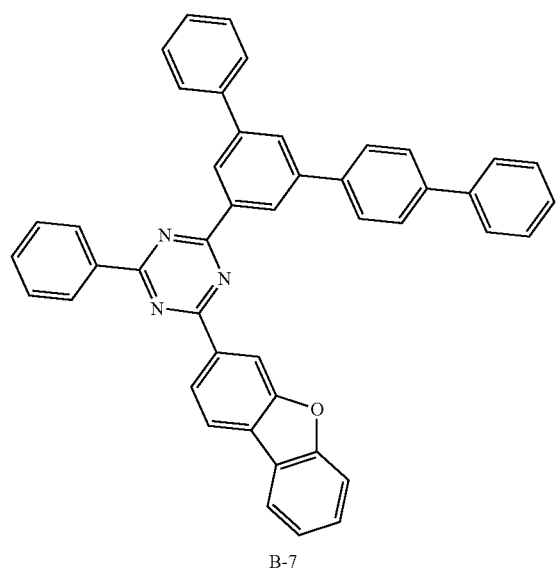
B-7 a) Synthesis of Intermediate B-7-1

Intermediate B-7-1 was synthesized according to the same method as b) of Synthesis Example 1 by using 1-bromo-3-chloro-5-phenylbenzene and 1.1 equivalents of biphenyl-4-boronic acid. Herein, a product was purified through a flash column using hexane instead of recrystallization.

b) Synthesis of Intermediate B-7-2

The synthesized intermediate B-7-1 30 g (88.02 mmol) was put in DMF (250 mL) in a 500 mL round-bottomed flask, 0.05 equivalents of dichlorodiphenyl phosphinoferrocene palladium, 1.2 equivalents of bispinacolato diboron, and 2 equivalents of potassium acetate were put, and heated and refluxed under a under a nitrogen atmosphere for 18 hours. A reaction solution was cooled down and was dripped in 1 L of water to capture a solid. The obtained solid was dissolved in boiling toluene and was treated with activated carbon, and then filtrate was concentrated after filtering with a silica gel filter. A concentrated solid was stirred with a small amount of hexane, and then the solid was filtered to obtain 28.5 g (a yield of 70%) of Intermediate B-7-2.

c) Synthesis of Compound B-7

Compound B-7 was synthesized according to the same method as b) of Synthesis Example 1 by using 1.0 equivalent of Intermediate B-7-2 and 1.0 equivalent of Intermediate B-1-1.

LC/MS calculated for: C45H29N3O Exact Mass: 627.2311 found for 628.22 [M+H].

Synthesis Example 3: Synthesis of Compound B-9

[Reaction Scheme 3]

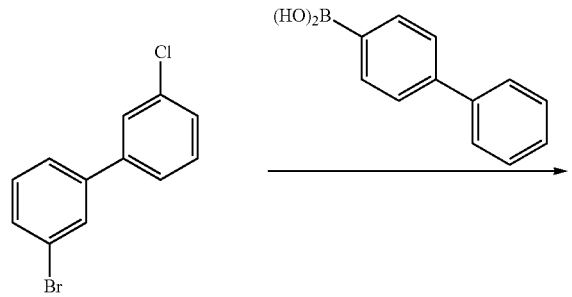

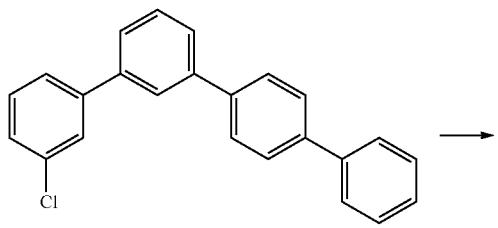

B-9-1

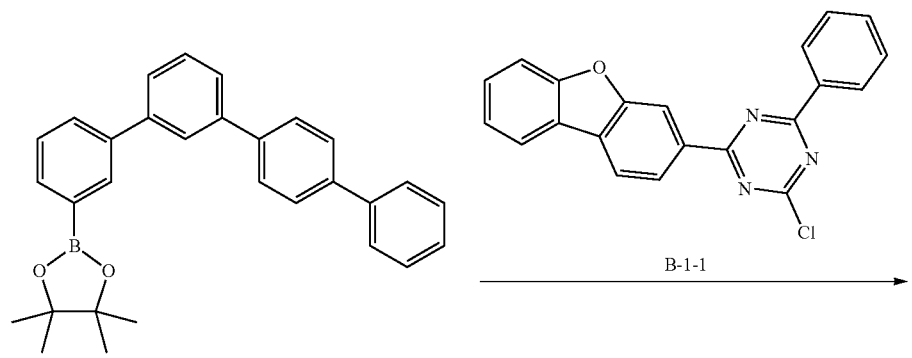

B-9-2

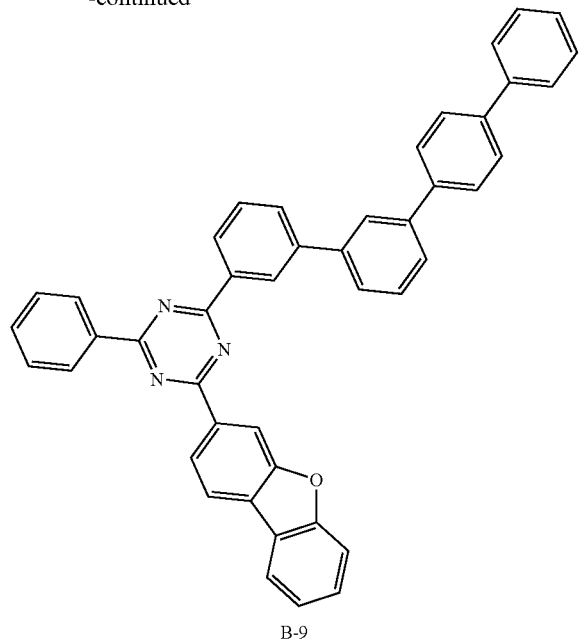

B-9 a) Synthesis of Intermediate B-9-1

Intermediate B-9-1 was synthesized according to the same method as b) of Synthesis Example 1 by using 1 equivalent of 3-bromo-3'-chloro-1,1'-biphenyl (CAS No.: 844856-42-4) and 1.1 equivalents of biphenyl-4-boronic acid. Herein, a product was purified through a flash column using hexane instead of recrystallization.

b) Synthesis of Intermediate B-9-2

Intermediate B-9-2 was synthesized by performing a reaction under the same condition as b) of Synthesis Example 2 by using Intermediate B-9-1.

c) Synthesis of Compound B-9

Compound B-9 was synthesized according to the same method as b) of Synthesis Example 1 by using 1.0 equivalent of Intermediate B-9-2 and 1.0 equivalent of Intermediate B-1-1.

LC/MS calculated for: C45H29N3O Exact Mass: 627.2311 found for 628.22 [M+H].

Synthesis Example 4: Synthesis of Compound B-11

[Reaction Scheme 4]

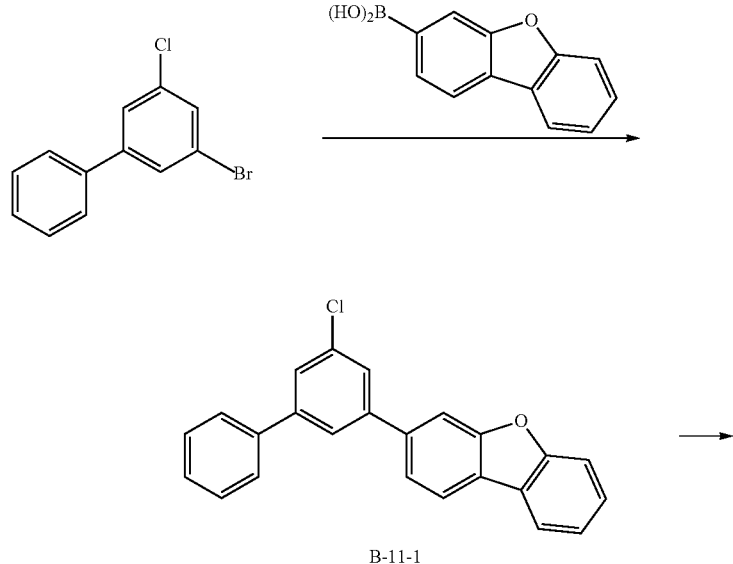

B-11-1

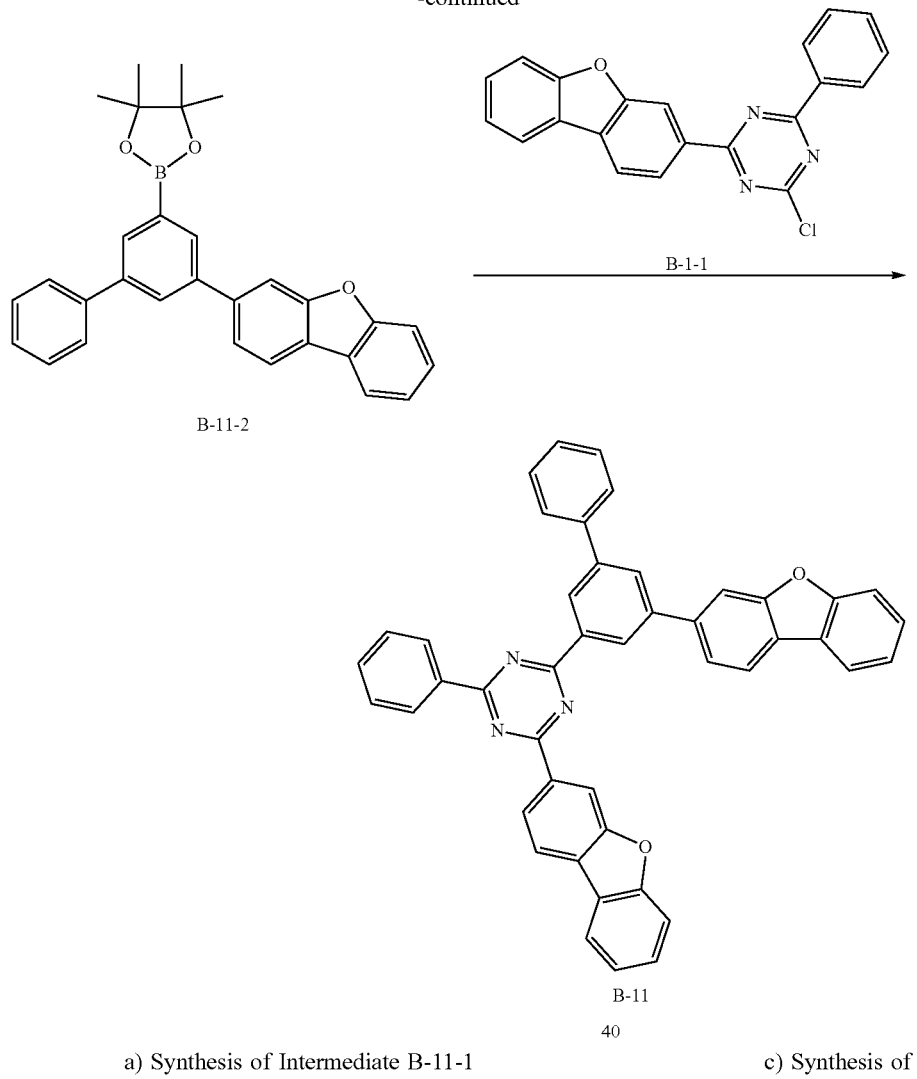

B-11-2

B-11 a) Synthesis of Intermediate B-11-1

Intermediate B-11-1 was synthesized according to the same method as b) of Synthesis Example 1 by using 1 equivalent of 1-bromo-3-chloro-5-phenylbenzene and 1.1 equivalents of dibenzofuran-3-boronic acid.

b) Synthesis of Intermediate B-11-2

Intermediate B-11-2 was synthesized by performing a reaction under the same condition as b) of Synthesis Example 2 by using Intermediate B-11-1.

c) Synthesis of Compound B-11

Compound B-11 was synthesized according to the same method as b) of Synthesis Example 1 by using 1.0 equivalent of Intermediate B-11-2 and 1.0 equivalent of Intermediate B-1-1.

LC/MS calculated for: C45H27N3O2 Exact Mass: 641.2103 found for 642.22 [M+H].

Synthesis Example 5: Synthesis of Compound B-13

[Reaction Scheme 5]

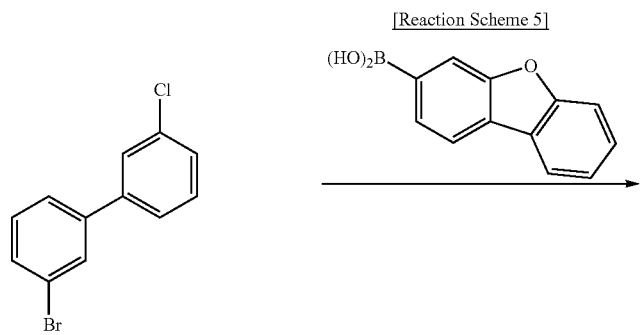

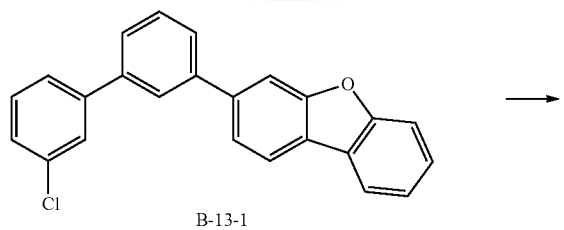
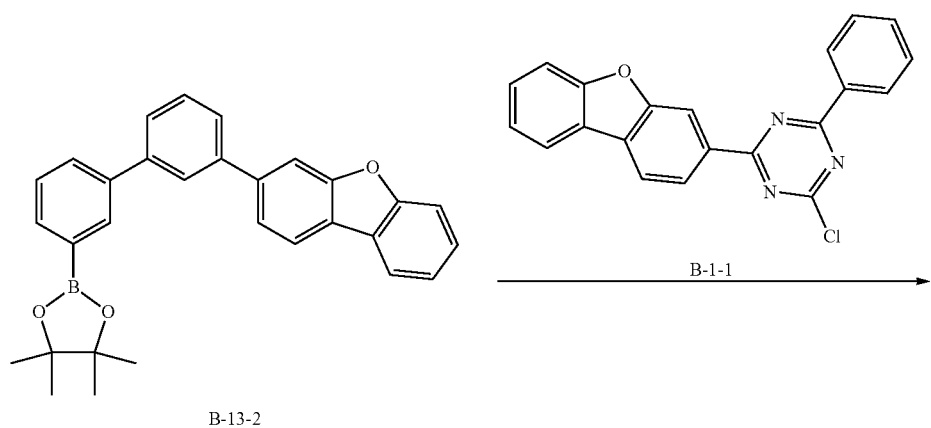
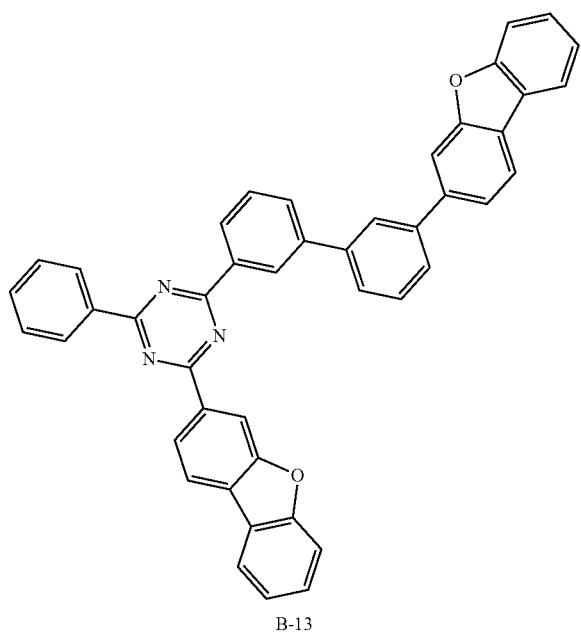

a) Synthesis of Intermediate B-13-1

Intermediate B-13-1 was synthesized according to the same method as b) of Synthesis Example 1 by using 1 equivalent of 3-bromo-3'-chloro-1,1'-biphenyl (CAS No.: 844856-42-4) and 1.1 equivalents of dibenzofuran-3-boronic acid.

b) Synthesis of Intermediate B-13-2

Intermediate B-13-2 was synthesized by performing a reaction under the same condition as b) of Synthesis Example 2 by using Intermediate B-13-1.

c) Synthesis of Compound B-13

Compound B-13 was synthesized according to the same method as b) of Synthesis Example 1 by using 1.0 equivalent of Intermediate B-13-2 and 1.0 equivalent of Intermediate B-1-1.

LC/MS calculated for: C45H27N3O2 Exact Mass: 641.2103 found for 642.22 [M+H].

Synthesis Example 6: Synthesis of Compound B-14

[Reaction Scheme 6]

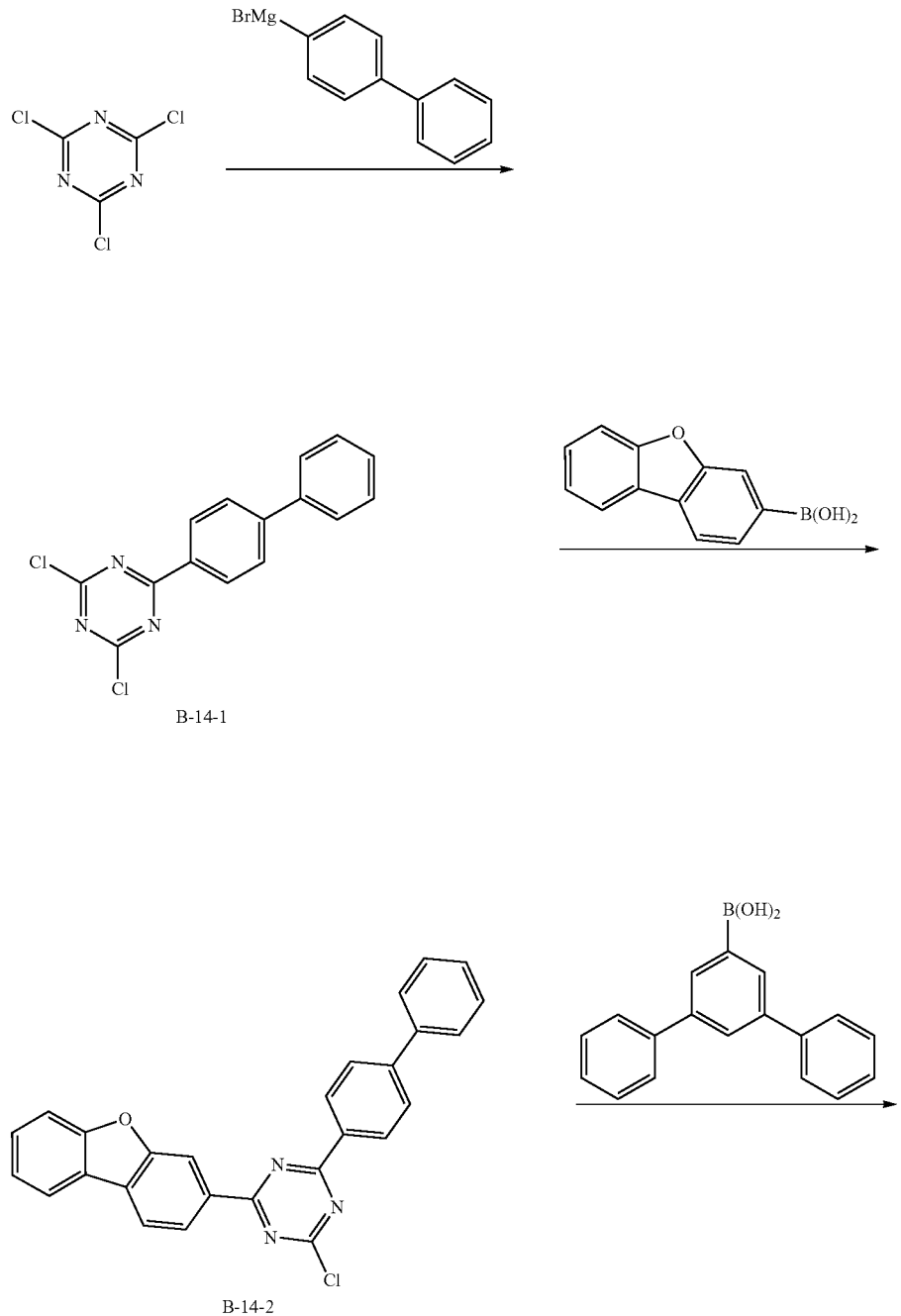

-continued

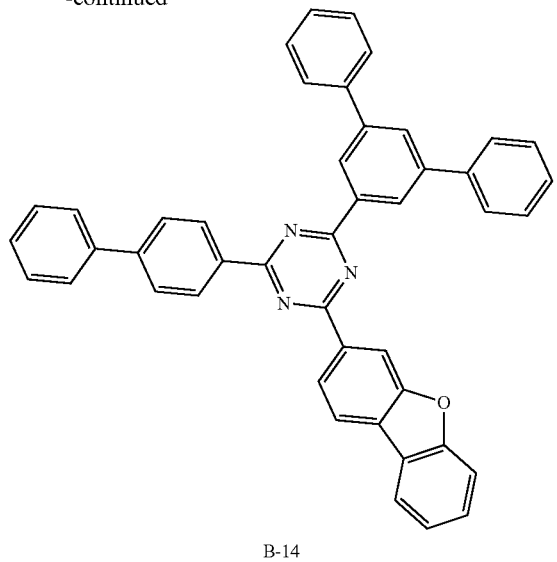

B-14 a) Synthesis of Intermediate B-14-1

Cyanuric chloride (15 g, 81.34 mmol) was dissolved in anhydrous tetrahydrofuran (200 mL) in a 500 mL round-bottomed flask, 1 equivalent of a 4-biphenyl magnesium bromide solution (0.5 M tetrahydrofuran) was added thereto in a dropwise fashion at 0° C. under a nitrogen atmosphere, and the temperature was slowly increased up to room temperature. A reaction solution was stirred at room temperature for 1 hour and then, added to ice water (500 mL) to separate layers. An organic layer was separated therefrom, treated with anhydrous magnesium sulfate, and concentrated. Concentrated residue was recrystallized with tetrahydrofuran and methanol to obtain Intermediate B-14-1 (17.2 g).

b) Synthesis of Intermediate B-14-2

Intermediate B-14-2 was synthesized according to the same method as a) of Synthesis Example 1 by using Intermediate B-14-1.

c) Synthesis of Compound B-14

Compound B-14 was synthesized according to the same method as b) of Synthesis Example 1 by using Intermediate B-14-2 and 1.1 equivalents of 3,5-diphenylbenzeneboronic acid.

LC/MS calculated for: C45H29N3O Exact Mass: 627.2311 found for 628.24 [M+H].

Synthesis Example 7: Synthesis of Compound B-16

[Reaction Scheme 7]

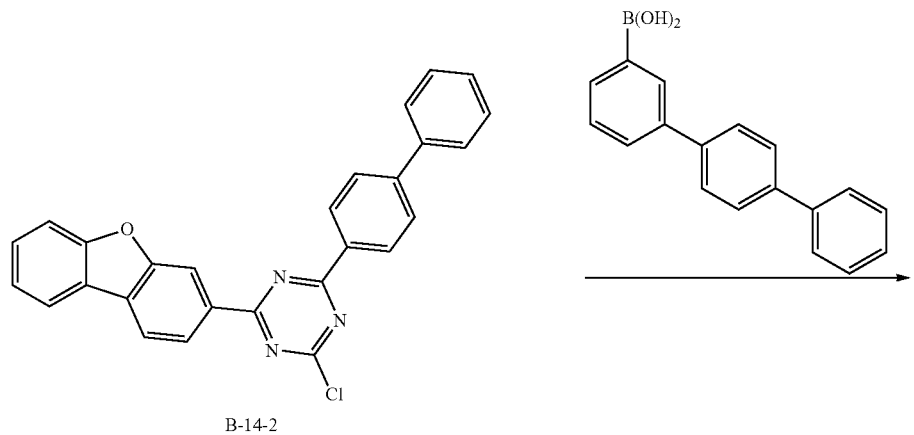

B-14-2

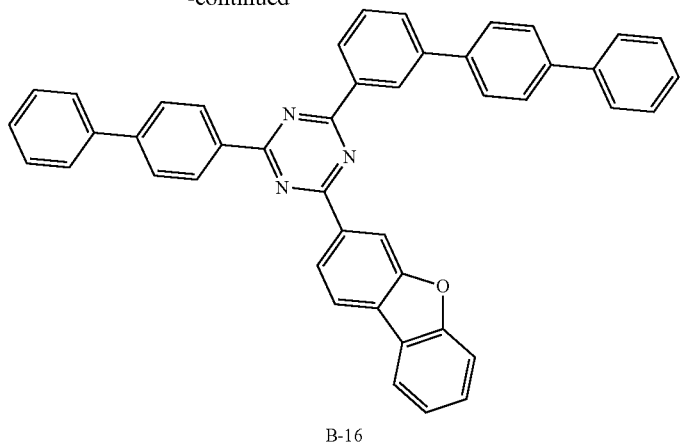
B-16
a) Synthesis of Compound B-16
Compound B-16 was synthesized according to the same method as b) of Synthesis Example 1 by using Intermediate B-14-2 and 1.1 equivalents of B-[1,1': 4',1"-terphenyl]-3-ylboronic acid.
LC/MS calculated for: C45H29N3O Exact Mass: 627.2311 found for 628.24 [M+H].
Synthesis Example 8: Synthesis of Compound B-40
[Reaction Scheme 8]
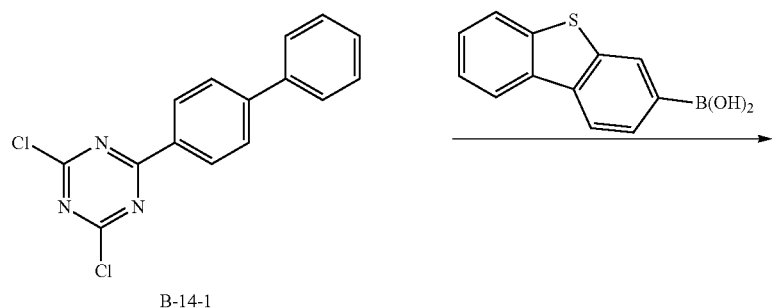
B-14-1
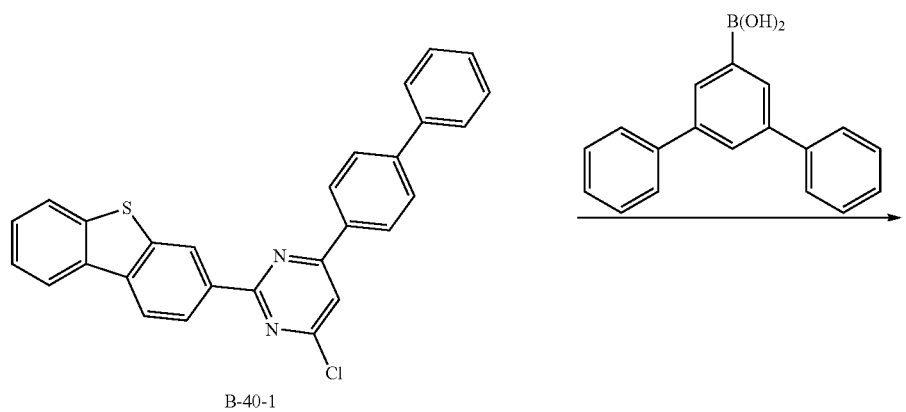
B-40-1

-continued

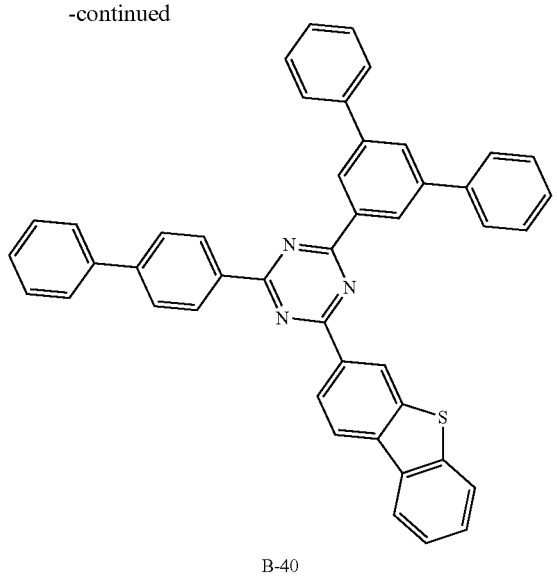

B-40 a) Synthesis of Intermediate B-40-1

Intermediate B-40-1 was synthesized according to the same method as a) of Synthesis Example 1 by using Intermediate B-14-1.

b) Synthesis of Compound B-40

Compound B-40 was synthesized according to the same method as b) of Synthesis Example 1 by using Intermediate B-40-1 and 1.1 equivalents of 3,5-diphenylbenzeneboronic acid.

LC/MS calculated for: C45H29N3S Exact Mass: 643.2082 found for 644.21 [M+H].

Synthesis Example 9: Synthesis of Compound B-53

[Reaction Scheme 9]

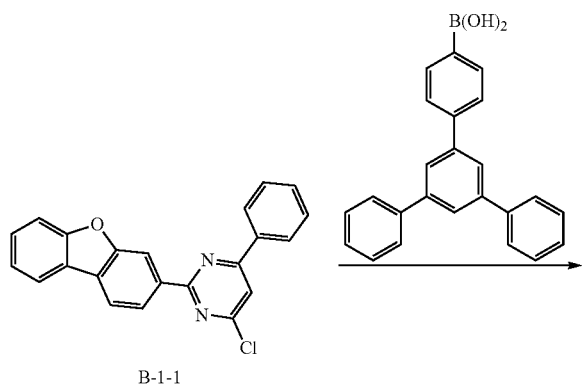

-continued

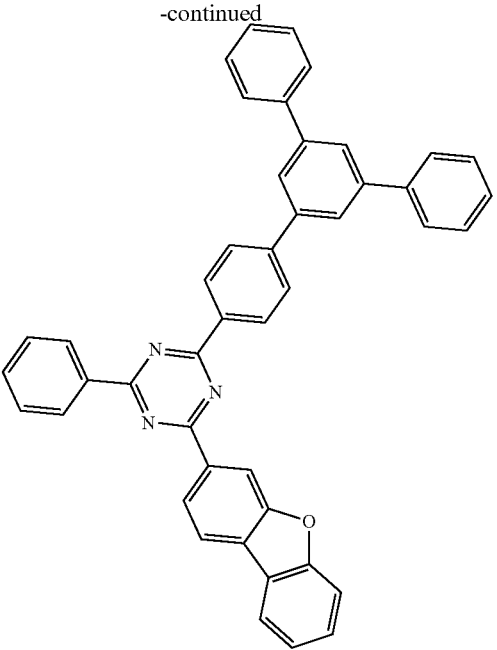

B-53 a) Synthesis of Compound B-53

Compound B-53 was synthesized according to the same method as b) of Synthesis Example 1 by using Intermediate B-1-1 and 1.1 equivalents of (5'-phenyl[1,1':3',1''-terphenyl]-4-yl)-boronic acid (CAS No.: 491612-72-7).

LC/MS calculated for: C45H29N3O Exact Mass: 627.2311 found for 628.24 [M+H].

Synthesis Example 10: Synthesis of Compound B-70

[Reaction Scheme 10]

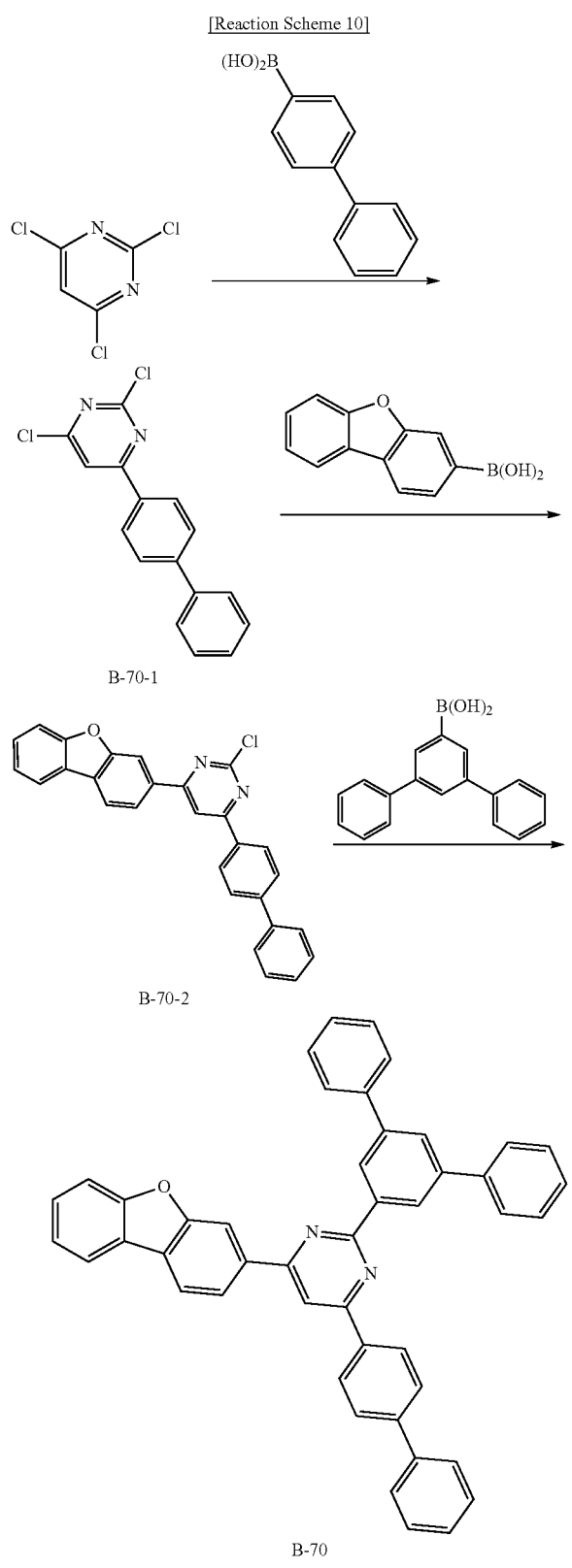

a) Synthesis of Intermediate B-70-1

2,4,6-trichloropyrimidine (18.3 g, 100 mmol) was put in tetrahydrofuran (100 mL), toluene (100 mL), and distilled water (100 mL) in a 500 mL round-bottomed flask, 0.9 equivalents of biphenyl-4-boronic acid, 0.03 equivalents of tetrakistriphenylphosphine palladium, and 2 equivalents of potassium carbonate were added, and the mixture was heated and refluxed under a nitrogen atmosphere. After 8 hours, a reaction solution was cooled down, an aqueous layer was removed and then an organic layer was dried to obtain a solid. Through column chromatography, Intermediate B-70-1 (21.1 g, 70%) was synthesized.

b) Synthesis of Intermediate B-70-2

Intermediate B-70-2 was synthesized according to the same method as a) of Synthesis Example 1 by using Intermediate B-70-1.

c) Synthesis of Compound B-70

Compound B-70 was synthesized according to the same method as b) of Synthesis Example 1 by using Intermediate B-70-2 and 1.1 equivalents of 3,5-diphenylbenzeneboronic acid.

LC/MS calculated for: C46H30N2O Exact Mass: 626.2358 found for 627.24 [M+H].

Synthesis Example 11: Synthesis of Compound B-78

[Reaction Scheme 11]

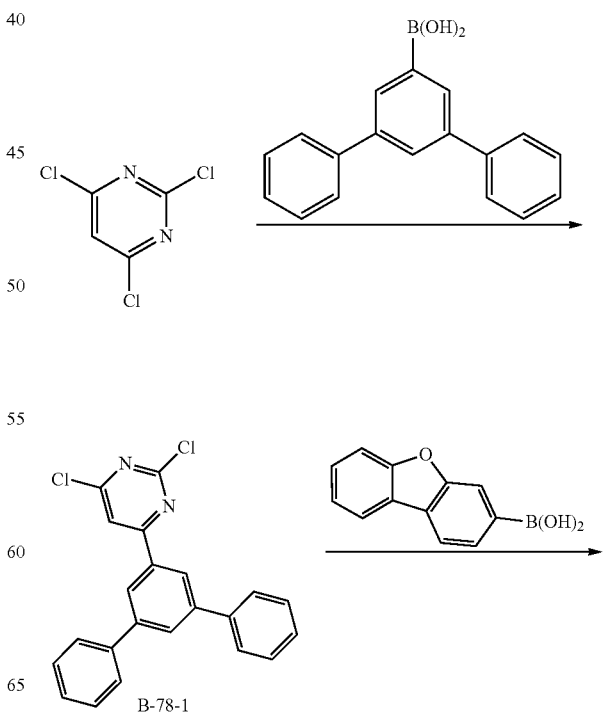

115
-continued

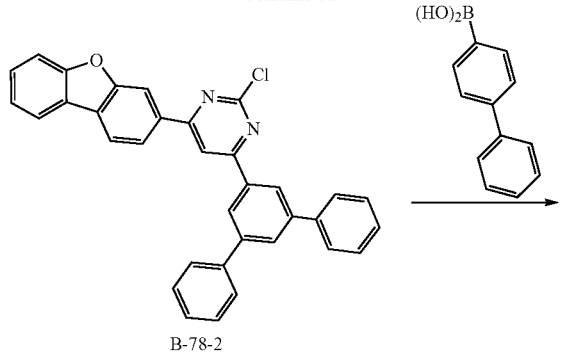

a) Synthesis of Intermediate B-78-1

Intermediate B-78-1 was synthesized according to the same method as a) of Synthesis Example 10 by using 3,5-diphenylbenzeneboronic acid instead of biphenyl-4-boronic acid.

b) Synthesis of Intermediate 8-78-2

Intermediate B-78-2 was synthesized according to the same method as a) of Synthesis Example 1 by using Intermediate B-78-1.

c) Synthesis of Compound B-78

Compound B-78 was synthesized according to the same method as b) of Synthesis Example 1 by using Intermediate B-78-2 and 1.1 equivalents of biphenyl-4-boronic acid.

LC/MS calculated for: C46H30N2O Exact Mass: 626.2358 found for 627.24 [M+H].

116

(Synthesis of Second Compound for Organic Optoelectronic Device)

Synthesis Example 12: Synthesis of Compound E-130

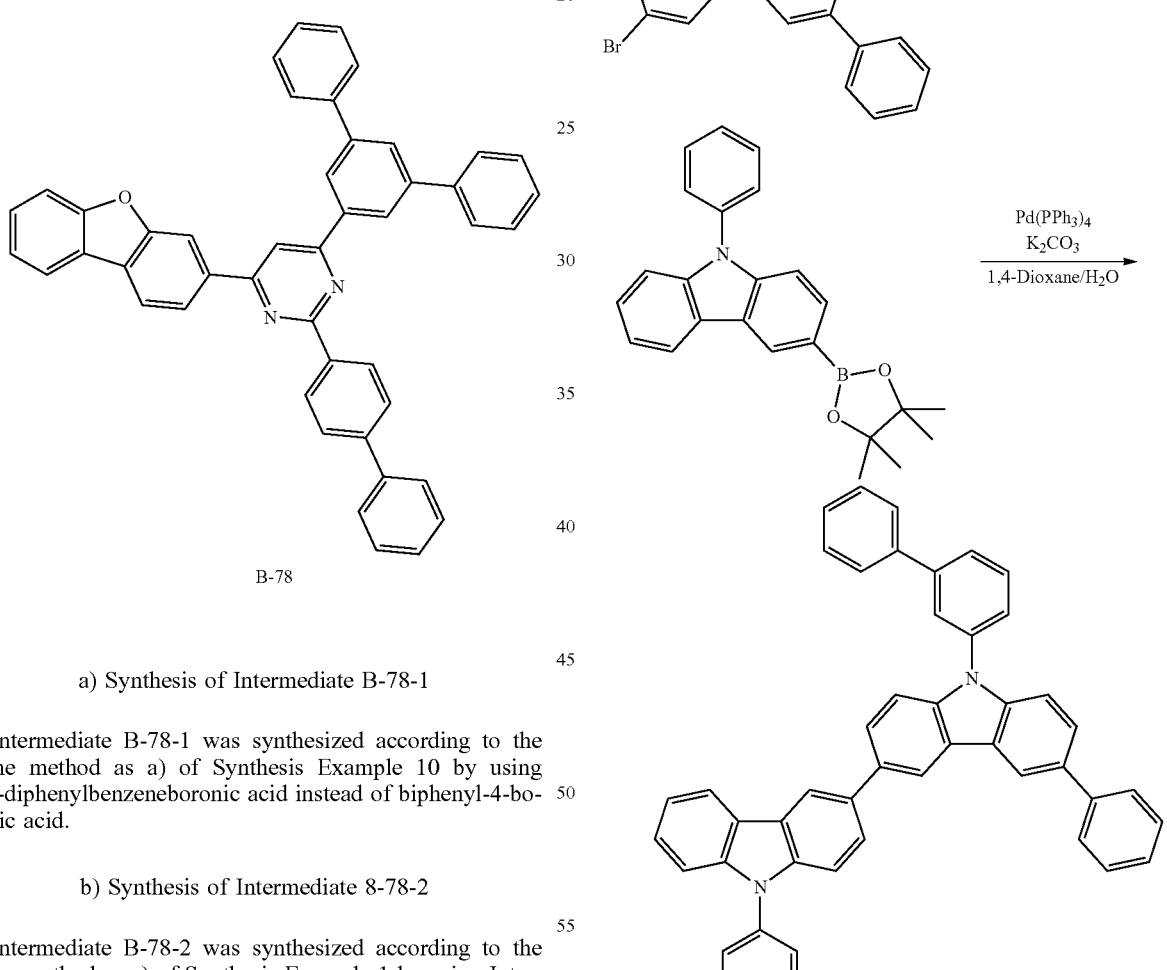

3-bromo-6-phenyl-N-metabiphenylcarbazole (20.00 g, 42.16 mmol) and N-phenylcarbazole-3-boronic ester (17.12 g, 46.38 mmol) were mixed with a mixture of tetrahydrofuran:toluene (1:1, 175 mL) and a 2 M-potassium carbonate aqueous solution (75 mL) under a nitrogen atmosphere in a 500 mL round-bottomed flask equipped with an agitator, tetrakistriphenylphosphinepalladium (0) (1.46 g, 1.26 mmol) was added thereto, and the obtained mixture was heated and refluxed under a nitrogen flow for 12 hours. When the reaction was complete, the reactants were poured into methanol, and a solid produced therein was filtered, sufficiently washed with water and methanol, and dried. The resulting material was dissolved in chlorobenzene (700 mL) through heating, the solution was silica gel-filtered, and after completely removing a solvent therefrom, a solid obtained therefrom was dissolved in chlorobenzene (400 mL) through heating and recrystallized to obtain Compound E-130 (18.52 g, 69%).

calcd. C42H32N2: C, 90.54; H, 5.07; N, 4.40; found: C, 90.54; H, 5.07; N, 4.40.

Synthesis Example 13: Synthesis of Compound E-137

[Reaction Scheme 13]

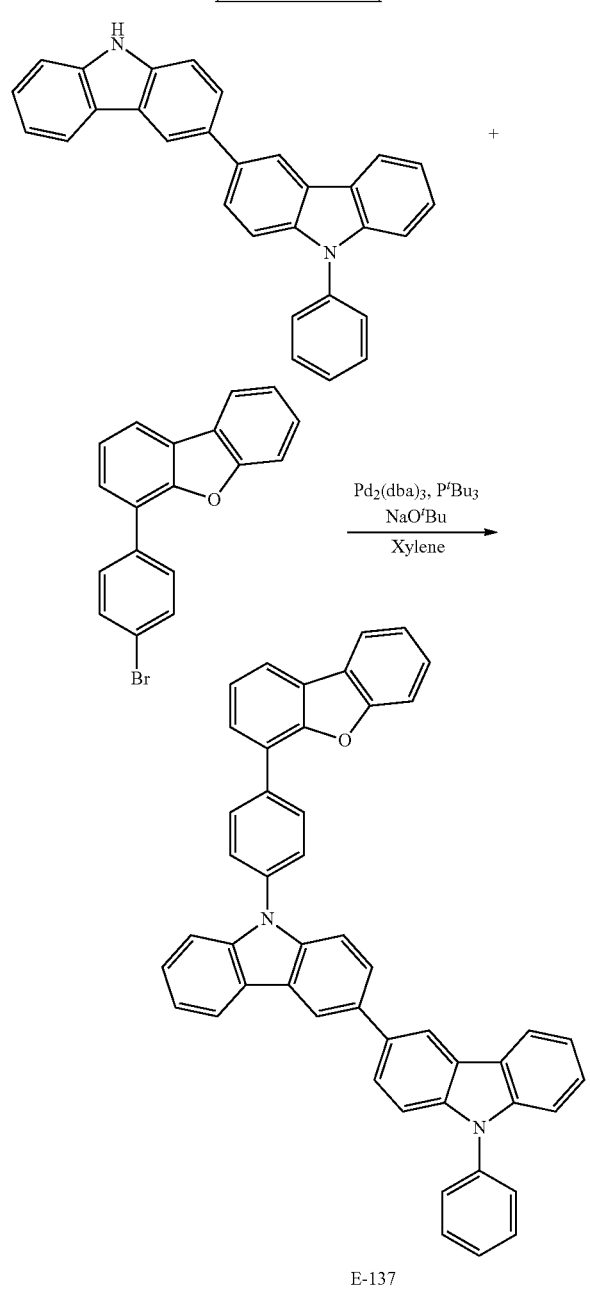

E-137

N-phenyl-3,3-bicarbazole (6.3 g, 15.4 mmol), 4-(4-bromophenyl)dibenzo[b,d]furan (5.0 g, 15.4 mmol), sodium t-butoxide (3.0 g, 30.7 mmol), tris(dibenzylideneacetone)dipalladium (0.9 g, 1.5 mmol), and tri t-butylphosphine (1.2 mL, 50% in toluene) were mixed with xylene (100 mL) in a 250 mL round flask, and the mixture was heated and refluxed under a nitrogen flow for 15 hours. The obtained mixture was added to methanol (300 mL), and a solid crystallized therein was dissolved in dichlorobenzene, filtered with silica gel/Celite, and after removing an appropriate amount of an organic solvent, recrystallized with methanol to obtain Compound E-137 (7.3 g, a yield of 73%).

calcd. C48H30N2O: C, 88.59; H, 4.65; N, 4.30; O, 2.46; found: C, 88.56; H, 4.62; N, 4.20; O, 2.43.

Comparative Synthesis Example 1: Comparative Compound 1

[Reaction Scheme 14]

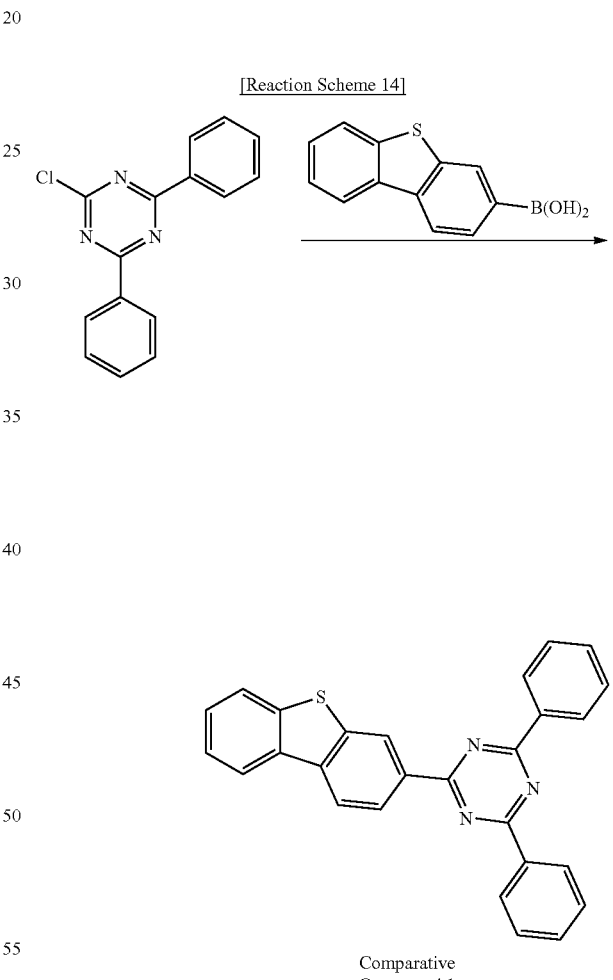

Comparative Compound 1 a) Synthesis of Comparative Compound 1

Comparative Compound 1 was synthesized according to the same method as b) of Synthesis Example 1 by using 2-chloro-4,6-diphenyltriazine and dibenzothiophene-3-boronic acid. LC/MS calculated for: C27H17N3S Exact Mass: 415.1143 found for 416.11 [M+H].

Comparative Synthesis Example 2: Comparative Compound 2

Comparative Synthesis Example 3: Synthesis of Comparative Compound 3

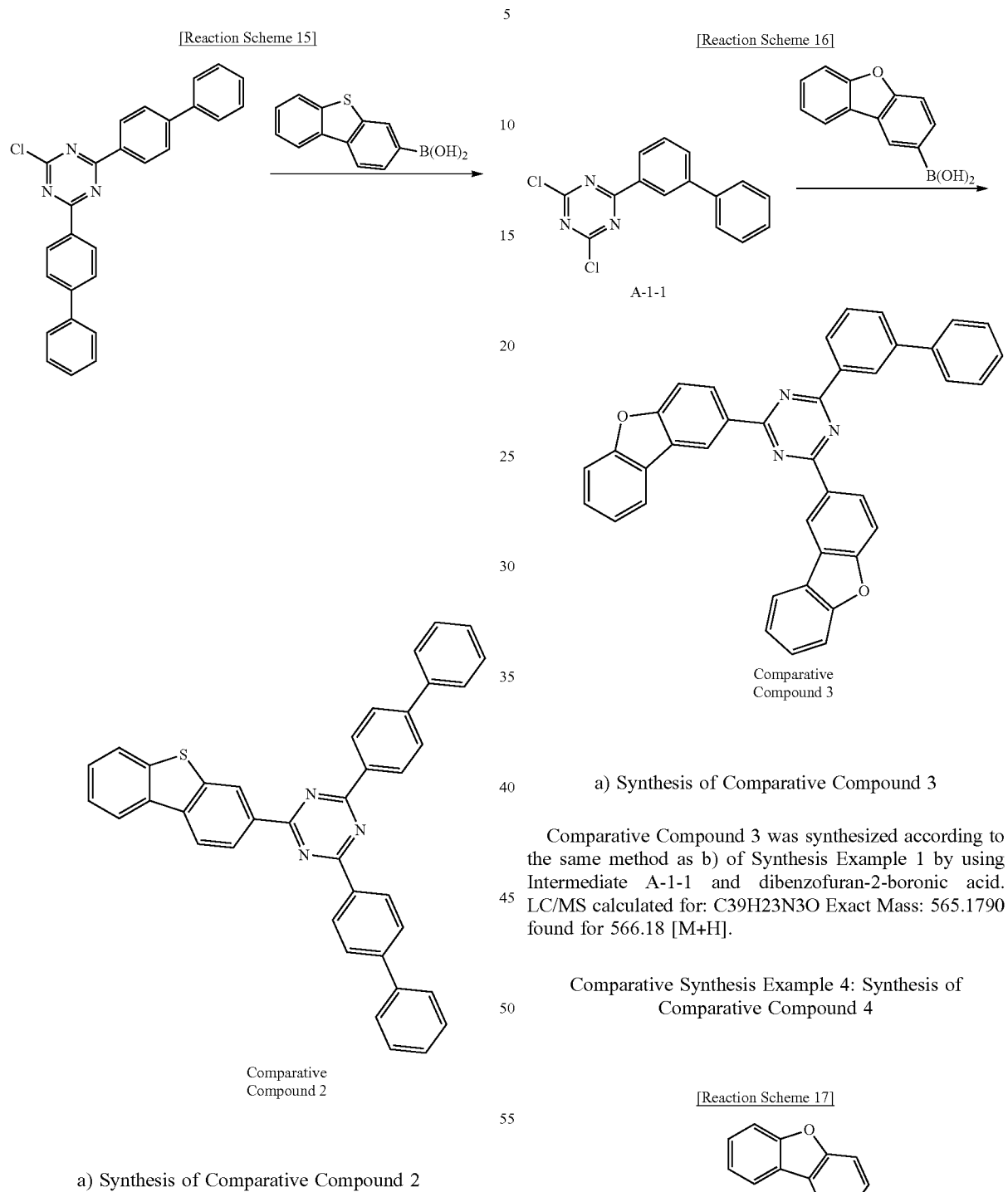

a) Synthesis of Comparative Compound 3

Comparative Compound 3 was synthesized according to the same method as b) of Synthesis Example 1 by using Intermediate A-1-1 and dibenzofuran-2-boronic acid. LC/MS calculated for: C39H23N3O Exact Mass: 565.1790 found for 566.18 [M+H].

Comparative Synthesis Example 4: Synthesis of Comparative Compound 4 a) Synthesis of Comparative Compound 2

Comparative Compound 2 was synthesized according to the same method as b) of Synthesis Example 1 by using 2,4-bis([1,1'-biphenyl]-4-yl)-6-chloro-1,3,5-triazine and dibenzothiophene-3-boronic acid. LC/MS calculated for: C39H25N3S Exact Mass: 567.1769 found for 568.18 [M+H].

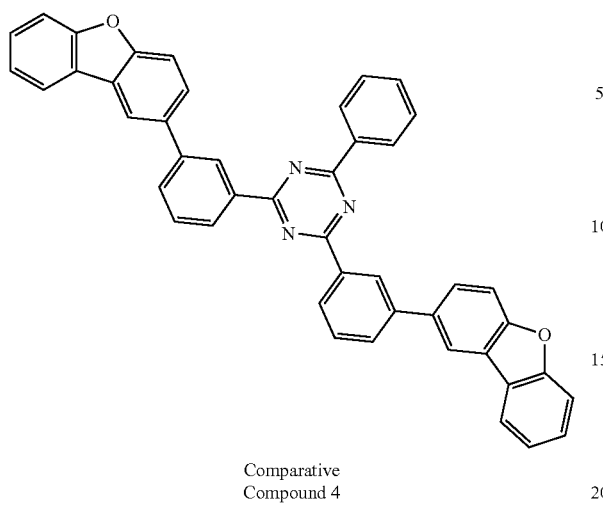

Comparative Compound 4

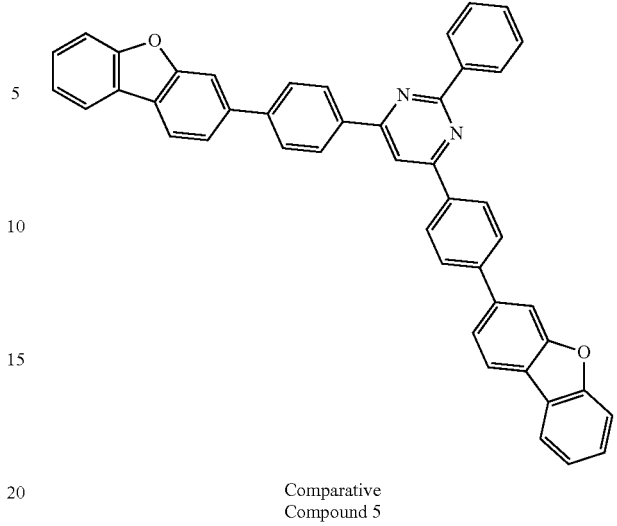

Comparative Compound 5 a) Synthesis of Comparative Compound 4

Comparative Compound 4 was synthesized according to the same method as b) of Synthesis Example 1 by using 2,4-dichloro-6-phenyl-1,3,5-triazine and dibenzofuran-2-yl-3-phenylboronic acid. LC/MS calculated for: C39H23N3O Exact Mass: 565.1790 found for 566.18 [M+H].

Comparative Synthesis Example 5: Synthesis of Comparative Compound 5

[Reaction Scheme 18]

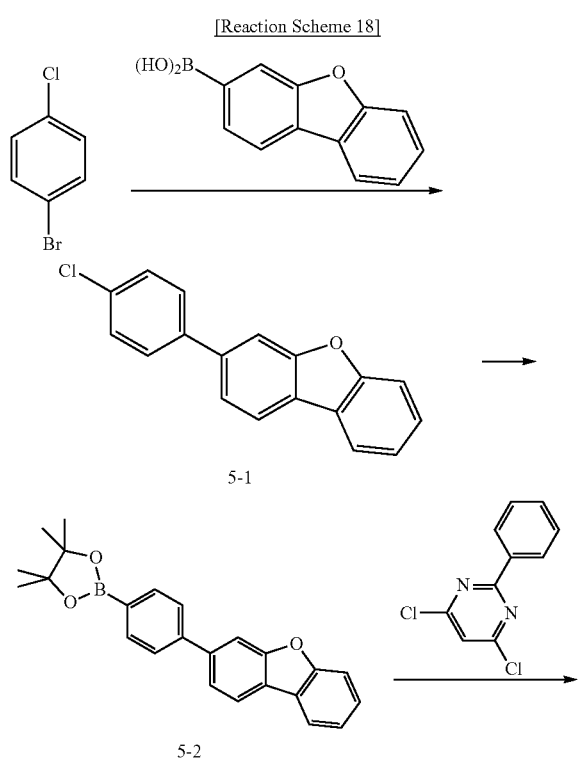

a) Synthesis of Intermediate 5-1

Intermediate 5-1 was synthesized according to the same method as b) of Synthesis Example 1 by using 1-bromo-4-chlorobenzene and dibenzofuran-3-boronic acid.

b) Synthesis of Intermediate 5-2

Intermediate 5-2 was synthesized by performing a reaction under the same condition as b) of Synthesis Example 2 by using Intermediate 5-1.

c) Synthesis of Comparative Compound 5

Comparative Compound 5 was synthesized according to the same method as b) of Synthesis Example 1 by using Intermediate 5-2 and 4,6-dichloro-2-phenyl-1,3-pyrimidine. LC/MS calculated for: C46H28N2O2 Exact Mass: 640.2151 found for 641.22 [M+H].

(Manufacture of Organic Light Emitting Diode)

Example 1

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light-emitting layer was formed on the hole transport layer by vacuum-depositing Compound B-1 of Synthesis Example 1 and Compound E-31 simultaneously as a host and 10 wt % of tris(2-phenylpyridine)iridium(III) [Ir(ppy)$_3$] as a dopant. Herein Compound B-1 and Compound E-31 were used at a weight ratio of 3:7 and in the following examples, a ratio is separately described. Subsequently, Compound D and Liq were vacuum-deposited simultaneously at a 1:1 ratio on the light-emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically ITO/compound A (700 Å)/Compound B (50 Å)/Compound C (1020 Å)/EML[compound B-1:E-31:Ir(ppy)$_3$=27 wt %:63 wt %:10 wt %] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline Example 2

An organic light emitting diode according to Example 2 was manufactured according to the same method as Example 1 by using Compound B-9 alone.

Example 3 to Example 12

Organic light emitting diodes according to Examples 3 to 12 were manufactured according to the same method as Example 1 by using first and second hosts of the present invention as shown in Tables 2 and 3.

Comparative Example 1 and 2

Organic light emitting diodes according to Comparative Examples 1 and 2 were manufactured according to the same method as Example 1 by using Comparative Compound 1 and Comparative Compound 2 respectively alone.

Comparative Example 3 to 7

Organic light emitting diodes according to Comparative Examples 3 to 7 were manufactured according to the same method as Example 1 by using each Comparative Compound 1 to Comparative Compound 5 instead of Compound B-1 of Example 1
Evaluation 1: Luminous Efficiency and Life-Span Improvement Effects
Luminous efficiency and life-span characteristics of each organic light emitting diode according to Examples 1 to 12 and Comparative Examples 1 to 7 were measured. Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Life-Span

T90 life-spans of the organic light emitting diodes according to Examples 1 to 12 and Comparative Examples 1 to 7 were measured as a time when their luminance decreased down to 90% relative to the initial luminance (cd/m$^2$) after emitting light with 5000 cd/m$^2$ as the initial luminance (cd/m$^2$) and measuring their luminance decreases depending on a time with a Polanonix life-span measurement system.

TABLE 1

Single Host Device

| | Host | Color | Efficiency Cd/A | Life-span (T90) |
|---|---|---|---|---|
| Example 2 | Compound B-9 | green | 41 | 160 |
| Comparative Example 1 | Comparative Compound 1 | green | 32 | 60 |
| Comparative Example 2 | Comparative Compound 2 | green | 33 | 40 |

Referring to Table 1, comparing Examples and Comparative Examples 1 and 2 in case of using a single host, Examples having a structural feature of additionally including a meta-substituted aryl group showed greater than or equal to 1.2 times higher efficiency and at most greater than or equal to 4 times longer life-span than Comparative Examples despite dibenzofuran linked with triazine at the same position No. 3.

TABLE 2

Mixed Host Device Effect: triazine

| | First host | Second host | First host + Second host ratio | Color | Efficiency Cd/A | Life-span T90 |
|---|---|---|---|---|---|---|
| Example 1 | Compound B-1 | Compound E-31 | 3:7 | green | 51 | 570 |
| Example 3 | Compound B-7 | Compound E-31 | 3:7 | green | 51 | 610 |
| Example 4 | Compound B-9 | Compound E-31 | 3:7 | green | 52 | 640 |
| Example 5 | Compound B-11 | Compound E-31 | 3:7 | green | 50 | 630 |
| Example 6 | Compound B-13 | Compound E-31 | 3:7 | green | 51 | 690 |
| Example 7 | Compound B-14 | Compound E-31 | 3:7 | green | 50 | 620 |

TABLE 2-continued

Mixed Host Device Effect: triazine

| | First host | Second host | First host + Second host ratio | Color | Efficiency Cd/A | Life-span T90 |
|---|---|---|---|---|---|---|
| Example 8 | Compound B-16 | Compound E-31 | 3:7 | green | 50 | 580 |
| Example 9 | Compound B-40 | Compound E-31 | 3:7 | green | 50 | 440 |
| Example 10 | Compound B-53 | Compound E-31 | 3:7 | green | 51 | 630 |
| Comparative Example 3 | Comparative Compound 1 | Compound E-31 | 3:7 | green | 48 | 160 |
| Comparative Example 4 | Comparative Compound 2 | Compound E-31 | 3:7 | green | 46 | 240 |
| Comparative Example 5 | Comparative Compound 3 | Compound E-31 | 3:7 | green | 46 | 130 |
| Comparative Example 6 | Comparative Compound 4 | Compound E-31 | 3:7 | green | 50 | 290 |

TABLE 3

Mixed Host Device Effect: pyrimidine

| | First host | Second host | First host + Second host ratio | Color | Efficiency Cd/A | Life-span (T90) |
|---|---|---|---|---|---|---|
| Example 11 | Compound B-70 | Compound E-31 | 3:7 | green | 53 | 410 |
| Example 12 | Compound B-78 | Compound E-31 | 3:7 | green | 53 | 360 |
| Comparative Example 7 | Comparative Compound 5 | Compound E-31 | 3:7 | green | 46 | 150 |

Referring to Tables 2 and 3, Examples using first and second hosts according to the present invention and having a structural feature of having dibenzofuran linked with triazine at the position No. 3 and/or additionally including a meta-substituted aryl group showed at most 5 times longer life-span than Comparative Example using a mixed host with the same second host.

This life-span increase effect was equally obtained in the pyrimidine core as well as the triazine core. Accordingly, referring to corresponding device data, a life-span of a corresponding material in a device turned out to be improved through effects of a LUMO expansion and a cyclic fusion, when dibenzofuran or dibenzothiophene is directly linked with an ET core group.

Example 13 (Electron Transport Auxiliary Layer)

ITO (indium tin oxide) was coated to be 1500 Å thick on a glass substrate, and the coated glass substrate was ultrasonic wave-washed with a distilled water. After the washing with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. Then, a 200 Å-thick light-emitting layer was formed thereon by vacuum-depositing BH113 and BD370 (Manufacturer: SFC Inc.) as a blue fluorescent luminescent host and a dopant in a dopant concentration of 5 wt %. On the light-emitting layer, Compound B-53 was vacuum-deposited to form a 50 Å-thick electron transport auxiliary layer. The electron transport auxiliary layer may include a material represented by Chemical Formula 1 alone or as a mixture of the compounds of Group 2. On the electron transport auxiliary layer, a 300 Å-thick electron transport layer was formed by vacuum-depositing Compound D and Liq simultaneously in a weight ratio of 1:1, and on the electron transport layer, a cathode was formed by sequentially vacuum-depositing Liq to be 15 Å thick and Al to be 1200 Å thick, manufacturing an organic light emitting diode. The organic light emitting diode had a structure of 5 organic thin film layers and specifically, ITO/Compound A (700 Å)/Compound B (50 Å)/Compound C (1020 Å)/EML[BH113:BD370=95:5 (wt:wt)] (200 Å)/Compound B-53 (50 Å)/Compound D:Liq (300 Å)=1:1/ Liq (15 Å)/Al (1200 Å).

Compound A: N4,N4'-diphenyl-N4,N4'-bis(9-phenyl-9H-carbazol-3-yl)biphenyl-Compound B: 1,4,5,8,9,11-hexaaza-triphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

Comparative Example 8

An organic light emitting diode was manufactured according to the same method as Example 12 except for using Comparative Compound 1.

Evaluation 2

Current density change, luminance change, and luminous efficiency depending on a voltage of each organic light emitting diode according to Example 13 and Comparative Example 8 were measured.

Specific measurement methods are the same as in Evaluation 1, a method of measuring life-span is as follows, and the results are shown in Table 4.

[Measurement of Life-Span]

T97 life-spans of the organic light emitting diodes according to Example 12, Example 13, and Comparative Example 8 were measured as a time when their luminance decreased down to 97% relative to the initial luminance (cd/m$^2$) after emitting light with 750 cd/m$^2$ as the initial luminance (cd/m$^2$) and measuring their luminance decrease depending on a time with a Polanonix life-span measurement system.

TABLE 4

| Devices | Electron transport auxiliary layer | Luminous efficiency (cd/A) | Color coordinate (x, y) | T97(h) @750 nit |
|---|---|---|---|---|
| Example 13 | Compound B-53 | 6.9 | (0.132, 0.149) | 95 |
| Comparative Example 8 | Comparative Compound 1 | 5.9 | (0.132, 0.149) | 48 |

Referring to Table 4, the organic light emitting diode according to Example 13 showed simultaneously improved luminous efficiency and life-span characteristics compared with the organic light emitting diode according to Comparative Example 8.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device, the compound being represented by Chemical Formula 1:

[Chemical Formula 1]

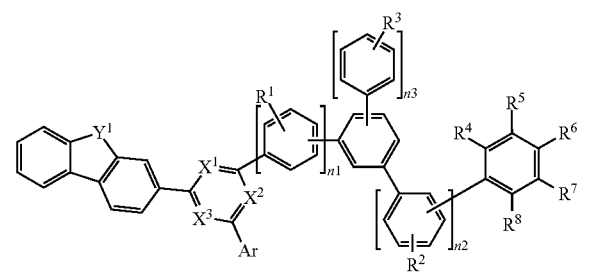

wherein, in Chemical Formula 1, $X^1$ to $X^3$ are independently N or $CR^a$, at least two of $X^1$ to $X^3$ are N, $Y^1$ is O or S, Ar is a substituted or unsubstituted C6 to C30 aryl group, $R^a$ and $R^1$ to $R^3$ are independently hydrogen, deuterium, a substituted or unsubstituted C1 to C10 alkyl group, a substituted or unsubstituted C6 to C30 aryl group, or a combination thereof, $R^4$ to $R^8$ are independently hydrogen, deuterium, a cyano group, a nitro group, a substituted or unsubstituted C1 to C10 alkyl group, a substituted or unsubstituted C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group, or adjacent groups thereof are linked with each other to provide a heteroaromatic polycyclic ring represented by Chemical Formula A,

[Chemical Formula A]

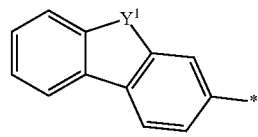

$Y^2$ is O or S, n1 to n3 are independently an integer of 0 to 2, in case of n1+n2+n3=0, adjacent groups of $R^4$ to $R^8$ are linked with each other to provide the heteroaromatic polycyclic ring represented by Chemical Formula A, and the "substituted" refers to replacement of at least one hydrogen by deuterium, a C1 to C20 alkyl group, a C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group.

2. The compound for an organic optoelectronic device of claim 1, wherein the compound is represented by one of Chemical Formula 1-I, Chemical Formula 1-II, and Chemical Formula 1-III:

[Chemical Formula 1-I]

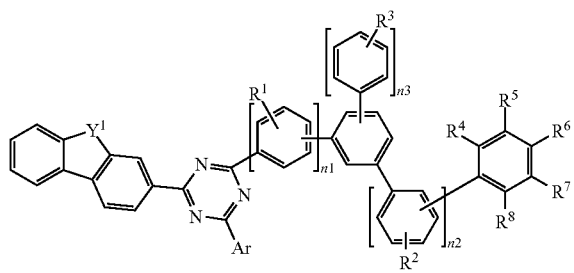

[Chemical Formula 1-1]

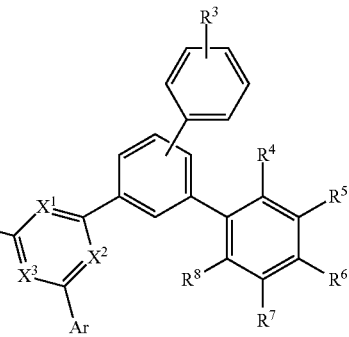

[Chemical Formula 1-2]

[Chemical Formula 1-II]

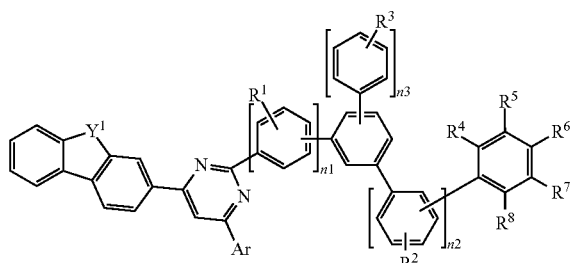

[Chemical Formula 1-3]

[Chemical Formula 1-III]

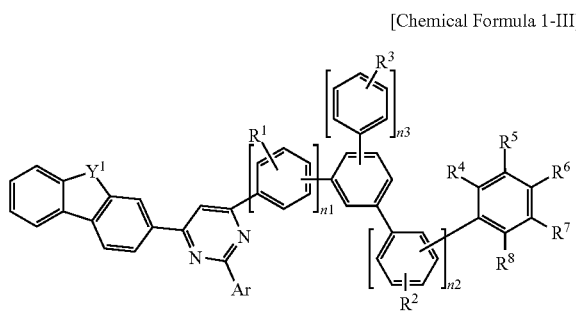

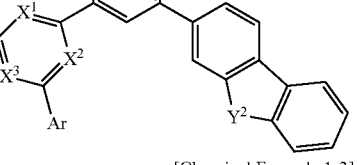

[Chemical Formula 1-4]

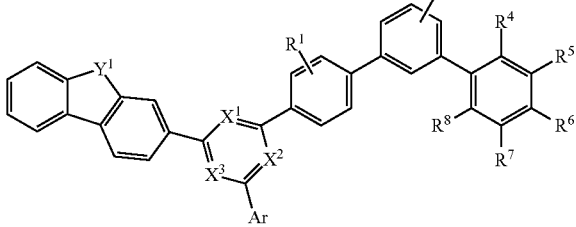

[Chemical Formula 1-5]

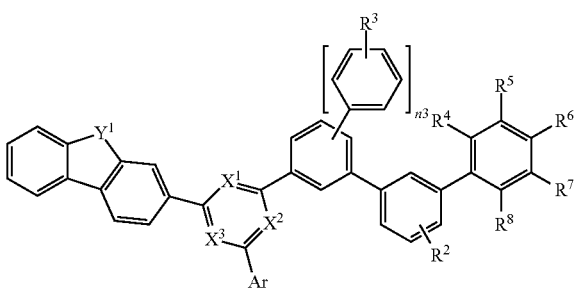

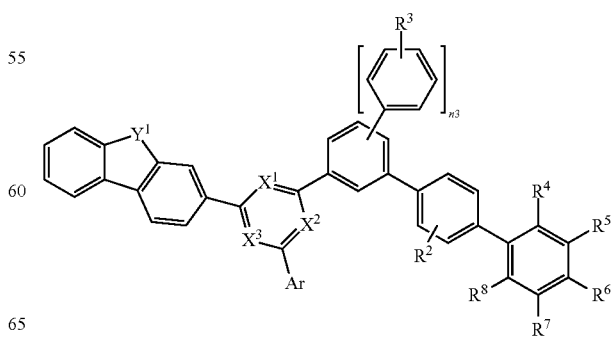

wherein, in Chemical Formula 1-I, Chemical Formula 1-II, and Chemical Formula 1-III, $Y^1$ is O or S, Ar is a substituted or unsubstituted C6 to C30 aryl group, $R^1$ to $R^3$ are independently hydrogen, deuterium, a substituted or unsubstituted C1 to C10 alkyl group, a substituted or unsubstituted C6 to C30 aryl group, or a combination thereof, $R^4$ to $R^8$ are independently hydrogen, deuterium, a cyano group, a nitro group, a substituted or unsubstituted C1 to C10 alkyl group, a substituted or unsubstituted C6 to C30 aryl group, a substituted or unsubstituted pyridinyl group, a substituted or unsubstituted quinolinyl group, a substituted or unsubstituted isoquinolinyl group, a substituted or unsubstituted dibenzofuranyl group, or a substituted or unsubstituted dibenzothiophenyl group, or adjacent groups thereof are linked with each other to provide the heteroaromatic polycyclic ring represented by Chemical Formula A, n1 to n3 are independently an integer of 0 to 2, and in case of n1+n2+n3=0, adjacent groups of $R^4$ to $R^8$ are linked with each other to provide the heteroaromatic polycyclic ring represented by Chemical Formula A.

3. The compound for an organic optoelectronic device of claim 1, wherein the compound is represented by one of Chemical Formulae 1-1 to 1-6:

wherein, in Chemical Formulae 1-1 to 1-5,
$X^1$ to $X^3$ are independently N or CH,
at least two of $X^1$ to $X^3$ are N,
$R^1$ to $R^3$ are independently hydrogen, deuterium, a substituted or unsubstituted phenyl group, a substituted or unsubstituted biphenyl group, a substituted or unsubstituted naphthyl group, or a combination thereof,
$R^4$ to $R^8$ are independently hydrogen, deuterium, a cyano group, a nitro group, a substituted or unsubstituted phenyl group, a substituted or unsubstituted biphenyl group, a dibenzofuranyl group, or a dibenzothiophenyl group, or adjacent groups thereof are linked with each other to provide the heteroaromatic polycyclic ring represented by Chemical Formula A,
$Y^1$ is O or S,
Ar is a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted fluorenyl group, or a combination thereof,
n3 is an integer of 0 or 1, and
is a linking point with a substituted or unsubstituted phenylene.

4. The compound for an organic optoelectronic device of claim 1, wherein;
$R^1$ to $R^3$ are independently hydrogen, deuterium, or a substituted or unsubstituted phenyl group,
$R^4$ to $R^8$ are independently hydrogen, deuterium, a substituted or unsubstituted phenyl group, or a substituted or unsubstituted biphenyl group, or adjacent groups thereof are linked with each other to provide the heteroaromatic polycyclic ring represented by Chemical Formula A, and
Ar is a substituted or unsubstituted phenyl group, a substituted or unsubstituted biphenyl group, a substituted or unsubstituted terphenyl group, or a substituted or unsubstituted naphthyl group.

5. The compound for an organic optoelectronic device of claim 1, wherein the compound is selected from compounds of Group 1:

[Group 1]

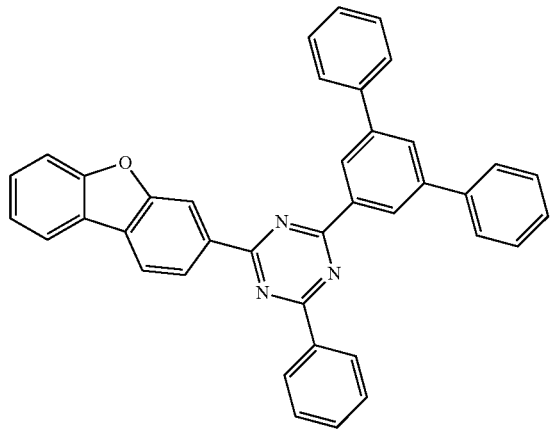

[B-1]

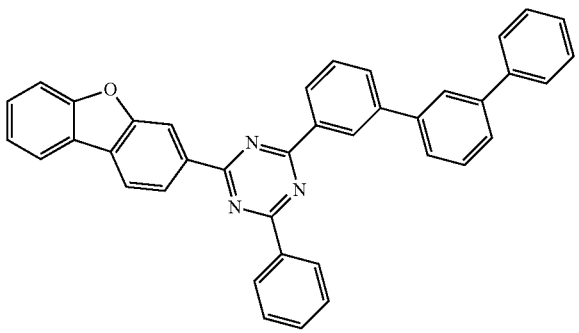

[B-2]

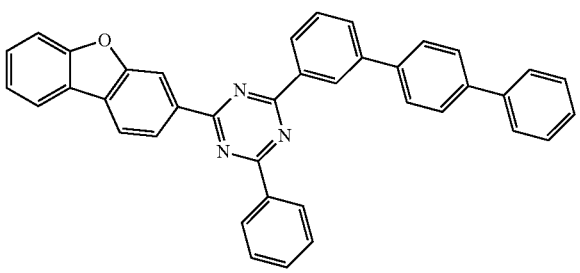

[B-3]

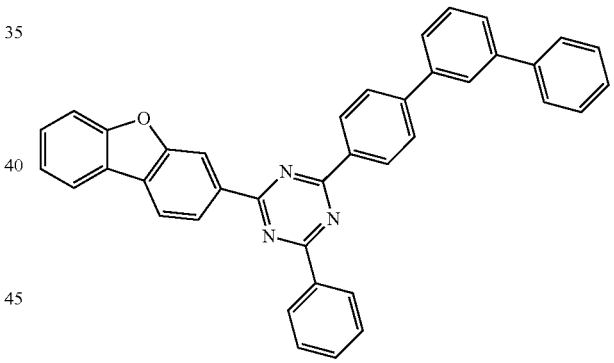

[B-4]

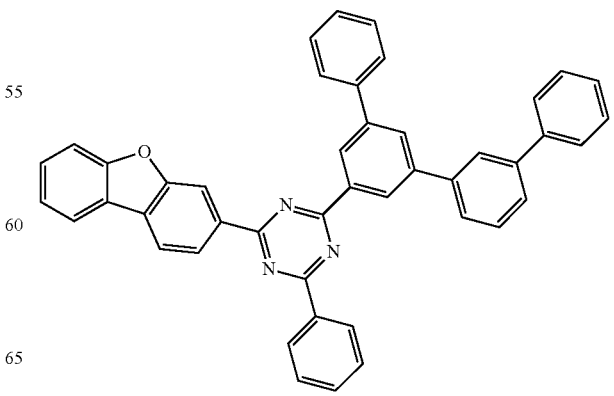

[B-5]

[B-6]
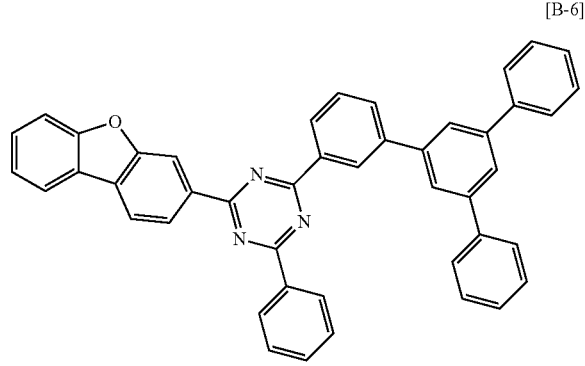
[B-10]
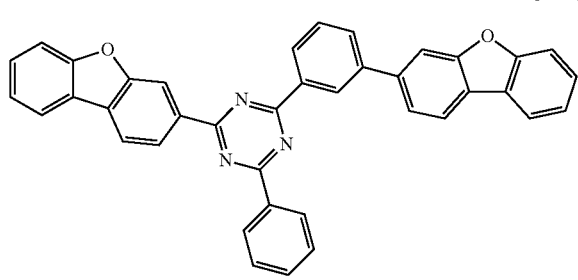
[B-7]
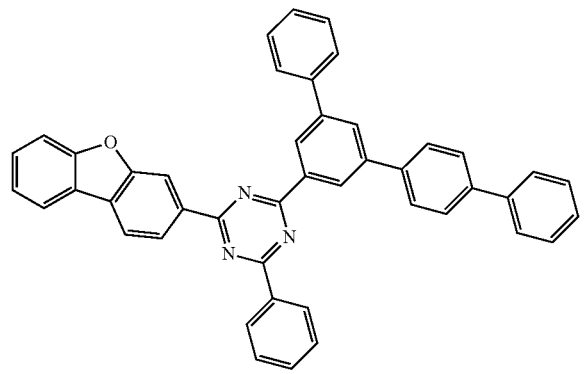
[B-11]
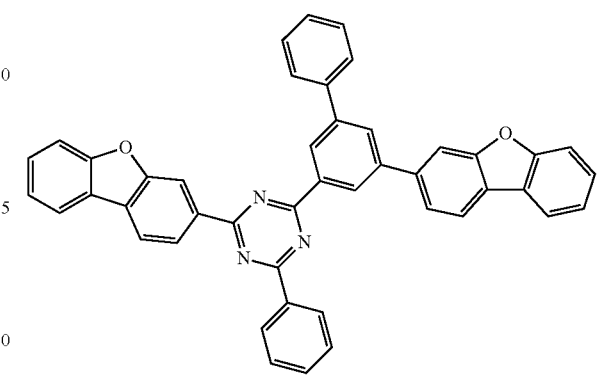
[B-8]
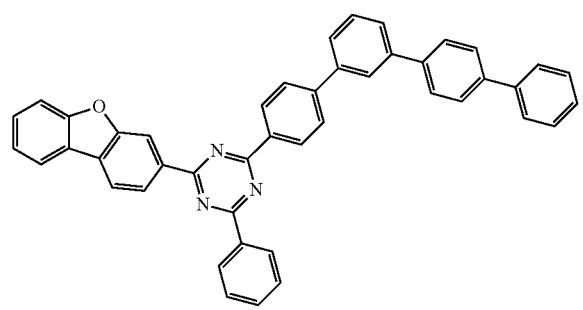
[B-12]
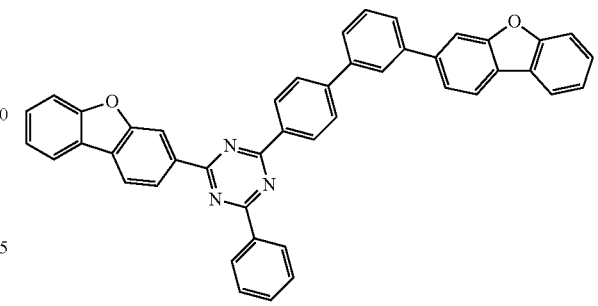
[B-9]
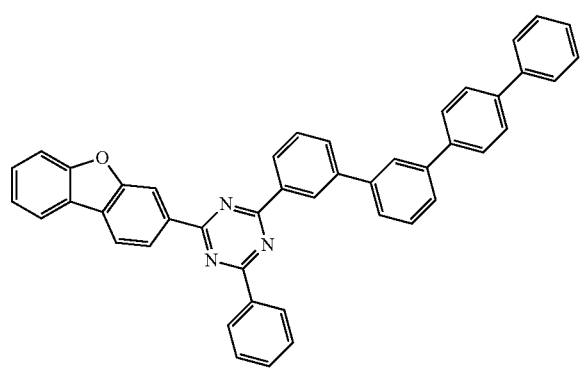
[B-13]
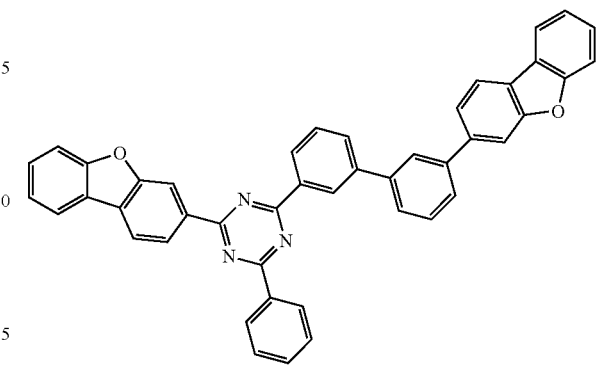

[B-14]
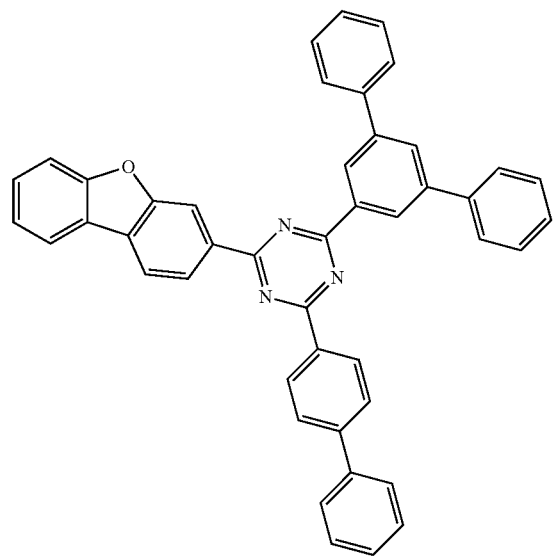
[B-15]
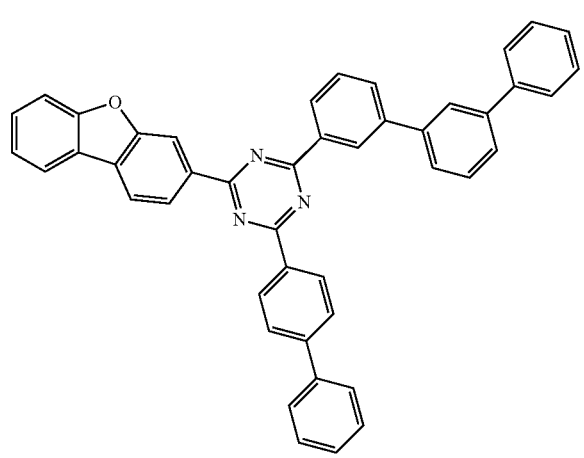
[B-16]
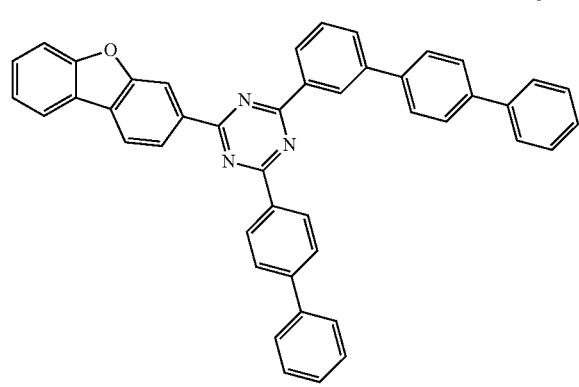
[B-17]
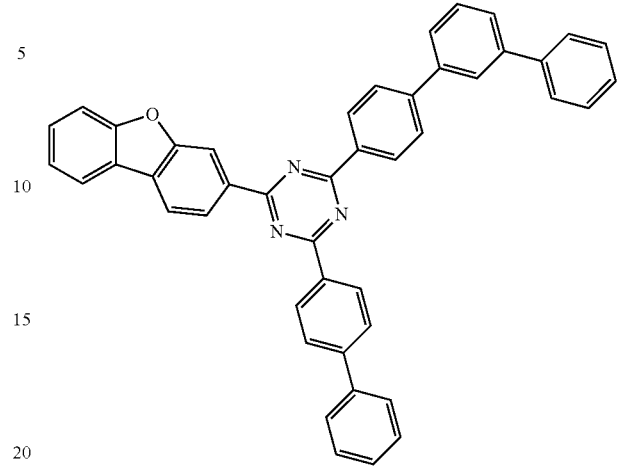
[B-18]
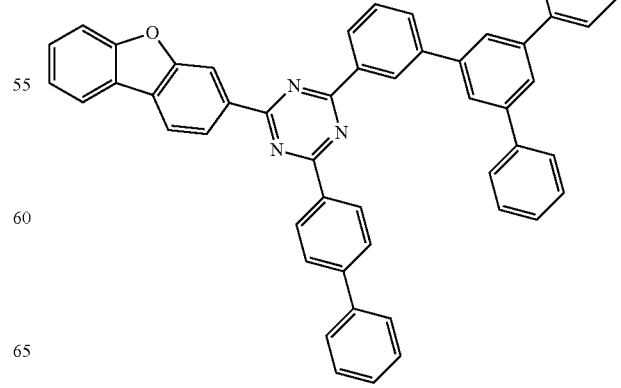
[B-19]

[B-20]
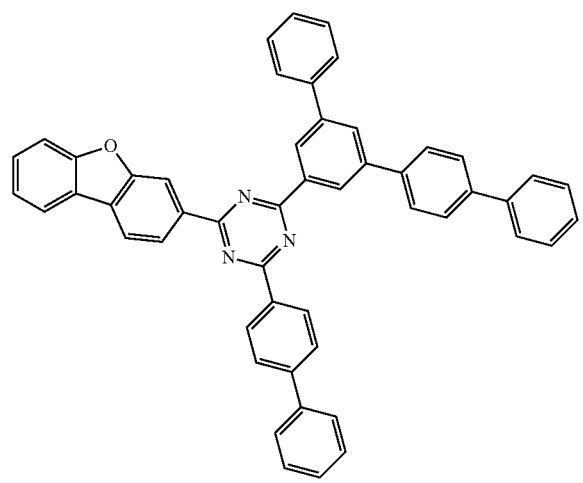
[B-23]
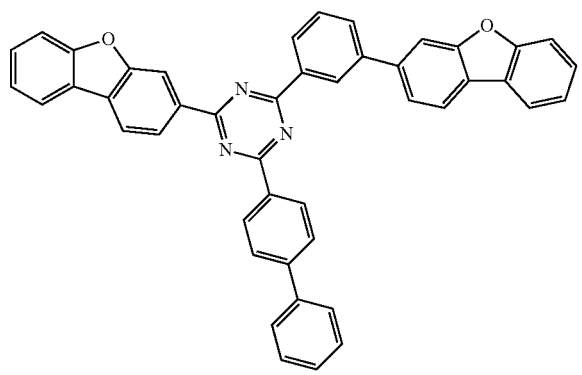
[B-21]
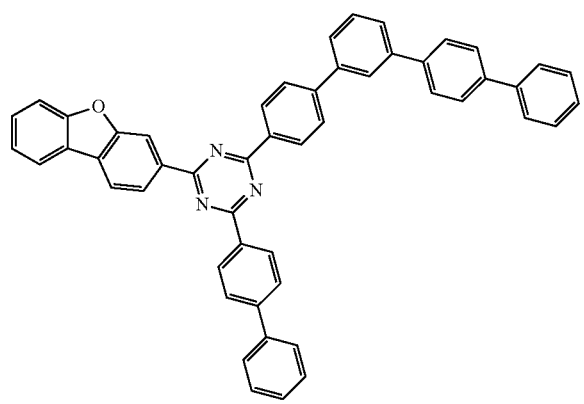
[B-24]
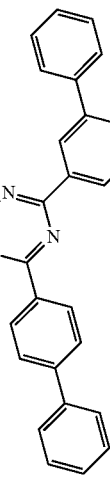
[B-22]
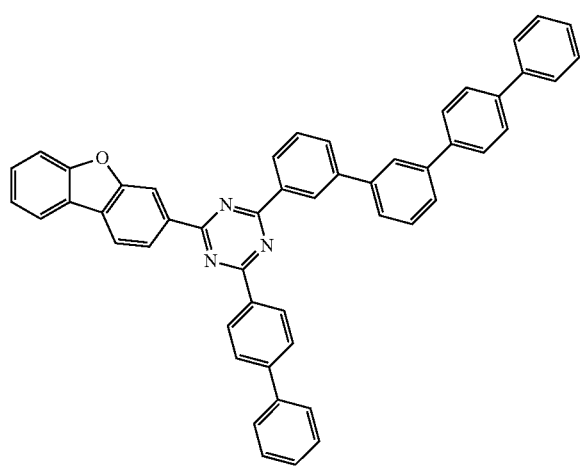
[B-25]
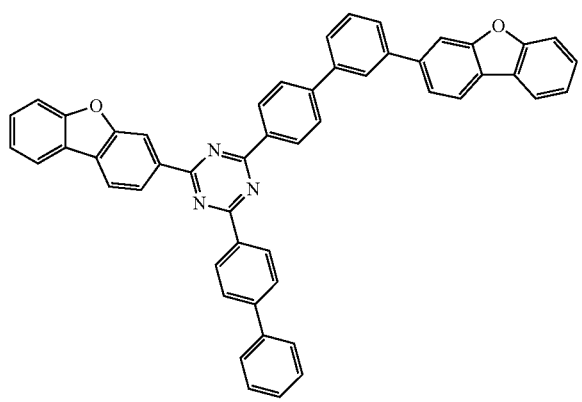

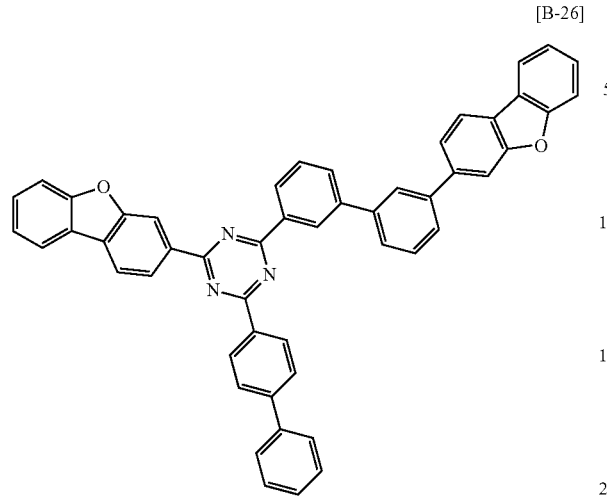
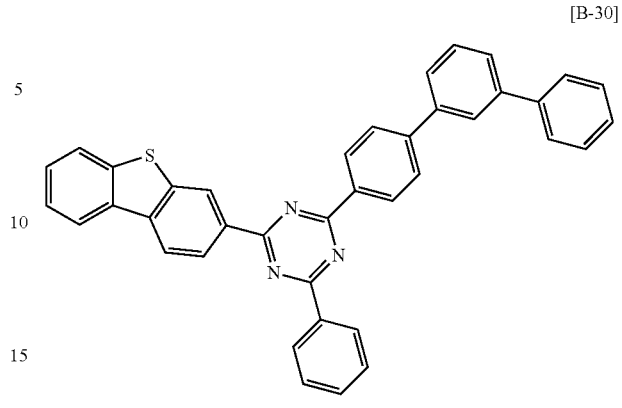

[B-34]
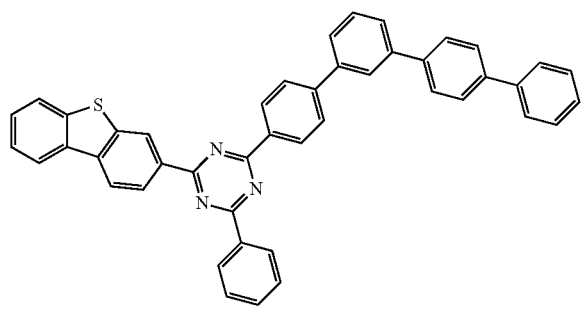
[B-38]
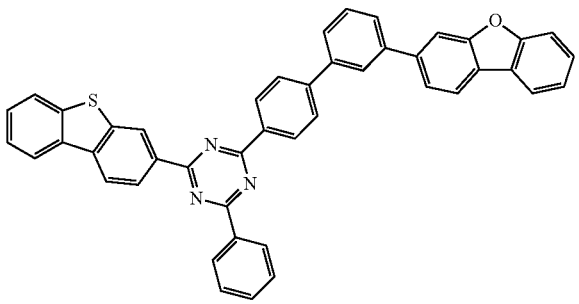
[B-35]
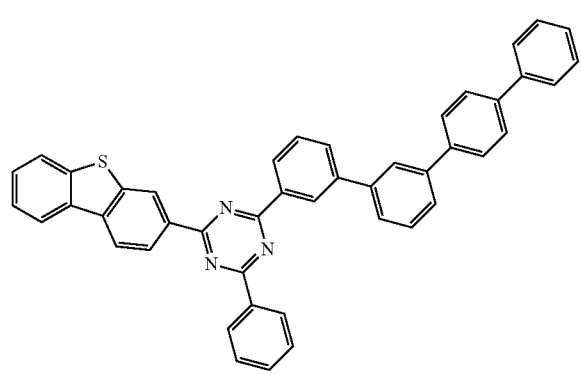
[B-39]
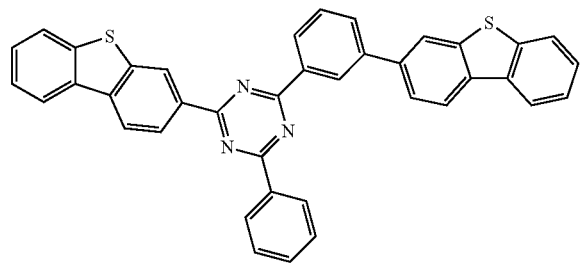
[B-36]
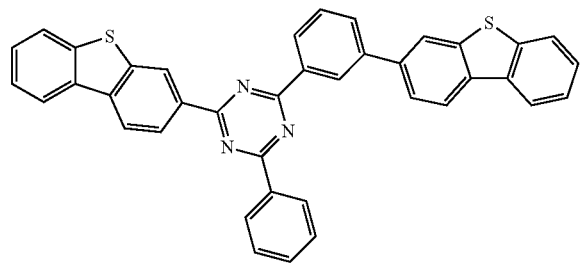
[B-40]
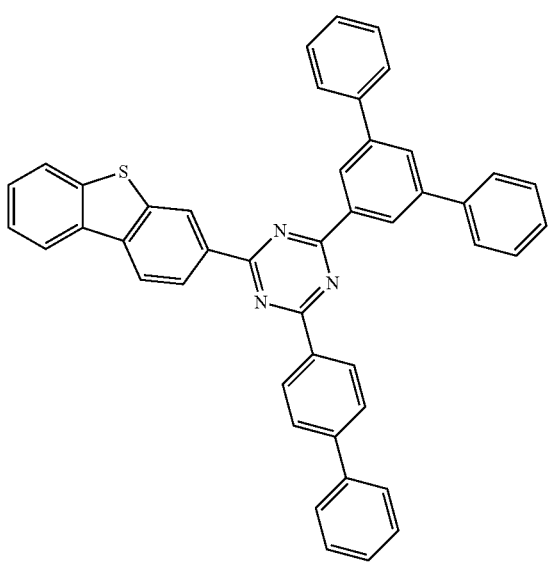
[B-37]
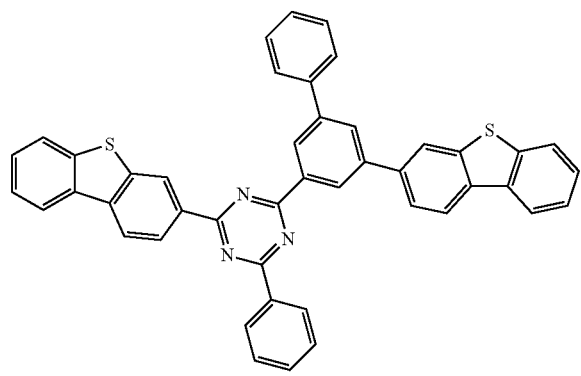

[B-41]
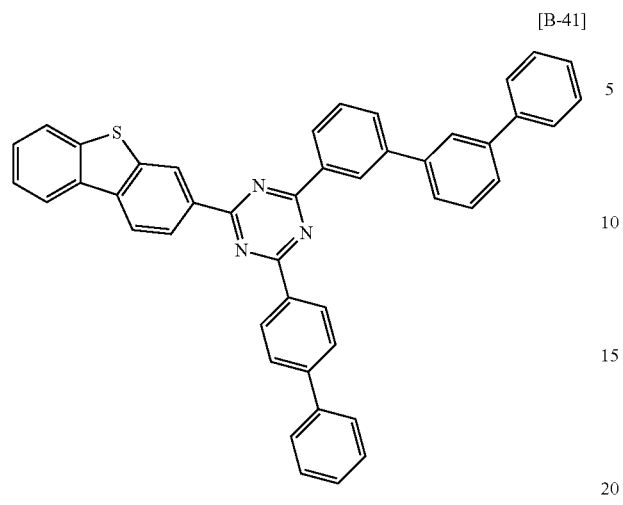
[B-44]
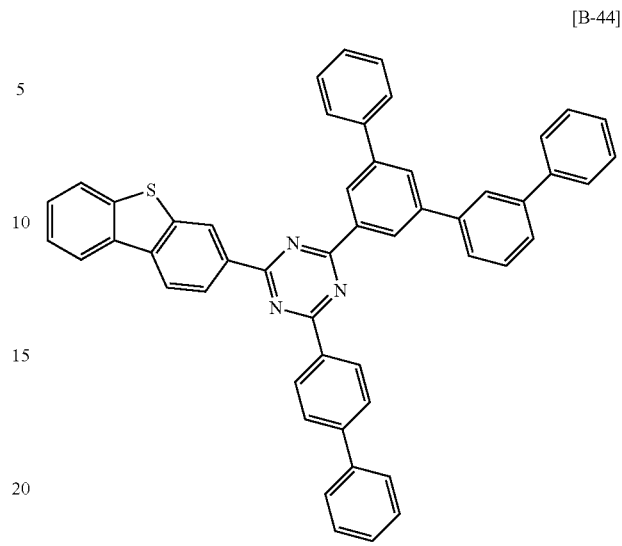
[B-42]
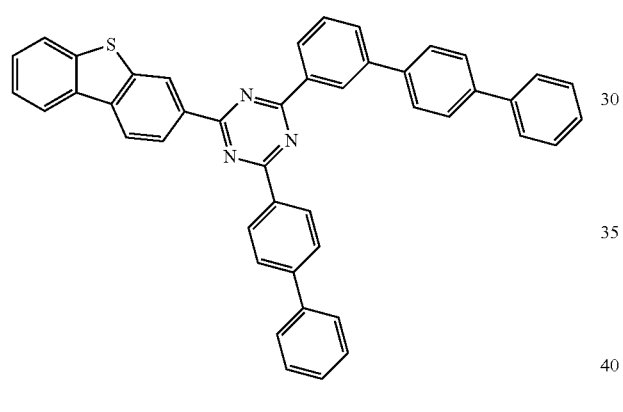
[B-45]
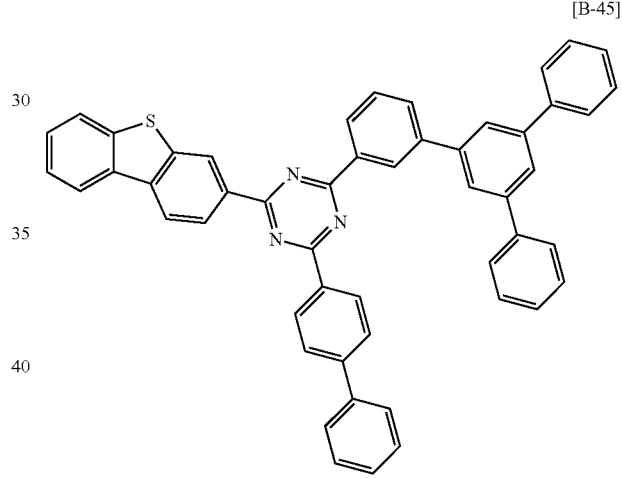
[B-43]
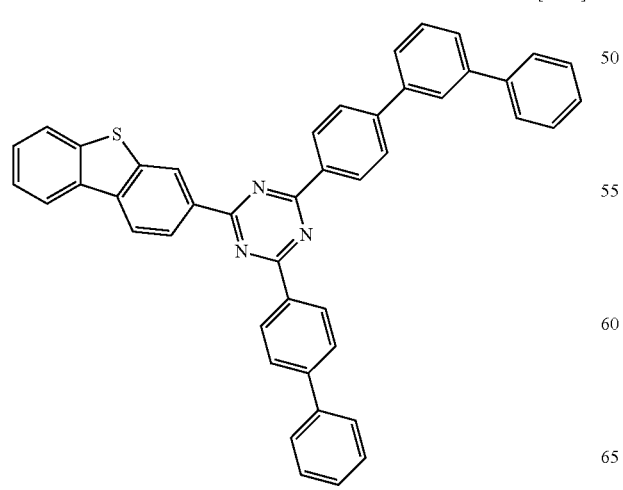
[B-46]
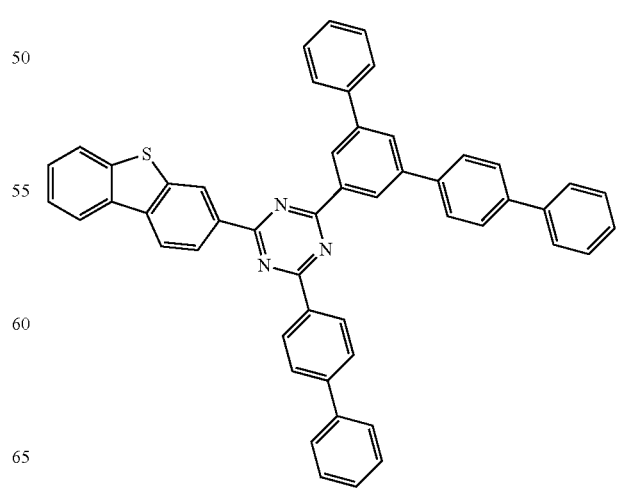

[B-47]
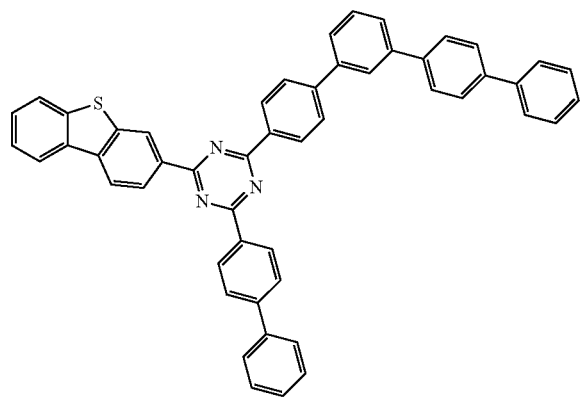
[B-50]
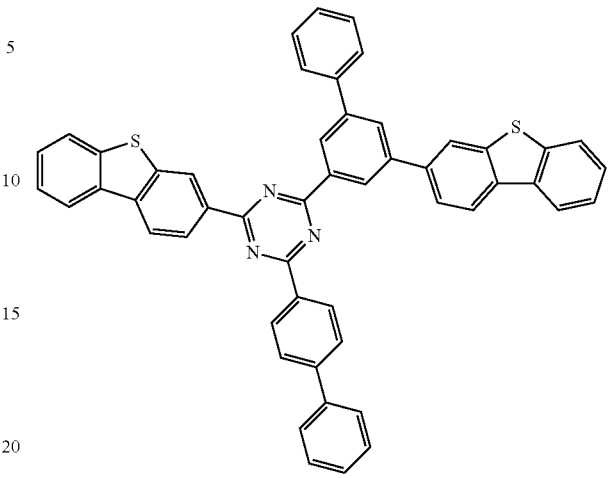
[B-48]
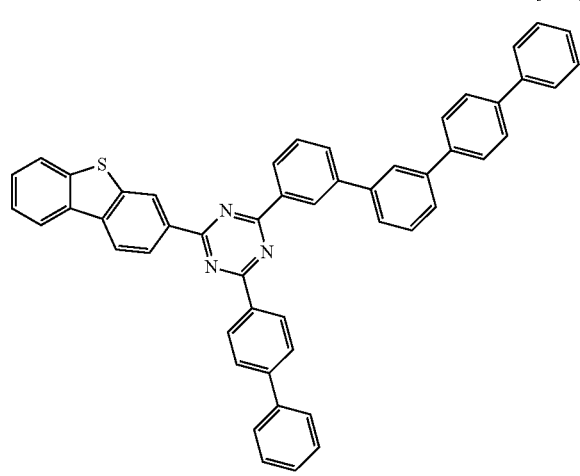
[B-51]
[B-49]
[B-52]
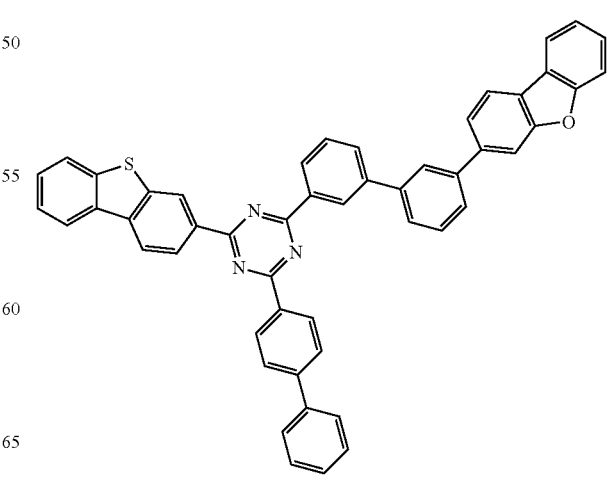

[B-53]
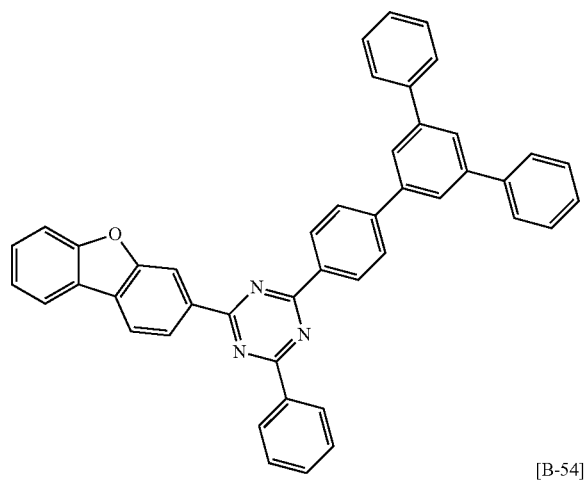
[B-56]
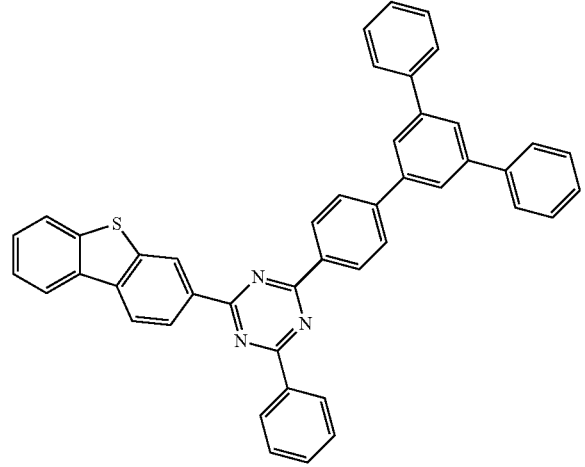
[B-54]
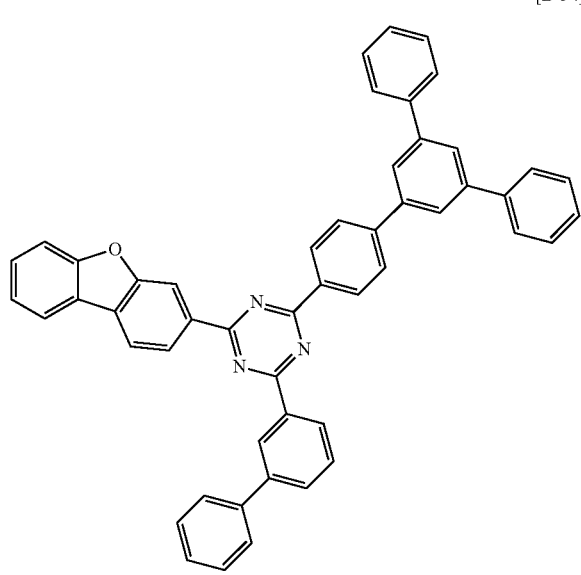
[B-57]
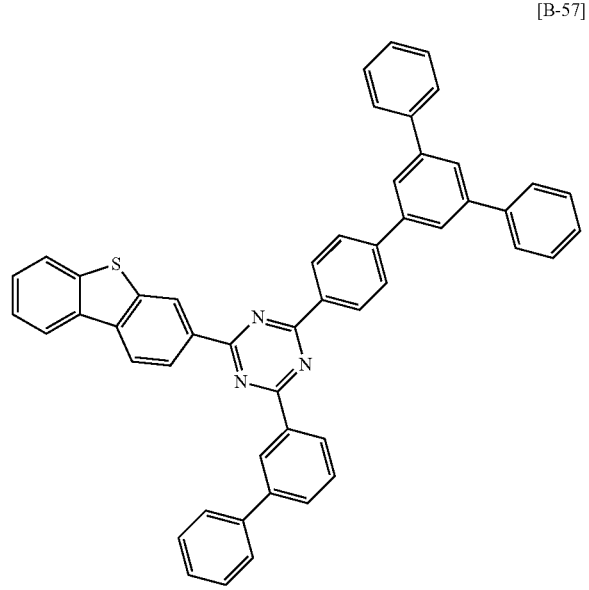
[B-55]
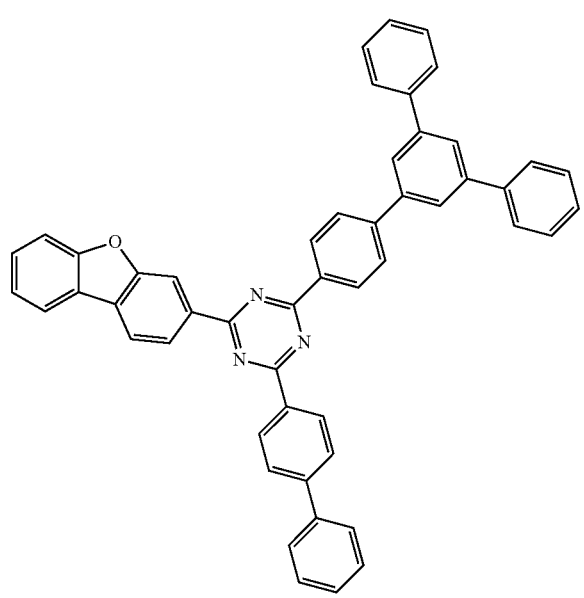
[B-58]
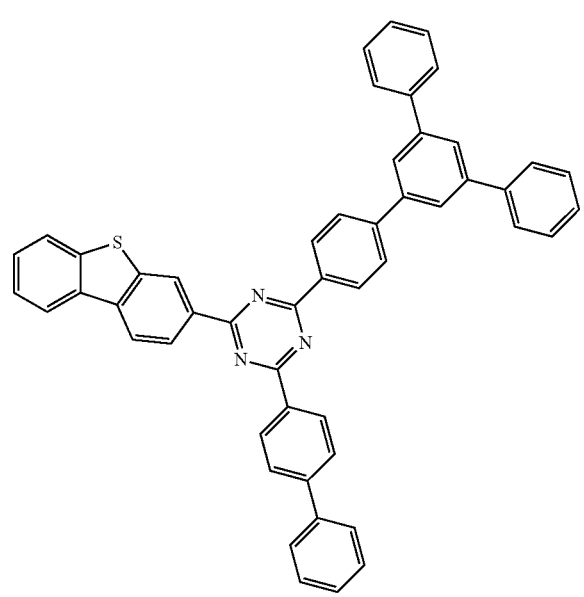

[B-59]
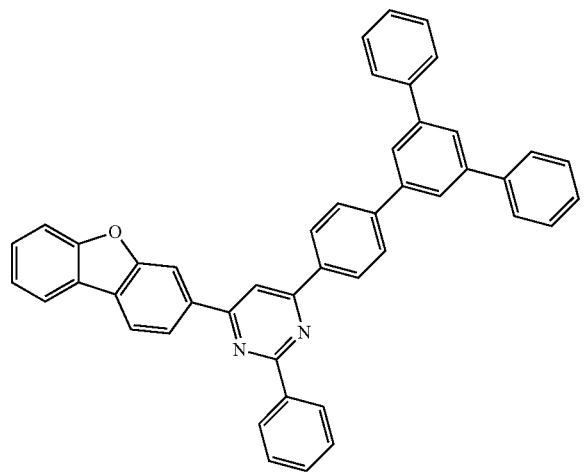
[B-60]
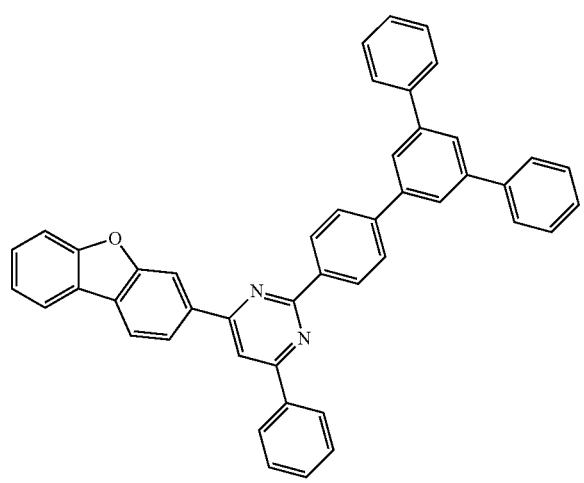
[B-61]
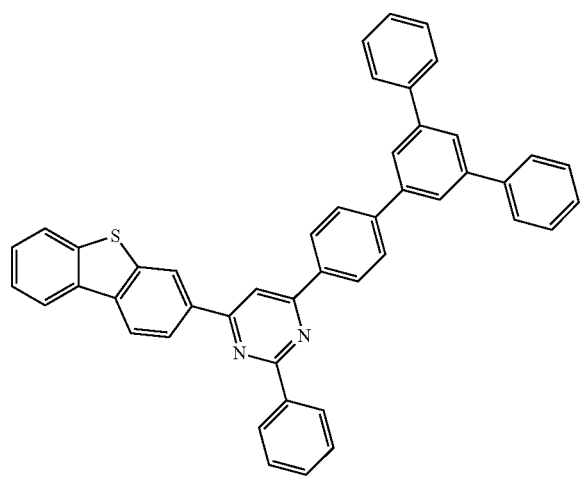
[B-62]
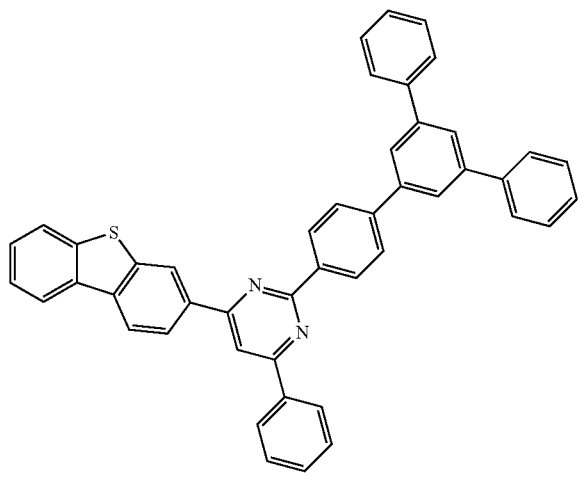
[B-63]
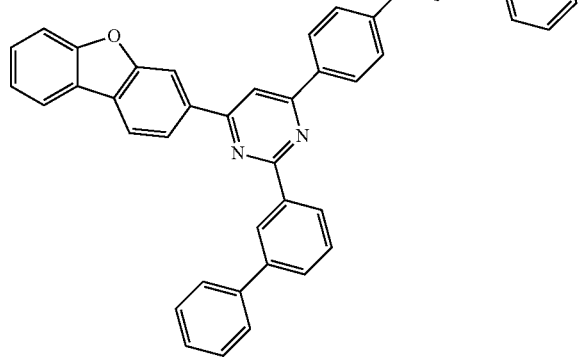
[B-64]
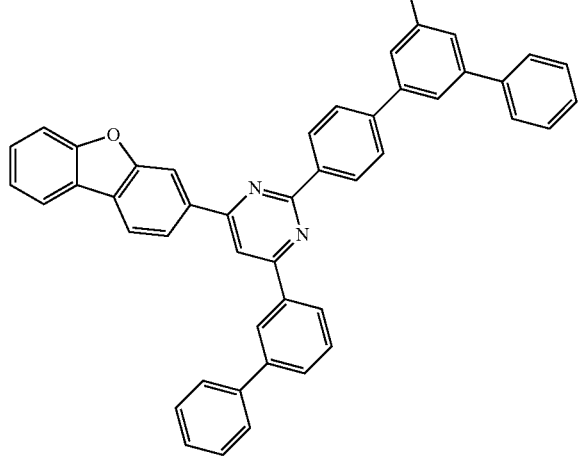

[B-65]
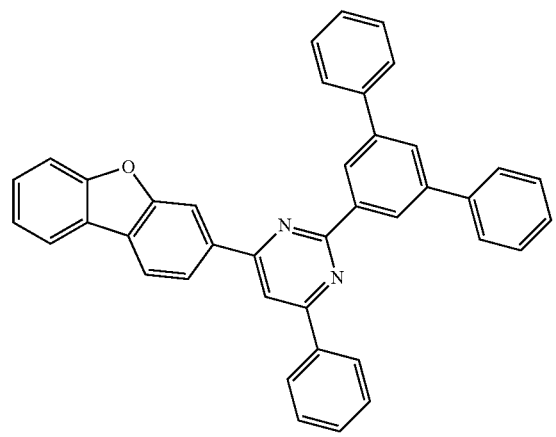
[B-66]
[B-69]
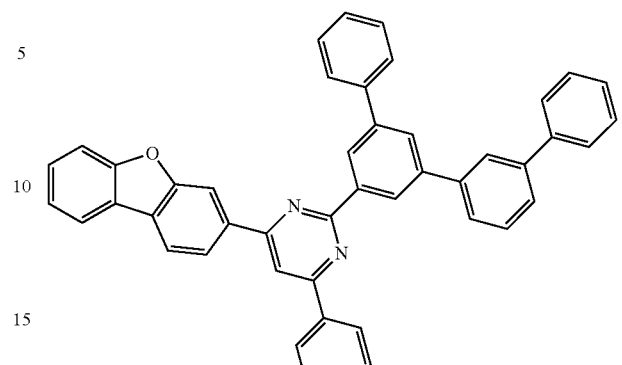
[B-67]
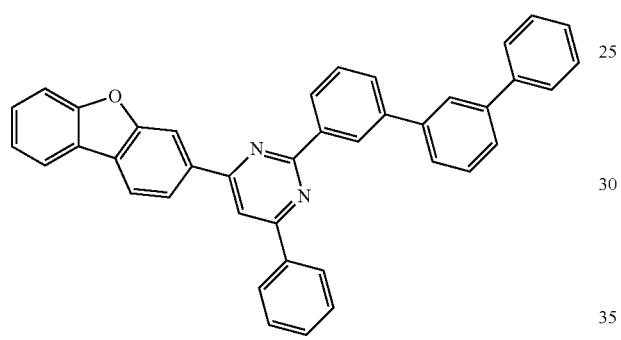
[B-70]
[B-68]
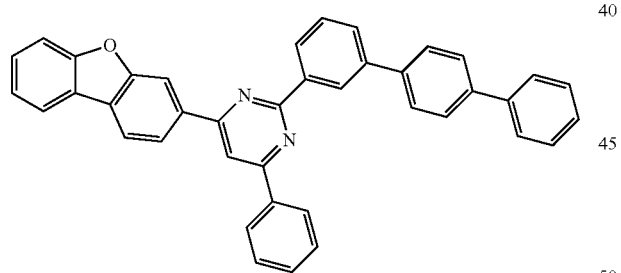
[B-71]
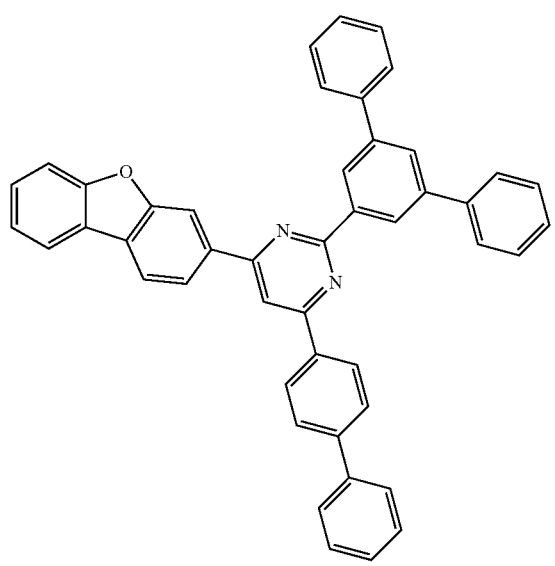
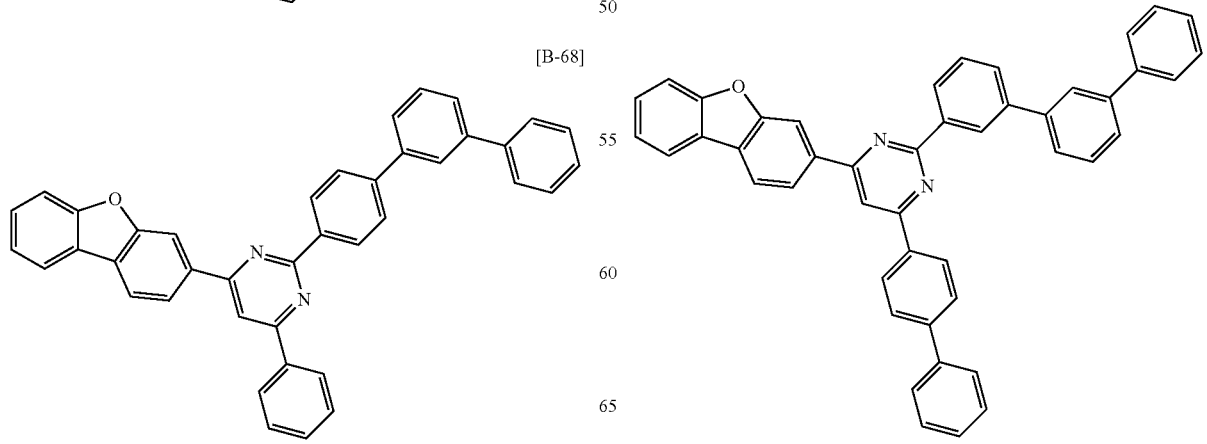

[B-72]
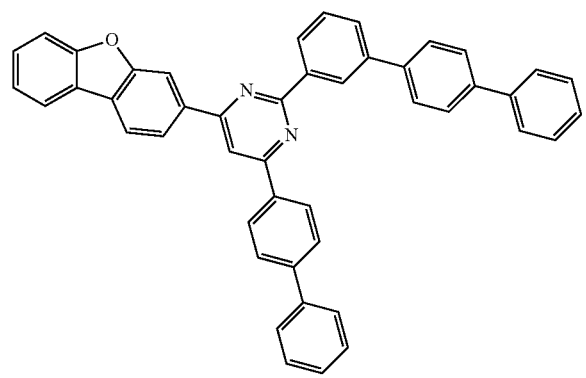
[B-73]
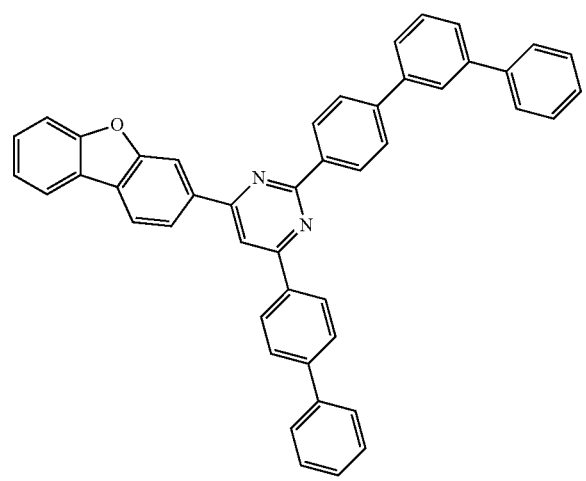
[B-74]
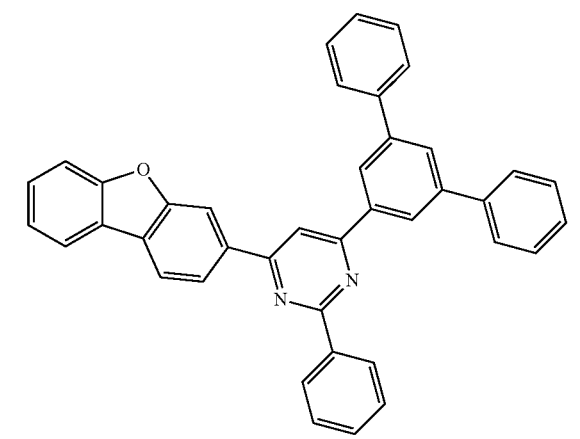
[B-75]
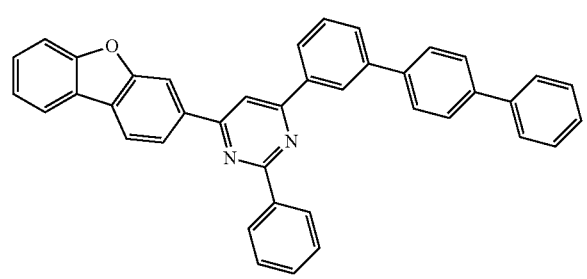
[B-76]
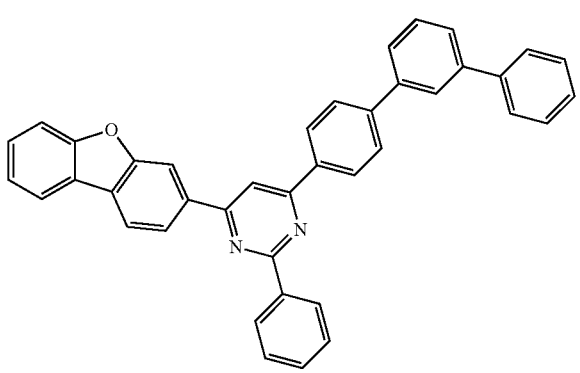
[B-77]
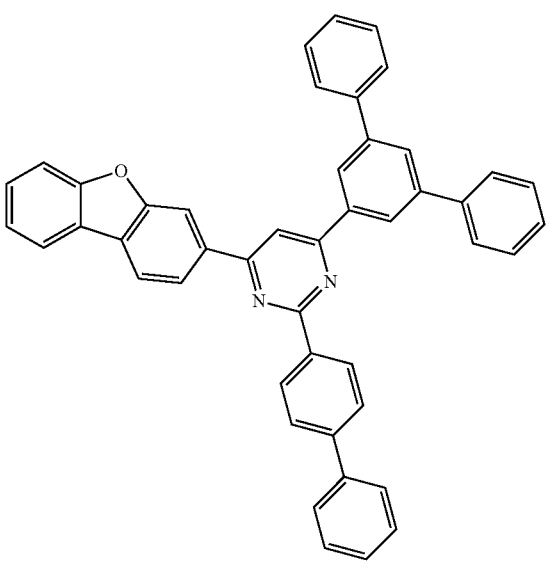
[B-78]

[B-79]

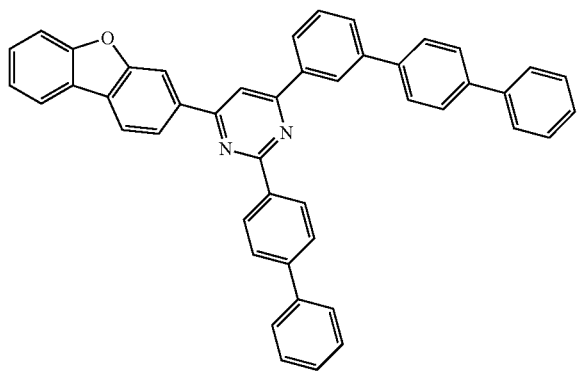

[B-80]

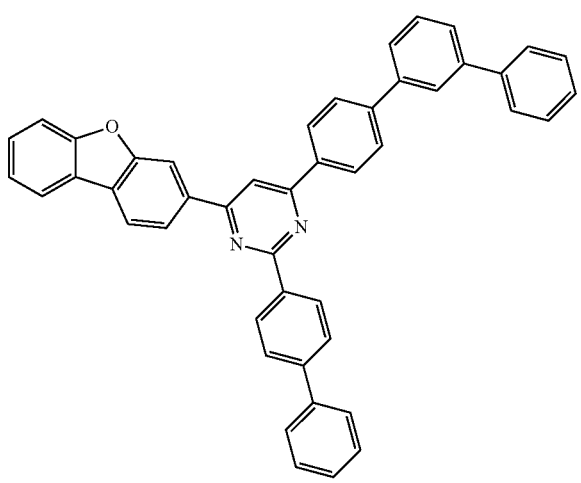

[B-81]

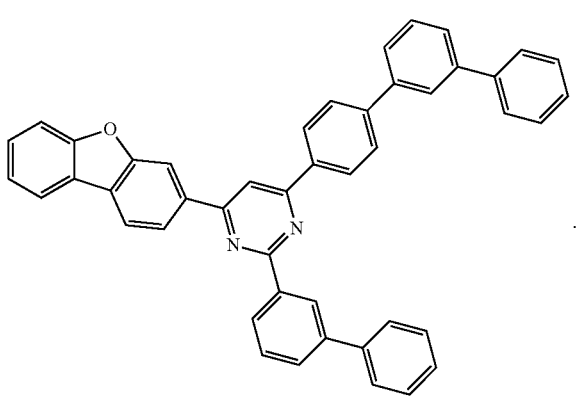

6. A composition for an organic optoelectronic device, comprising
the compound for an organic optoelectronic device of claim 1; and
a second compound for an organic optoelectronic device represented by Chemical Formula 2:

[Chemical Formula 2]

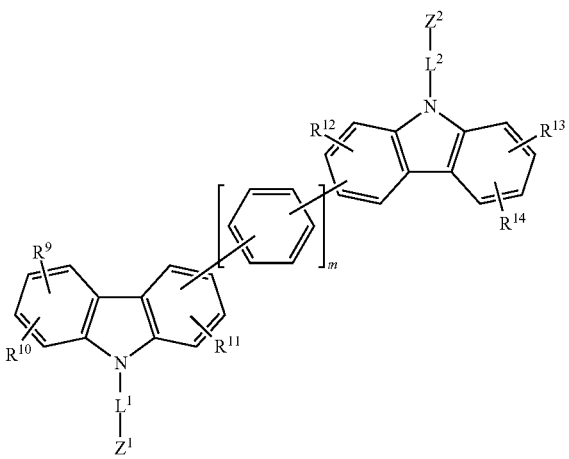

wherein, in Chemical Formula 2, $L^1$ and $L^2$ are independently a single bond, a substituted or unsubstituted C6 to C30 arylene group, a substituted or unsubstituted C2 to C30 heteroarylene group, or a combination thereof, $Z^1$ and $Z^2$ are independently a substituted or unsubstituted C6 to C30 aryl group, a substituted or unsubstituted C2 to C30 heterocyclic group, or a combination thereof, $R^9$ to $R^{14}$ are independently hydrogen, deuterium, a substituted or unsubstituted C1 to C20 alkyl group, a substituted or unsubstituted C6 to C30 aryl group, a substituted or unsubstituted C2 to C30 heterocyclic group, or a combination thereof, and m is an integer of 0 to 2;

wherein the "substituted" refers to replacement of at least one hydrogen by deuterium, a C1 to C4 alkyl group, a C6 to C18 aryl group, or a C2 to C30 heteroaryl group.

7. The composition for an organic optoelectronic device of claim 6, wherein $Z^1$ and $Z^2$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

8. The composition for an organic optoelectronic device of claim 6, wherein Chemical Formula 2 is one of structures of Group I, and
*-L$^1$-Z$^1$ and *-L$^2$-Z$^2$ are one of substituents of Group II:
[Group I]
C-1
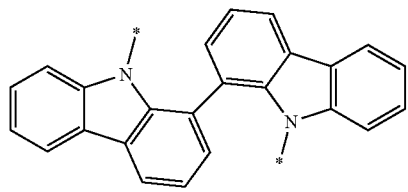
C-2
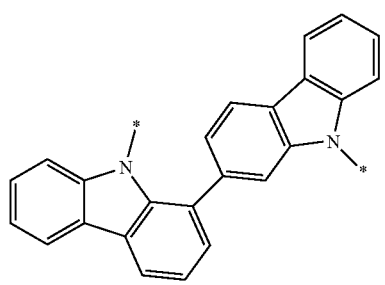
C-3
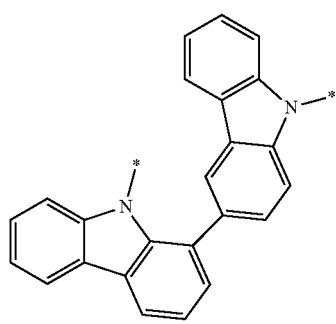
C-4
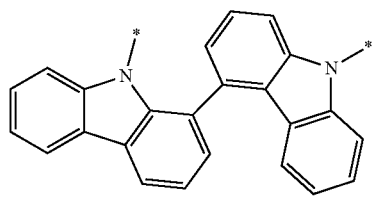
C-5
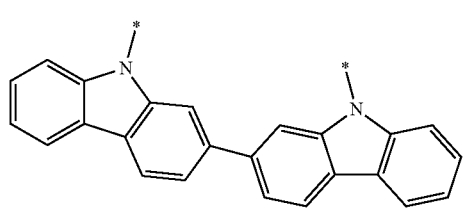
C-6
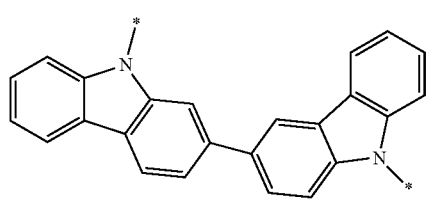
-continued
C-7
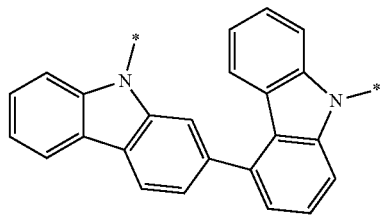
C-8
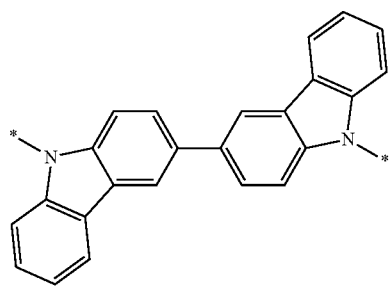
C-9
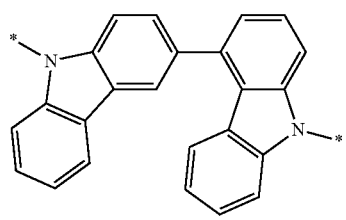
C-10
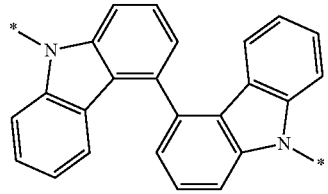
C-11
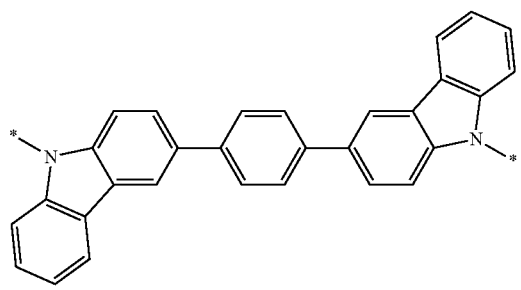
C-12
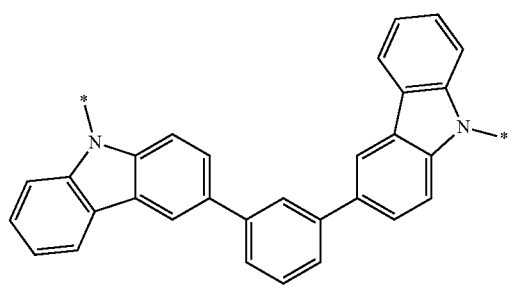

C-13
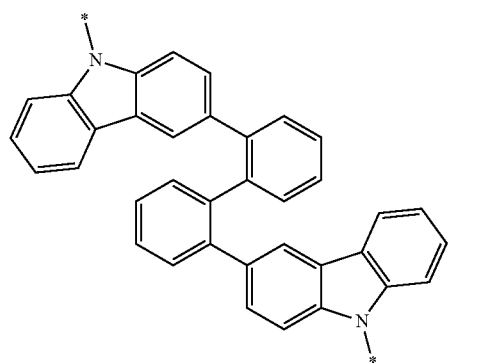
C-14
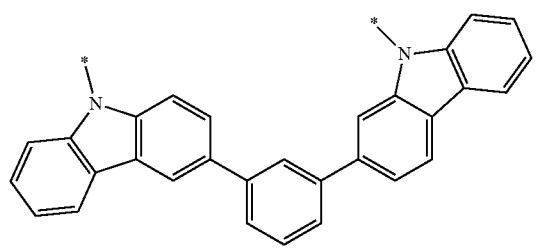
C-15
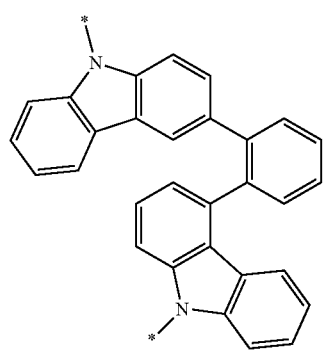
C-16
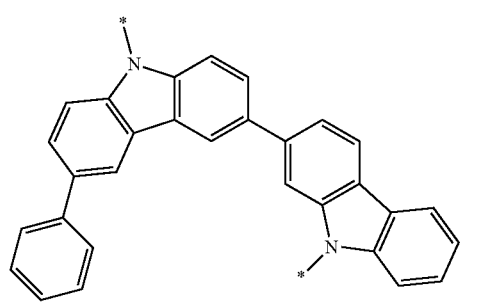
C-17
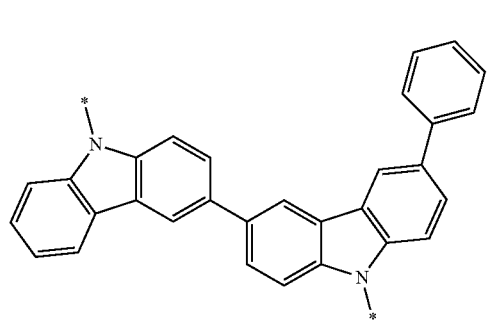
C-18
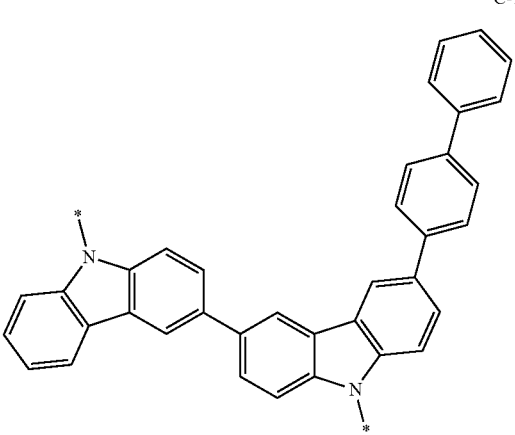
[Group II]
B-1
B-2
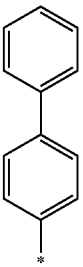
B-3
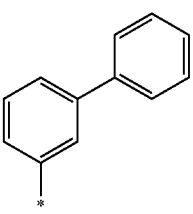
B-4
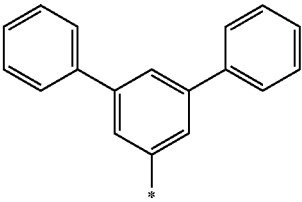
B-5
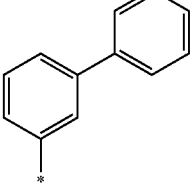
B-6
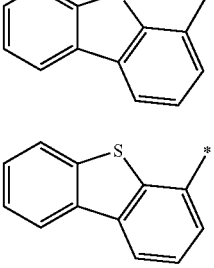

-continued
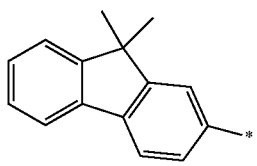
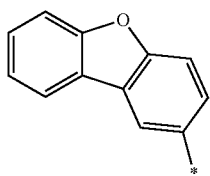
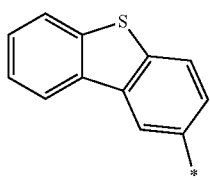
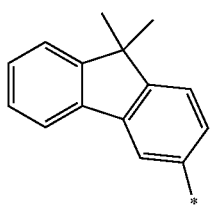
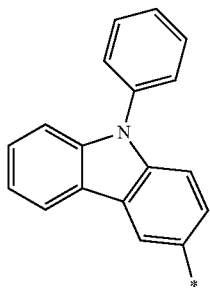
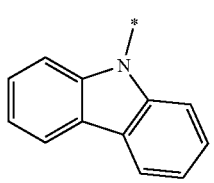
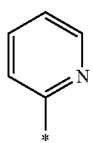
B-13
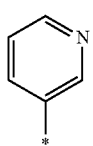
B-14
-continued
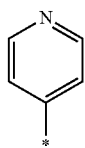
B-15
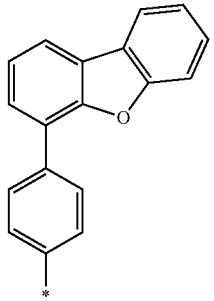
B-16
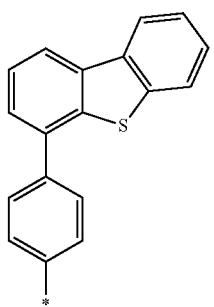
B-17
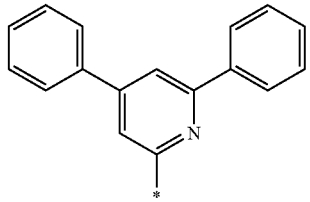
B-18
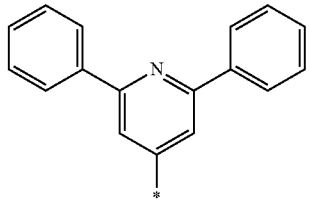
B-19
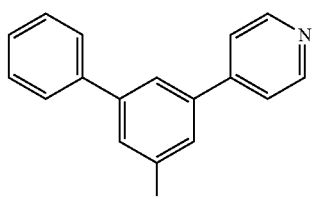
B-20
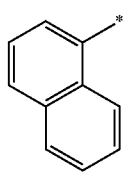
B-21

-continued

B-22 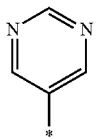

B-23 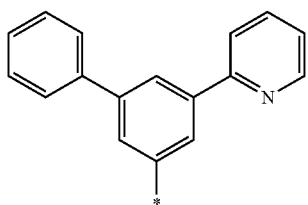

B-24 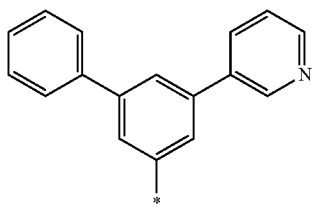

B-25 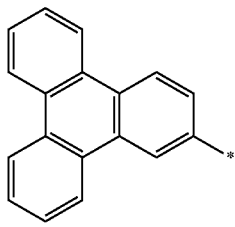

B-26 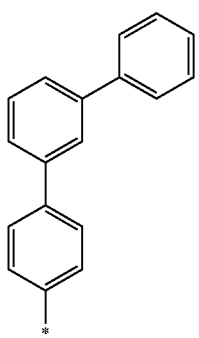

B-27 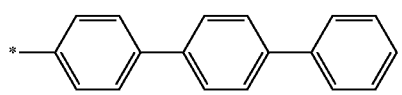

B-28 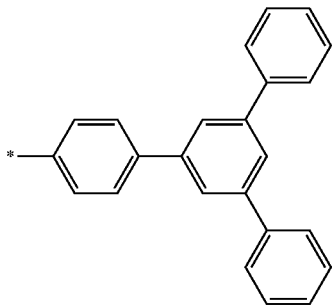

wherein, in Groups I and II, * is a linking point.

9. The composition for an organic optoelectronic device of claim 8, wherein Chemical Formula 2 is represented by Chemical Formula C-8 or Chemical Formula C-17 of Group I, and

*-$L^1$-$Z^1$ and *-$L^2$-$Z^2$ are selected from B-1, B-2, B-3, and B-16 of Group II.

10. An organic optoelectronic device comprising
an anode and a cathode facing each other, and
at least one organic layer disposed between the anode and the cathode,
wherein the organic layer includes the compound for an organic optoelectronic device of claim 1.

11. The organic optoelectronic device of claim 10, wherein the organic layer includes a light-emitting layer, and
the light-emitting layer includes the compound for an organic optoelectronic device.

12. The organic optoelectronic device of claim 11, wherein the compound for an organic optoelectronic device is included as a host of the light-emitting layer.

13. The organic optoelectronic device of claim 11, wherein the organic layer further includes at least one auxiliary layer selected from a hole injection layer, a hole transport layer, an electron blocking layer, an electron transport layer, an electron injection layer, and a hole blocking layer,
the auxiliary layer further includes an electron transport auxiliary layer that is adjacent to the light-emitting layer, and
the electron transport auxiliary layer includes the compound for an organic optoelectronic device.

14. A display device comprising the organic optoelectronic device of claim 10.

15. An organic optoelectronic device comprising
an anode and a cathode facing each other, and
at least one organic layer disposed between the anode and the cathode,
wherein the organic layer includes the composition for an organic optoelectronic device of claim 6.

16. A display device comprising the organic optoelectronic device of claim 15.

* * * * *